United States Patent
Ranalletta et al.

(10) Patent No.: US 8,863,788 B2
(45) Date of Patent: Oct. 21, 2014

(54) AUTOMATED MEDICAL LIQUID FILLING SYSTEM AND METHOD

(71) Applicant: Baxa Corporation, Englewood, CO (US)

(72) Inventors: Joseph Vincent Ranalletta, Centennial, CO (US); Loren Havener Hutchins, Parker, CO (US); Joshua Nathan Aumiller, Lakewood, CO (US)

(73) Assignee: Baxter Corporation Englewood, Englewood, CO (US)

( * ) Notice: Subject to any disclaimer, the term of this patent is extended or adjusted under 35 U.S.C. 154(b) by 0 days.

(21) Appl. No.: 13/738,845

(22) Filed: Jan. 10, 2013

(65) Prior Publication Data

US 2013/0192719 A1    Aug. 1, 2013

Related U.S. Application Data

(63) Continuation of application No. 13/208,141, filed on Aug. 11, 2011, now Pat. No. 8,353,318, which is a continuation of application No. 11/565,744, filed on Dec. 1, 2006, now Pat. No. 7,997,304.

(60) Provisional application No. 60/742,114, filed on Dec. 2, 2005.

(51) Int. Cl.
| | |
|---|---|
| *B65B 3/04* | (2006.01) |
| *B65B 3/00* | (2006.01) |
| *A61J 1/20* | (2006.01) |
| *A61M 5/31* | (2006.01) |

(52) U.S. Cl.
CPC .......... *B65B 3/003* (2013.01); *A61J 2001/2065* (2013.01); *A61M 2209/045* (2013.01); *A61M 2207/00* (2013.01); *A61M 2005/3114* (2013.01)

USPC .................. 141/25; 141/2; 141/104; 141/318; 604/407

(58) Field of Classification Search
USPC ...................... 141/2, 18, 25–27, 95, 104, 318; 604/407

See application file for complete search history.

(56) References Cited

U.S. PATENT DOCUMENTS

| | | |
|---|---|---|
| 3,935,883 A | 2/1976 | Stach |
| 4,030,498 A | 6/1977 | Thompkins |

(Continued)

OTHER PUBLICATIONS

Thierry Navarro, Advanced Technology, ingepump—A New Era in Medical Pump, 2005, 1 page.

(Continued)

*Primary Examiner* — Nicholas A Arnett

(57) ABSTRACT

A medical liquid filling system and associated methods are provided, the system comprising a disposable and a drive system. The disposable includes a tubular member and a piston slidably disposed within the tubular member for retraction and advancement within at least a first portion of the tubular member. The disposable may include a seal member for sealing the first portion of the tubular member and may be interconnected to the piston for co-movement therewith. The drive system may include a piston drive member selectively interconnectable to the piston for driven advancement and retraction of the piston within the tubular member. The drive system may be interconnected to a controller, which may be operable to automate or semi-automate various filling operations. A user interface may be interconnected to the controller for providing input of various system operation parameters, which may be communicated to the controller to facilitate automated or semi-automated operation of the filling system.

26 Claims, 30 Drawing Sheets

(56) References Cited

U.S. PATENT DOCUMENTS

| | | | |
|---|---|---|---|
| 4,187,890 A | | 2/1980 | Stach |
| 4,906,168 A | | 3/1990 | Thompson |
| 4,929,822 A | | 5/1990 | Nakamura et al. |
| 5,807,312 A | * | 9/1998 | Dzwonkiewicz ............... 604/30 |
| 5,911,252 A | | 6/1999 | Cassel |
| 5,947,890 A | | 9/1999 | Spencer et al. |
| 6,361,524 B1 | | 3/2002 | Odell et al. |
| 6,743,194 B2 | | 6/2004 | Sharon et al. |
| 6,915,823 B2 | | 7/2005 | Osborne et al. |
| 6,941,985 B2 | | 9/2005 | Kondo et al. |
| 6,991,002 B2 | | 1/2006 | Osborne et al. |
| 7,117,901 B2 | | 10/2006 | Martinell Gisper-Sauch et al. |
| 7,117,902 B2 | | 10/2006 | Osborne |
| 7,128,105 B2 | | 10/2006 | Tribble et al. |
| 7,163,035 B2 | | 1/2007 | Khan et al. |
| 7,240,699 B2 | | 7/2007 | Osborne et al. |
| 7,343,943 B2 | | 3/2008 | Khan et al. |
| 7,398,802 B2 | | 7/2008 | Baker |
| 7,997,304 B2 | * | 8/2011 | Ranalletta et al. ............... 141/25 |
| 8,353,318 B2 | * | 1/2013 | Ranalletta et al. ................ 141/2 |
| 2002/0117232 A1 | * | 8/2002 | Gisper-Sauch et al. ........... 141/2 |
| 2002/0139436 A1 | | 10/2002 | Rosen et al. |
| 2003/0187388 A1 | * | 10/2003 | Sharon et al. ................... 604/89 |
| 2005/0045242 A1 | * | 3/2005 | Osborne ........................ 141/27 |
| 2005/0045244 A1 | | 3/2005 | Hartness et al. |

OTHER PUBLICATIONS

Sapphire Engineering, Confluent Family of Products, Oct. 13, 2005, 1 page.

\* cited by examiner

AUTOMATED MEDICAL LIQUID FILLING SYSTEM AND METHOD

RELATED APPLICATIONS

This is a continuation of U.S. patent application Ser. No. 13/208,141, filed Aug. 11, 2011, entitled "AUTOMATED MEDICAL LIQUID FILLING SYSTEM AND METHOD", which claims priority to U.S. patent application Ser. No. 11/565,744, filed Dec. 1, 2006, now U.S. Pat. No. 7,997,304, issued Aug. 16, 2011, entitled "AUTOMATED MEDICAL LIQUID FILLING SYSTEM AND METHOD", which claims priority to U.S. Provisional Patent Application No. 60/742,114, filed Dec. 2, 2005, entitled "IMPROVED AUTOMATED LIQUID FILLING SYSTEM AND METHOD," each of which applications are incorporated herein by reference in their entirety.

FIELD OF THE INVENTION

The present invention relates to systems, apparatus and methods for automated filling of medical liquids. More particularly, embodiments of the present invention relate to systems, apparatus and methods for automated filling of medical liquids using a disposable syringe-like apparatus interconnectable with a drive system, a medical liquid source and a plurality of receptacles. The system, apparatus and methods may be employable to flow medical liquids to a plurality of receptacles to provide, for example, liquid medication in a desired volume.

BACKGROUND OF THE INVENTION

Providing medical liquids in a sterile and precise manner is desirable in many instances. For example, in the production of liquid medications, accurate and sterile quantities of medical liquid may be required. One apparatus employable to provide such medical liquids is a peristaltic pump. Peristaltic pumps work to deliver medical liquids by rotating a hub connected to anvils sprung against a flexible tubing line. As the anvils rotate in relation to the flexible tubing, the tubing is compressed to occlude one section from another section and to push fluids through the flexible tubing. The anvils may be spaced a predetermined distance from one another, which, in relation to a known internal diameter of the flexible tubing, enables the displacement of and dispensing of a calculable amount of fluid.

While peristaltic pumps are operable to deliver medical liquids, peristaltic pumps suffer in that the flexible tubing may move and/or twist during operation, the flexible tubing may deform over time from repeated compression and expansion, variable inlet and outlet pressure may be experienced, pulsatile flow with undesired flow reversal may occur, and/or the spring forces associated with the anvils may degrade over time. Such factors may potentially result in the dispensing of inaccurate volumes of medical liquids. As such, systems employing such peristaltic pumps typically require calibration at the outset of each medical liquid filling procedure. For example, medical personnel typically utilize a peristaltic pump system to fill a first receptacle with an amount of medical liquid corresponding to a known degree of movement of the pump. After filling, such personnel may generally compare such filled amount to a desired fill amount, and may often adjust the peristaltic pump to calibrate the system. Thus, time and/or materials may be spent in the calibration of a peristaltic pump. The tubing deformation may also lead to seepage around the anvils, thereby leading to cross-flow between the various sections of the tubing.

Peristaltic pumps also are limited by the intake speed of rotation. As the hub of the peristaltic pump is rotated, a pressure differential is created at both the inlet and outlet of the pump. These inlet and outlet pressures are generally tied to one another as the rotation rate of the hub relates to both the inlet and outlet pressures. As may be appreciated, the operable inlet pressure may be limited by the vapor pressure of the liquid being dispensed. If the inlet pressure is too high in relation to the vapor pressure of the liquid, a portion of the liquid may evaporate upon intake, which is undesirable for many reasons (e.g., the dispensing of inaccurate liquid volumes). Correspondingly, the outlet pressure, and thus the dispensing rate, is limited by the operable inlet pressure, which may be substantially less than the operable outlet pressure, which may not be limited by the vapor pressure of the liquid. Thus, the maximum rate of fluid flow speed may be substantially less than desired due to the inherent tying of the inlet pressure to the outlet pressure in the peristaltic pump.

SUMMARY OF THE INVENTION

In view of the foregoing, one objective of embodiments of the present invention may be to facilitate accurate and repeatable dispensing of medical liquids (e.g., liquid medications, medical quality solvents, such as pharmaceutical quality water, etc.). A related objective may be to facilitate accurate and repeatable dispensing of various medical liquids free from significant or nominal calibration.

Another objective of embodiments of the present invention may be to facilitate an optimal rate of medical liquid flow.

Yet another objective of embodiments of the present invention may be to facilitate the automated or semi-automated dispensing of medical liquids.

Another objective of embodiments of the present invention may be to facilitate multiple medical liquid filling applications with a single apparatus and/or system.

Yet another objective of embodiments of the present invention may be to facilitate dispensing of medical liquids free from input and/or calibration relating to medical liquid type.

One or more of the above objectives and additional advantages may be realized by an inventive medical liquid filling system that comprises a disposable for use in automated filling of at least one receptacle with a medical liquid, an automated drive system for use in the automated filling of at least one receptacle with a medical liquid, a system comprising both a disposable and an automated drive system, and methods for filling at least one receptacle with a medical liquid (e.g., employing an inventive disposable, automated drive system and/or combinative system).

In the inventive system, a syringe-like disposable is included which comprises a tubular member and a piston slidably disposed in the tubular member for retraction and advancement within at least a first portion of the tubular member. The disposable further includes a seal member for sealing a distal end of the first portion of the tubular member. The system also includes an automated drive system that comprises a piston drive member that is selectively interconnectable to the piston of the disposable for automated (e.g., driven) advancement and retraction within the tubular member. Of note, the utilization of a disposable that comprises a tubular member and piston slidably disposed therewithin facilitates the precise flow of a predetermined amount of medical liquid into and out of the tubular member of the disposable during use of the inventive system. In that regard, the tubular member is preferably of rigid construction, thereby enhancing the accuracy and repeatability of medical liquid draw/dispensation volumes during use. Further, the tubular member is preferably cylindrical, thereby accommodating advancement/retraction of the piston and piston drive member along a linear path so as to further enhance accurate and repeatable performance.

In one aspect, the seal member of the disposable is interconnected to the piston of the disposable for co-movement therewith and slidable engagement within a second portion of the tubular member, wherein the second portion is located distal to the first portion of the tubular member. In this regard, the seal member may be spaced from the piston by a fixed distance that is at least as great as the length of the first portion of the tubular member. In one embodiment, the seal member is spaced from the piston by a fixed distance that is greater than the length of the first portion of the tubular member.

In another aspect, the piston of the disposable may comprise a resilient member (e.g., ring-shaped and peripherally disposed), wherein when the piston is located at a first position within the first portion of the tubular member the resilient member sealably engages the tubular member. Further, the tubular member may be provided with a plurality of portions differing in dimensions (e.g., cylindrical portions having different diameters) so that the piston may be located in a second position within a portion other than the first portion, wherein the resilient member is expanded when the piston is located in the second position relative to when the piston is located in the first position. For example, the tubular member may be provided so that when the position is located in a first position the resilient member compressively engages the first portion of the tubular member, and so that when the piston is located in the second position the resilient member is compressed less or is free from compressive engagement (e.g., within a second portion of the tubular member). As will be further described, the piston may be located in the second position prior to use (e.g., during transport and storage), then moved to the first position for filling operations thereby preserving the integrity of the resilient member prior to use.

In a further aspect, the disposable may include a first connection member interconnected to the seal member, and the piston drive member may include a second connection member, wherein the first and second connection members are selectively interconnectable and disconnectable. More particularly, the first and second connection members may be provided so that they are restrainably interconnected when co-located within the tubular member (e.g., within a second portion thereof). By way of example, the first and second connection members may be provided so that when the piston is located in a second position as noted above, the first and second connection members are readily disconnectable. In turn, when the piston is advanced so that it is in the above-noted first position, the first and second connection members restrainably interconnect so that subsequent advancement/retraction of the piston drive member affects predeterminable co-movement of the piston of the disposable.

In one embodiment, the first and second connection members may comprise complimentary male and female members. For example, the female connection member may include a plurality of fingers that define an opening therebetween for receiving a complimentary male connection member when the female connection fingers are at least partially, distally positioned outside of the tubular member. In turn, as the male connection member is received within the opening of the female connection member and the female connection member is driven into the distal end of the tubular member (e.g., by the piston drive member) the female connection member fingers may envelop at least a portion of the male connection member (e.g., a bulbous end portion).

As may be appreciated, such an interconnection arrangement conveniently interfaces with the above-noted, preferred advancement/retraction linear path of the piston drive member and piston.

In an additional aspect, the disposable may also include a valve that is fluidly interconnected to a proximal end port of the tubular member. The valve may be provided with a plurality of ports, wherein in a first valve position a first valve port is fluidly interconnected to the tubular member, and wherein in a second valve position, a second valve port is fluidly interconnected to the tubular member (e.g., via a proximal end port). By way of example, a medical liquid source may be fluidly interconnected to the first valve portion wherein medical liquid may be drawn into the tubular member when the valve is positioned in the first valve position, and one or more receptacles may be fluidly interconnected to the second valve port wherein at least a portion of the medical liquid drawn into the tubular member may be dispensed from the tubular member to the receptacles when the valve is located in the second valve position.

The automated drive system may further include a valve drive member that is selectively interconnectable to the valve for automated (e.g., driven), alternate positioning of the valve between the first and second valve positions. In one embodiment, the valve may include a valve housing and a valve stem slidably disposed within the valve housing (e.g., for linear and/or rotational movement therewithin). For interconnection purposes, the valve drive member may include one of a complimentary projection(s) and opening(s) (e.g., for receiving the projection(s)) and the valve stem may include the other one of the complimentary projection(s) and opening(s).

The valve stem may include at least first and second channels, wherein the first channel fluidly interconnects the first valve port and the tubular member when the valve is in the first valve position, and wherein the second channel fluidly interconnects the second valve port and the tubular member when the valve is in the second valve position. By way of example, the first and second channels may comprise separate accurate pathways disposed, (e.g., offset), about a perimeter of the valve stem (e.g., wherein the valve stem may be rotated to control medical liquid flow into/out of the disposable).

In a further aspect, the automated drive system may further include at least one drive motor interconnected with the piston drive member, a reference member, and a sensor to sense at least one degree of relative movement (e.g., a predetermined amount of relative linear movement) between the piston drive member and the reference member and to provide an output signal in relation thereto. Further, the drive system may include a controller for receiving the output signal from the sensor and providing a control signal to the drive motor. By way of example, the drive system may be provided so that upon sensing a predetermined degree of relative movement that corresponds with a desired amount of medical liquid to be dispensed to a receptacle, the controller may terminate operation of the drive motor. Further, in response to the sensor output signal, the controller may be operative to provide a control signal so as to change the above-noted valve from one of the first and second valve positions to the other of the first and second valve positions (e.g., so as to facilitate automated, alternate drawing and dispensing operations).

In yet a further aspect, the drive motor of the automated drive system may be controlled to automatically provide a predetermined maximum force to the piston drive member so as to yield an internal pressure within the disposable that is less than a predetermined desired magnitude. By way of example, the drive system and/or disposable may include a pressure sensor (e.g., to directly sense the pressure applied by the piston drive member or to the piston) that provides an output signal employable to control the drive motor. Alternatively, the drive system may comprise a drive motor monitor that provides an output signal that reflects the magnitude of the noted force output.

More particularly, the drive motor may include a moveable output member interconnectable to the piston drive member, a magnetic field member for inducing movement of the moveable output motor, and a sensor for sensing a position of the moveable output member in relation to the magnetic field member and for providing an output signal to a controller in corresponding relation thereto. The output signal may be indicative of, for example, one or more of a force, torque, velocity and/or position of the moveable output member. The controller may be operable to compare the output signal to a predetermined operating parameter (e.g., a fill-related parameter) and to provide an appropriate control signal to the magnetic field member in relation thereto to operate the drive motor within a predetermined desired operating range (e.g., an operating range corresponding with an apparent force of advancement or an apparent force of retraction of the piston). As the piston drive member is interconnectable to the piston and moveable operating member, the system may be operable to achieve a predetermined pressure range within the tubular member via control of the drive motor. Thus, the system may be operable to achieve a predetermined desired pressure range free from input relating to a fluid-type parameter.

As may be appreciated, the inventive system may be provided so that disposable further includes a first fluid line interconnected or interconnectable at one end to a first valve port of a valve and interconnectable at another end to at least a first medical liquid source. Further, a second fluid line may be interconnected or interconnectable at one end to a second valve port of a valve and interconnectable at the other end to at least one receptacle, wherein the system is operative to pump a medical liquid from the medical liquid source through the first fluid line, into/out of the tubular member, and through the second fluid line free from occlusion of the first and second fluid lines. Such an arrangement facilitates the maintenance of calibration parameters (e.g., in distinction to the use of a peristaltic pump arrangement).

Certain embodiments of the present invention also provide various methodologies relating to the filling of at least one interconnectable receptacle with a medical liquid. In one characterization, the method includes the steps of establishing a physical interconnection between a disposable and an automated drive system, wherein the disposable includes a tubular member and a piston slidably disposed therein for retraction and advancement within a first portion, and wherein the automated drive system includes a piston drive member selectively interconnectable to the piston of the disposable. The method further includes the steps of using the piston drive member to retract the piston within the first portion of the tubular member (e.g., along a linear path) so as to draw a predetermined volume of a medical liquid into the tubular member, and employing the piston drive member to advance the piston within the first portion of the tubular member (e.g., along a linear path) to dispense at least a portion of the predetermined volume of medical liquid into at least one interconnectable receptacle. Of note, the method further provides for sealing a distal end of the first portion of the tubular member during both the using and employing steps.

In one aspect, the method may further comprise the steps of establishing a fluid interconnection between a source for the medical liquid and the disposable, and repeating the using, employing and sealing steps a plurality of times to at least partially fill each of a plurality of receptacles while maintaining the interconnections between the disposable and automated drive system and between the medical liquid source and the disposable. As may be appreciated, between successive ones of such plurality of times, the method may further include the step of fluidly interconnecting the disposable with different ones of the plurality of receptacles.

In another aspect, the piston drive member may be utilized to advance the piston of the disposable to dispense a predetermined portion of the predetermined volume of medical liquid drawn into the tubular member, and repeating such utilizing step a plurality of times to at least partially fill each of a corresponding plurality of receptacles while maintaining the above-noted interconnections. Stated differently, a given predetermined volume of medical liquid that is drawn into the tubular member may be sufficient to at least partially fill a plurality of receptacles in the above-noted employing step.

The method may be provided so that, following each advancement of the piston drive member to at least partially fill a given receptacle, the piston drive member may be automatically controlled so as to retract the piston a minimal amount sufficient to reduce or even avoid undesired drippage downstream of the disposable (e.g., at the end of a tubing line from which the medical liquid is dispensed into the receptacles). Such an optional "draw-back" step is readily facilitated by the piston drive approach of particular embodiments of the present invention. In this regard, the method may including the steps of flowing the medical liquid through a port (e.g., a valve port, a proximal end port of the tubular member, a fluid line port) during the employing step, and controlling the piston drive member to retract the piston within the tubular member to draw a predetermined volume of the medical liquid into the tubular member via the port.

In another aspect, the method may provide for sensing at least one degree of relative movement between the piston drive member and a reference member of the automated drive system to provide an output signal for use in at least one of the above-noted using (e.g., piston retraction) and employing (e.g., piston advancement) steps. As may be appreciated, the degree of relative movement may correspond with a given predetermined amount of medical liquid to be dispensed into a given receptacle. Further, the sensing step may provide for the detection of a plurality of degrees of relative movement between the piston drive member and the reference member so as to provide an output signal in corresponding relation to each of the detected degrees of relative movement. In turn, the method may include the step of processing the output signal to obtain at least one rate value indicative of a rate of relative movement between the piston drive member and the reference member, and comparing such rate value with at least one predetermined value to identify the occurrence of a predetermined operating condition (e.g., undesired occlusion and/or undesired leakage downstream of the disposable). The method may further provide for automatic termination and/or the provision of a user output indication upon the identification of such an occurrence.

In a further aspect, the using step (e.g., piston retraction) and employing step (e.g., piston advancement) may each comprise the step of flowing the predetermined volume of medical liquid through a common port of the tubular member. By way of example, such common port may be located at a proximal end of the tubular member. Further in this regard, the establishing step may include the step of interconnecting a valve of the disposable with a valve drive member of the automated drive system. In one embodiment, the valve may comprise a valve housing fluidly interconnected to the proximal port of the tubular member, and a valve stem positioned within the valve housing.

In conjunction with this aspect, the method may further include the step of utilizing the valve drive member of the automated drive system to automatically and alternately position the valve in a first valve position and in a second valve position, wherein the first valve position is maintained during the using step and second valve position is maintained during the employing step. In one embodiment, the method may provide for automatic positioning of the valve in the first valve position prior to the using step (e.g., piston retraction), and locating the valve in the second valve position after the using step and prior to the employing step (e.g., piston advancement).

In an additional aspect, the inventive method may include the step of automatically controlling the piston drive member of the automated drive system to retract the piston within the tubular member during the using step (e.g., piston retraction) to realize medical liquid flow within a first rate range, and to advance the piston within the tubular member during the employing step (e.g., piston advancement) to realize medical liquid flow within a second rate range, wherein the first rate range and the second rate range are at least partially non-overlapping. Stated differently, the method may be adapted so that the rate of medical liquid flow into the disposable is different than the rate of medical liquid flow out of the disposable. As may be appreciated, such a capability facilitates optimization of medical liquid following operations. That is, differing maximum flow rates into and out of the disposable may be realized. For example, in applications where medical liquid is drawn into the disposable through a relatively large fluid interconnection line (e.g., large tubing diameter), and dispensed by the disposable through a relatively small fluid interconnection line (e.g., small tubing diameter) and/or into relatively small volume syringe receptacles, a higher maximum rate of flow into the disposable than may be accommodated.

Further method advantages may be realized when a user interface is connected to an automated drive system. For example, the method may include the step of receiving user input at the user interface to set a fill-related value, corresponding with, for example, a predetermined volume of medical liquid to be drawn into the disposable, for use in the above-noted using step (e.g., piston retraction). Alternatively and/or additionally, the method may include the steps of fluidly interconnecting the disposable with at least one of a fluid connection line and a fluid receptacle (e.g., a tubing line of a given bore size and/or a syringe or vial of a given volume), and receiving user input at a user interface to set a fill-related value, corresponding with, for example, an acceptable maximum flow rate associated with the interconnected fluid connection line and/or fluid receptacle, for use in the employing step (e.g., piston advancement step). As may be appreciated, this functionality allows a user to maximize receptacle fill rates while avoiding undesired fluid pressure levels within the disposable. Additionally and/or alternatively, the method may also provide for selecting the disposable from a plurality of different sized disposables employable with the automated drive system, and receiving user input at the user interface to set a size-related value, corresponding with, for example, the selected disposable, for use in at least one of the using step (e.g., piston retraction) and employing step (e.g., piston advancement). Additionally and/or alternatively, the method may also include the step of receiving user input at the user interface to set parameters relating to attributes of or affecting the given medical liquid to be drawn into/dispensed by the disposable (e.g., viscosity, density, atmospheric pressure, etc.), for use in at least one of the using and/or employing steps.

In yet another aspect, the inventive method may include the step of automatically controlling the piston drive member to automatically adjust a force applied by the piston drive member to the piston of the disposable during at least a portion of at least one of the using (e.g., piston retraction) and employing (e.g., piston advancement) steps. In turn, the automatic controlling step may provide for the maintenance of the applied force within a predetermined range, wherein a predetermined maximum of the predetermined range corresponds with a predetermined maximum desired fluid pressure for the disposable. Relatedly, a predetermined minimum of the predetermined range may be established to be within a given relatively small percentage of the predetermined maximum (e.g., less than 10%) so that the medical liquid flow rate into and/or out of the disposable is maximized.

In conjunction with this aspect, the automatically controlling step may include the step of utilizing an output signal of a pressure sensor that is included with either the disposable or the automated drive system. By way of example, the pressure sensor may be interconnected to the piston drive member of the automated drive system to measure the magnitude of force being applied to the piston of the disposable. Alternatively and/or additionally, a pressure sensor may be integrated into the disposable to measure the noted force and provide an output signal to the automated drive system.

In another approach, the automatically controlling step may include the step of utilizing an output signal associated with the drive motor comprising the automated drive system and interconnected to the piston drive member, wherein the output signal is indicative of the force being applied to the piston of the disposable. The method may include the steps of providing a control signal to a magnetic field member of a drive motor and inducing movement of a moveable output member via the magnetic field member in relation to the control signal, the moveable output member being interconnectable to a piston drive member. The method may further include the steps of sensing a relative position of the moveable output member in relation to the magnetic field member, repeating the providing, inducing and sensing steps a plurality of times, and determining a pressure within the tubular member based upon the repeating step. The method may further include the steps of outputting an output signal based on the sensing step, comparing this output signal to a predetermined fill-related value, adjusting the control signal based upon this comparing step, and providing an adjusted control signal to the magnetic drive member to adjust the pressure within the tubular member.

In yet a further aspect, the inventive method may include the steps of packaging the disposable within an enclosure prior to the establishing step (e.g., interconnecting the disposable to the automated drive system), sterilizing the disposable, and removing the disposable from the enclosure prior to the establishing step. Further, the method may include the steps of completing the packaging step at a first location (e.g., a disposable production and/or assembly location), transporting the disposable within the enclosure from the first location to a second location (e.g., a hospital pharmacy or other medical liquid preparation location), and completing the removing, establishing, using and employing steps at the second location.

In conjunction with this aspect, the inventive method may further comprise the steps of positioning the piston of the disposable within a second portion of the tubular member prior to the packaging step and locating the piston within the above-noted first portion of the tubular member after the removing step, wherein a resilient member comprising the piston is compressed less or not at all during transport and storage relative to the degree of compression that may be experienced during use of the disposable (e.g., when the piston and resilient member are located in the first portion of the tubular member for medical liquid draw/dispensation). Similarly, when the disposable includes a valve, the inventive method may include the steps of positioning a valve stem of the valve within a first portion of the valve (e.g., a first portion of a valve housing of the valve) prior to the packaging step and locating the valve stem within a second portion of the valve (e.g., a second portion of the valve housing of the valve) after the removing step, wherein the valve stem is compressed less or not at all during transport and storage relative to the degree of compression that may be experience during use of the disposable (e.g., when the valve stem is located in the second portion of the valve for medical liquid draw/dispensation).

In a related aspect, the inventive method may comprise linearly advancing a piston drive member to a first point of linear travel, the first point of linear travel corresponding with receipt of a first connection member (e.g., a male member) by a second connection member (e.g., a female member). The method may further comprise the step of linearly advancing the piston drive member to a second point of linear travel, this second point of linear travel being located proximal of the first point of linear travel, thereby restrainably engaging the first connection member and second connection member. The method may further comprise linearly advancing the piston drive member to a third point of linear travel, this third point of linear travel being located proximal of the first and second points of linear travel, the third point of linear travel corresponding with the above-noted sealing the first portion step. The method may further comprise the step of linearly moving the piston drive member to a fourth point of linear travel, the fourth point of travel being located proximal of the third, second and first points of linear travel, and linearly retracting the piston drive member to the third point of linear travel. The method may further comprise the step of repeating the linearly moving and linearly retracting steps a plurality of times to fill a plurality of receptacles with a medical liquid. The method may further comprise the step of linearly retracting the piston drive member distal of the first point of linear travel, and removing a disposable from a drive system.

In another aspect, a disposable is provided for use in a system for the automated filling of a least one interconnectable receptacle with a medical liquid. The disposable may include a housing that includes a tubular member and a valve housing. A piston may be slidably disposed in the tubular member and a valve may be disposed in the valve housing. The valve may be positionable in a first valve position where a first valve port is fluidly interconnected to the tubular member and the valve may be positionable in a second valve position where a second valve port is fluidly interconnected to the tubular member. In an embodiment, a seal member may be provided for sealing a distal end of the tubular member. The seal member may be positioned a fixed distance from the piston. A valve stem may be slidably and rotatably disposed within the valve housing.

In yet another aspect, a system for automated filling of at least one interconnectable receptacle with a medical liquid is provided. The system may include a piston drive member, a piston drive motor, a piston drive sensor, a valve drive member, a valve drive motor, a controller and a mount. The piston drive member may be selectively interconnectable to a piston of a disposable. The piston drive motor may be interconnected to the piston drive member and may be operable to reciprocate the piston drive member. The piston drive sensor may be operable to sense a position of the piston drive member and provide an output to the controller. The valve drive member may be operable to interface with a valve of the disposable and may be selectively positionable in at least two positions. The valve drive motor may be interconnected to the valve drive member and may be operable to position the valve drive member. The controller may be operable to determine an output pressure of a disposable interconnected to the system based on input level to the piston drive motor and an output signal from the piston drive sensor. The mount may be operable for selectively engaging and fixing a disposable relative to the piston drive member.

In an additional aspect, a method for the automated preparation of a least one predetermined volume of a medical liquid is provided. The method may include establishing an interconnection between a disposable and an automated drive system, drawing a predetermined volume of a medical liquid from a first container through a first port on the disposable, through a valve in a first position in the disposable, and into a tubular member of the disposable. The method may further include reorienting the valve into a second position after drawing the medical liquid into the tubular member of the disposable. The method may further include dispensing a predetermined volume of the medical liquid into a second container by dispensing the liquid from the tubular member, through the valve in the second position, through a second port on the disposable, and into the second container. The method may further include sealing, with a movable seal, a portion of the tubular member during the drawing, reorienting, and dispensing steps.

In an embodiment of the present aspect, the process of drawing and dispensing may be reversed so that the medical liquid is drawn from the second container and dispensed into the first container thereby mixing or agitating the medical liquid. By way of example, the first container of the present aspect may be one of a bottle, a bag, or a vile. By way of example, the second container of the present aspect may be one of a bottle, a bag, a vile, a hypodermic syringe, an intravenous syringe, and an oral syringe.

The present aspect may further include repeating the method a plurality of times to transfer medical liquid from the first container to the second container. In a related aspect, the method may further include disconnecting the second container and sequentially connecting a plurality of containers while repeating the method a plurality of times and thereby at least partially filling a plurality of medical liquid containers with medical liquid drawn from the first container. In another related aspect, the method may further include disconnecting the first container and sequentially connecting one or more containers while repeating the method one or more times. In this regard, medical liquid from multiple sources may be mixed or compounded into a single receiving container.

Numerous additional aspects, features and advantages of the present invention will become apparent to those skilled in the art upon consideration of the further description that follows.

BRIEF DESCRIPTION OF THE DRAWINGS

FIG. 3c is a side view of the tubular member of FIG. 3a.

FIG. 5a is a perspective view of one embodiment of the valve stem of the disposable of FIG. 3a.

FIG. 5b is a side view of the valve stem of FIG. 5a.

FIG. 5c is a top view of the valve stem of FIG. 5a.

FIG. 12b is a flow chart illustrating particular portions of the flow chart of FIG. 12a.

FIG. 12c is a flow chart illustrating particular portions of the flow chart of FIG. 12a.

DETAILED DESCRIPTION

Figure 1:
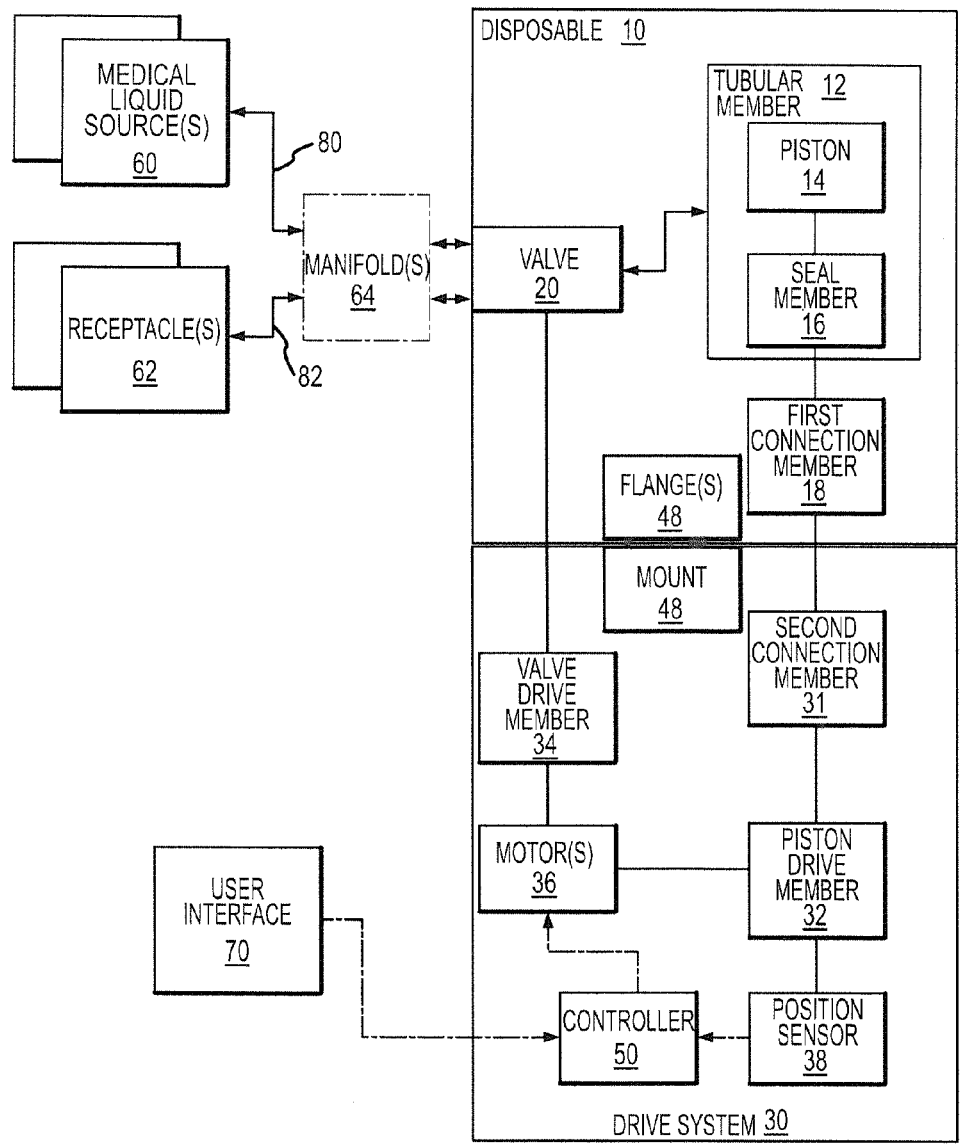
FIG. 1 is a schematic view of one embodiment of an automated medical liquid filling system of the present invention.
Figure 2:
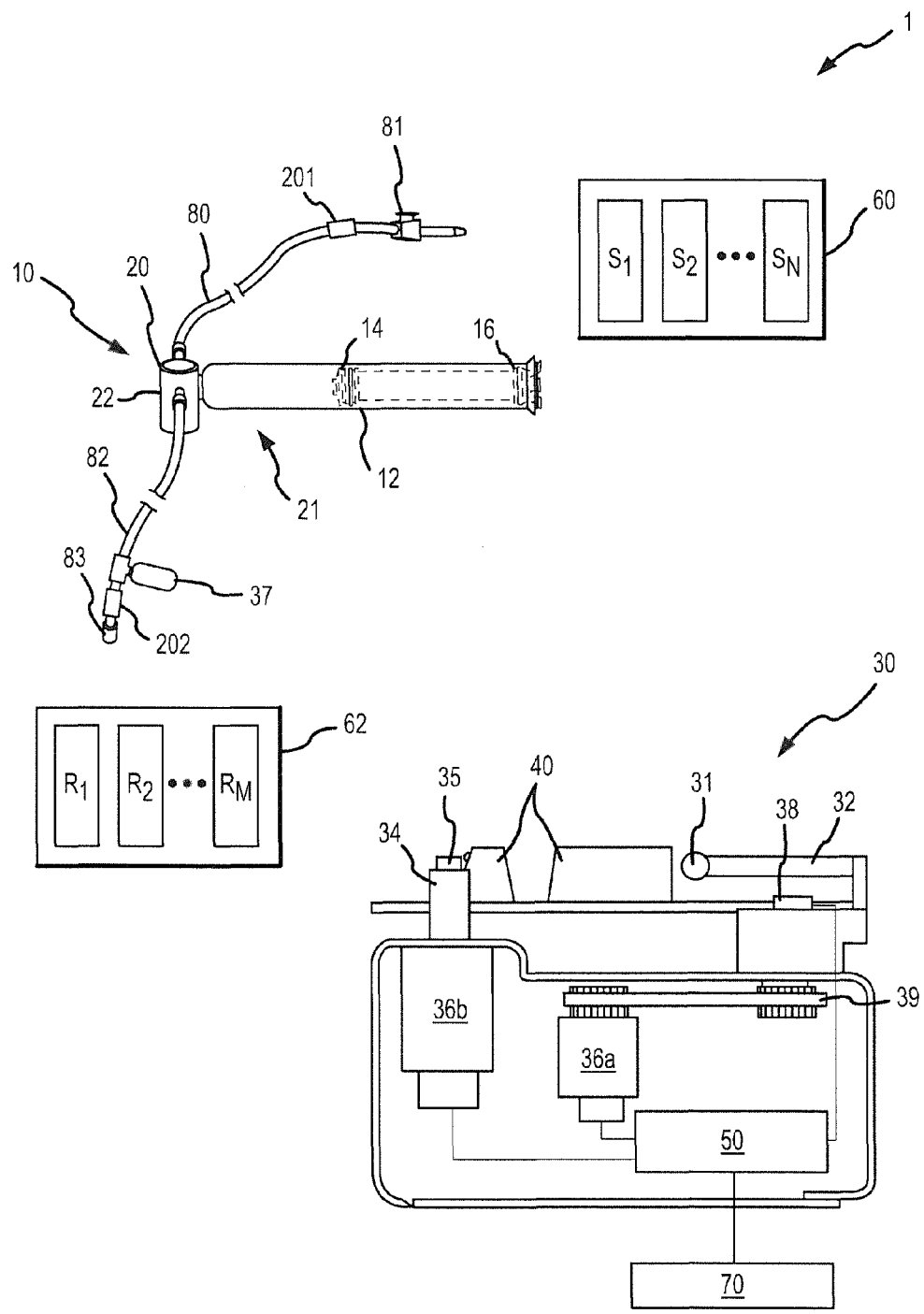
FIG. 2 is a partial schematic, partial perspective view of one embodiment the automated medical liquid filling system of the present invention with a portion of the drive system cut away to show internal features.

Reference is now made to FIGS. 1 and 2, which illustrate one embodiment of a medical liquid filling system of the present invention. The medical liquid filling system 1 generally includes a disposable 10, a drive system 30, one or more medical liquid sources 60 ("medical liquid source(s)") and one or more receptacles 62 ("receptacle(s)"). The disposable 10 may be selectively engageable and disengageable with the drive system 30 via flanges 48 and a mount 40. The medical liquid source(s) 60 may be fluidly interconnectable to the disposable 10 via a first fluid line 80 and an optional manifold 64 (e.g., included when multiple medical liquid sources are provided). Similarly, the receptacle(s) 62 may be fluidly interconnectable to the disposable 10 via a second fluid line 82 and the optional manifold 64.

The disposable 10 may include a housing 21 that may include a valve housing 22 and a tubular member 12. The housing 21 may be a single piece (e.g., a one piece molded part) or may be constructed of multiple individual parts interconnected. The disposable 10 may include a valve 20 for selective fluid interconnection with the first and second fluid lines 80, 82. A first filter 201 may be disposed in line with the first fluid line 80. A second filter 202 may be disposed in line with the second fluid line 82. Whether or not a filter is needed and the location of the filter (e.g., on the first fluid line 80, on the second fluid line 82, or on both the first and second fluid lines 80, 82) may be determined based on the characteristics of the medical liquid. In turn, the disposable 10 may include the tubular member 12, which is fluidly interconnectable to the valve 20, and a piston 14 for drawing a medical liquid into and dispensing a medical liquid out of the tubular member 12. In this regard, the piston 14 may be slidably disposed in the tubular member 12 for retraction and advancement within at least a first portion of the tubular member 12. A seal member 16 may seal a distal portion of the tubular member 12, and in one embodiment the seal member 16 is interconnected with the piston 14 for co-movement therewith.

In operation and as is discussed in further detail below, when the valve 20 is positioned in a first valve position, the piston 14 may be retracted to draw fluids from the medical liquid source(s) 60 into the tubular member 12 via the first fluid line 80 and the valve 20. When the valve 20 is positioned in a second valve position, the piston 14 may be advanced to dispense fluids in the tubular member 12 to the receptacle(s)

62 via the valve 20 and the second fluid line 82. As described in further detail below, since the piston 14 may be retracted and advanced at different speeds, the filling system 1 may be operable at different intake and dispensing pressures, therefore enabling the filling system 1 to dispose medical liquids at a materially different rate than the draw rate. Moreover, the first fluid line 80 may have a different internal diameter than that of the second fluid line 82. For example, the first fluid line 80 may be larger than the second fluid line 82 (e.g., the inner diameter of the first fluid line 80 may be twice that of the second fluid line 82) in applications where a relatively high rate of flow into the disposable 10 is desired and a relatively high degree of control of the outflow from the disposable 10 is desired. The relatively higher degree of control of a smaller diameter fluid line may, for example, be due to less flexing of the tube walls resulting in greater volumetric accuracy. In an embodiment, the ratio of the inner diameter of the first fluid line 80 to that of the second fluid line 82 may be between 2:1 and 1:2. The inner diameters of the first fluid line 80 and the second fluid line 82 may also be varied to achieve specific flow parameters, such as overall flow rate, flow velocity and pressure at various points throughout the system.

An accumulator 37 may be fluidly attached to the second fluid line 82. The accumulator 37 may be operable to smooth pressure pulsations within the second fluid line 82 that may result from the advancing of the piston 14 within the tubular member 12 during dispensing. The accumulator 37 may also prevent pressure spikes within the second fluid line 82 that could result in volumetric inaccuracy or a higher then desired velocity of flow into the receptacle(s) 62.

Additionally, the disposable 10 may comprise one or more relatively rigid materials (e.g., substantially non-deformable under normal operating conditions). Thus, the disposable 10 may comprise a relatively stable known volume that is restricted from deforming, which stabilizes dispensing accuracy and repeatability. The filling system 1 may thus be employable to provide medical liquids from the medical liquid source(s) 60 to the receptacle(s) 62 to obtain a contained medical liquid (e.g., a liquid medication) of a desired volume. Further, such capability may be realized free from occluding or deforming the fluid lines 80, 82, thereby yielding a filling system 1 that may be utilized without requiring a dispensing calibration operation (e.g., an action corresponding with the filling of a first receptacle and cross-checking of the dispensed volume in relation to a desired volume).

The medical liquid source(s) 60 may include any medical liquid, such as a liquid medication (diluted or concentrated), a solvent or other solution. As may be appreciated, the medical liquid source(s) 60 may be any container adapted to contain a relatively large quantity of a medical liquid (e.g., medical liquid bags or bottles).

The receptacle(s) 62 may be substantially empty or may include a medicine containing substance (e.g., a dry powder or concentrated suspension), or a solvent. As may be appreciated, the receptacle(s) 62 may be any one of vials, ampoules, syringes, bottles, medical liquid bags or other containers adapted to receive and contain liquid medications or other medical liquids.

In one embodiment, the medical liquid source(s) 60 may comprise a solvent (e.g., pharmaceutical quality water) and the receptacle(s) 62 may include a medicine-containing substance (e.g., a dry powder or concentrated suspension). A desired quantity of the solvent may be provided from the medical liquid source(s) 60 to one or more of the receptacle(s) 62 via the disposable 10 for mixing with the medicine containing substance to produce liquid medication of desired volume and concentration.

In another embodiment, the medical liquid source(s) 60 may comprise a bulk quantity of liquid medication to be provided in smaller quantities via the receptacle(s) 62 and the receptacle(s) 62 may be empty (e.g., void of medicine-containing substances and solvents). A desired quantity of the liquid medication may be provided from the medical liquid source(s) 60 to one or more of the receptacle(s) 62 via the disposable 10 to provide a liquid medication in a desired volume.

In yet another embodiment, the medical liquid source(s) 60 may comprise a bulk quantity of concentrated liquid medication and the receptacle(s) 62 may comprise a solvent. A desired quantity of the concentrated liquid medication may be provided from the medical liquid source(s) 60 to one or more of the receptacle(s) 62 via the disposable 10 to produce a liquid medication in a desired volume and concentration.

In yet another embodiment, the medical liquid source(s) 60 may comprise a plurality of liquid medications and the receptacle(s) 62 may be empty. In conjunction with the above-described optional manifold 64, selected amounts of one or more of the liquid medications in the medical liquid source(s) 60 may be compounded and provided to the receptacle(s) 62. Thus, in this embodiment, the filling system 1 may be operated as a compounder.

As noted above, the disposable 10 may be selectively engageable with the drive system 30. The drive system 30 may include a piston drive member 32, a valve drive member 34, one or more motor(s) 36 ("motor(s)") and a controller 50. The piston drive member 32 may be selectively interconnectable to the piston 14 of the disposable 10. More particularly, a first connection member 18 may be provided with the disposable 10 and a second connection member 31 may be provided with the drive system 30. The first connection member 18 may be interconnected to the seal member 16, which may be interconnected to the piston 14, and the second connection member 31 may be interconnected with the piston drive member 32, wherein the first and second connection members 18, 31 may be selectively interconnectable and disconnectable. Thus, the piston 14 may be selectively engaged and disengaged by the piston drive member 32, thereby facilitating selective interconnection and disconnection of the disposable 10 to and from the drive system 30.

The valve drive member 34 may be interconnectable to the valve 20 of the disposable 10 and the motor(s) 36 to facilitate positioning of the valve 20. In one embodiment, the valve drive member 34 may include one of at least a first projection and a first opening and the valve 20 may include the other one of at least the first projection and the first opening, where the first opening is adapted to receive the first projection to interconnect the valve drive member 34 to the valve 20. The valve 20 may alternatively be interconnected to the drive system 30 by other known means, such as via one or more gears.

The motor(s) 36 may be interconnected to drive the piston drive member 32 and/or the valve drive member 34 to facilitate movement of fluids through the system 1. For example, a first motor 36a (FIG. 2) may be interconnected to the piston drive member 32 via one or more belts 39 to facilitate movement of the piston drive member 32 in one or more directions (e.g., linearly forward and backward). A second motor 36b (FIG. 2) may be interconnected to the valve drive member 34 to facilitate movement of the valve drive member 34 in one or more directions (e.g., clockwise and/or counterclockwise) to position the valve 20 in at least first and second positions. Thus, the drive system 30 may be operable to change the position of the piston 14 (e.g., via piston drive member 34) and/or the valve 20 (e.g., via valve drive member 34) to facilitate selective movement of medical liquids into and out of the disposable 10. The motor(s) 36 may also be interconnected to the controller 50 to facilitate automated filling operations, as discussed in further detail below.

The drive system 30 may also be provided with a reference member and a sensor for sensing at least one degree of relative movement of the piston drive member 32, the sensor being operable to provide an output signal for use in determining a relative degree of retraction or advancement of the piston drive member 32. The amount the piston drive member 32 is advanced or retracted correlates to the amount of medical fluid drawn into or dispensed out of the disposable 10. Thus, the reference member and/or sensor may facilitate draw of and dispensing of selected amounts of fluids by sensing a plurality of degrees of relative movement and providing corresponding output signals, relating to each of the detected degrees of relative movement, to the controller 50. As discussed in further detail below, the controller 50 may process such output signals to determine a relative degree of movement of the piston drive member 34, and therefore, in relation to a known internal diameter of the tubular member 12, the amount of fluid drawn into and/or dispensed from the disposable 10. In the illustrated embodiment, the reference member and sensor are cooperatively combined and illustrated as position sensor 38. More detail regarding the position sensor 38 is provided below.

The controller 50 may be interconnected to the reference member and/or sensor (e.g., via the position sensor 38 or a rotary encoder 2108 discussed below) and/or the motor(s) 36. The controller 50 may be operable to receive signals from the sensor to assist in controlling the position of the piston drive member 32 and/or a rate and/or force of advancement and/or retraction of the piston 14. The controller 50 may also be operable to send signals to the motor(s) 36 to control one or more operating parameters of the motor(s) 36 (e.g., a direction, and/or rate of operation). For example, the controller 50 may control the first motor 36a (FIG. 2) to linearly advance and linearly retract the piston drive member 32. The controller 50 may also control the second motor 36b (FIG. 2) to drive the valve drive member 34 in a clockwise or counterclockwise, thereby positioning the valve 20 in at least one of the above-described first and second valve positions. More detail regarding the controller 50 is provided below.

To further facilitate automated filling of medical liquids, a user interface 70 may be interconnected to the controller 50, the user interface 70 being operable receive input and to provide parameters to the controller 50 to facilitate automation of the filling system 1. For example and as described in detail below, the user interface 70 may be operable to accept input and communicate parameters associated with a fill-related valve (e.g., a desired quantity of receptacle(s) 62 to be filed and the amount of medical liquid to be dispensed to each of the receptacle(s) 62). Thus, the user interface 70 may facilitate automatic or semi-automatic operation of the filling system 1. More detail regarding the user interface 70 is provided below.

Referring now to FIGS. 3a-3d, one embodiment of a disposable 10 useful in accordance with the present invention is now described. Specifically with reference to FIGS. 3a and 3c, the disposable 10 may include a tubular member 12, a piston 14 and a seal member 16. The tubular member 12 may include first, second and/or third portions, 12a, 12b and 12c, respectively, the first portion 12a having a first internal diameter D1, the second portion 12b being located distal to the first portion 12a and having a second internal diameter D2, and a third portion 12c being located distal to the second portion 12b and having a third internal diameter D3. In the illustrated embodiment, the second diameter D2 is greater than the first diameter D1 and the third diameter D3 is greater than the second diameter D2. As discussed in further detail below, utilizing varying diameters may facilitate increasing the useful lifetime of the disposable 10.

Referring now to FIGS. 3c, 3d and 4a-4d, the piston 14 may include a first resilient member 15 adapted to sealably engage an internal surface of the tubular member 12 when disposed within the first portion 12a of the tubular member 12 (e.g., ring-shaped and peripherally disposed). That is, the first resilient member 15 may comprise a diameter at least as large as the first diameter D1 of the first portion 12a of the tubular member 12. Thus, fluids may be drawn into the tubular member 12 upon retraction of the piston 14, and fluids may be dispensed from the tubular member 12 upon advancement of the piston 14.

The seal member 16 may be fixedly interconnected to the tubular member or may be slidably disposed therein for co-movement with the piston 14. The seal member 16 may include a second resilient member 17 adapted to sealably engage an internal surface of the tubular member 12 when disposed within the second portion 12b of the tubular member 12 (e.g., ring-shaped and peripherally disposed). That is, the second resilient member 17 may comprise a diameter at least as large as the second diameter D2 of the second portion 12b of the tubular member 12. Thus, the seal member 16 may restrict entry of outside substances (e.g., air, particles, etc.) into the tubular member 12 during operation of the automated medical liquid filling system 1 by sealing distal portions of the tubular member 12.

Furthermore, as the seal member 16 may interact with outside fluids (e.g., air), it is not desirable for the seal member 16 to fluidly communicate with the portion of the tubular member 12 that fluidly communicates with medical fluids. Thus, in one embodiment of the present invention, the seal member 16 is interconnected to the piston 14 (e.g., by rod 13) and spaced therefrom by a fixed distance that is at least as great as a length of the first portion 12a of the tubular member 12. In a particular embodiment and with reference to FIG. 4d, the seal member 16 is spaced from the piston 14 by a fixed distance 12d that is greater than a length of the first portion 12a of the tubular member 12. Therefore, the seal member 16 may be restricted from being located within the first portion 12a of the tubular member 12, thereby reducing the possibility of contamination of the first portion 12a of the tubular member 12.

Figure 4A:
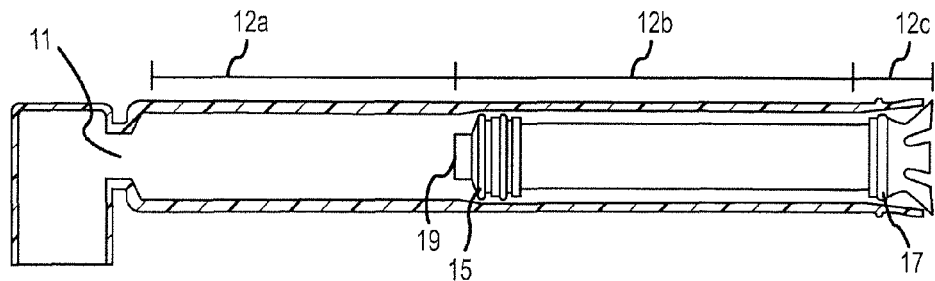
FIG. 4a is a side view of a disposable illustrating a piston positioned in a fully retracted position.
Figure 4B:
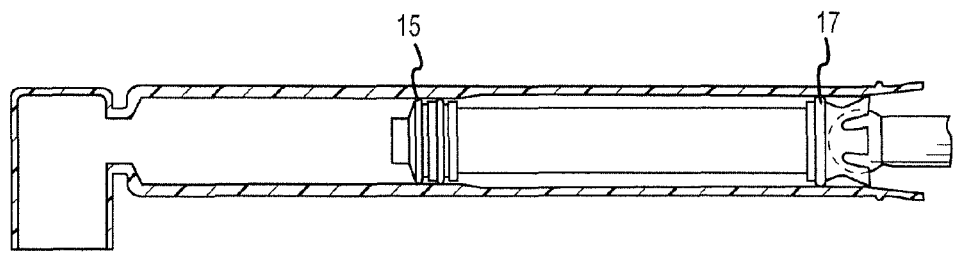
FIG. 4b is a side view of a disposable illustrating a piston positioned in a home retracted position.
Figure 4C:
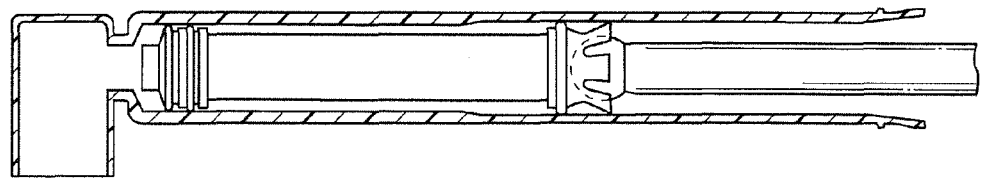
FIG. 4c is a side view of a disposable illustrating a piston positioned in a home advanced position.
Figure 4D:
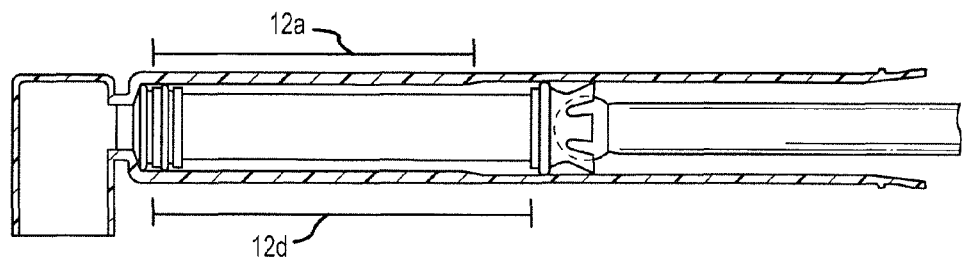
FIG. 4d is a side view of a disposable illustrating a piston positioned in a fully advanced position.
Figure 5A:
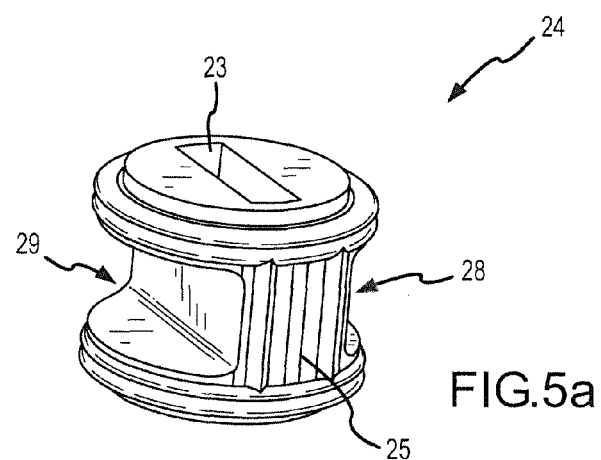
Figure 5B:
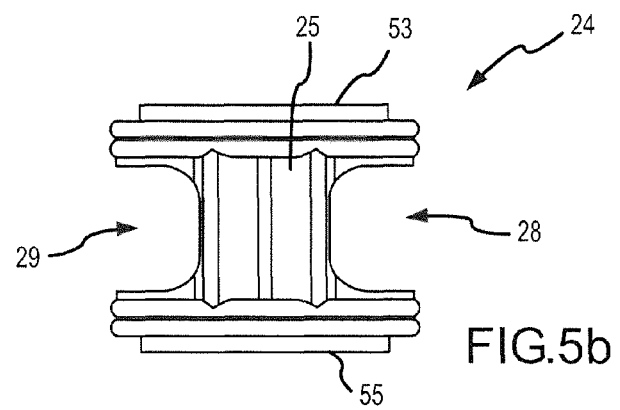
Figure 5C:
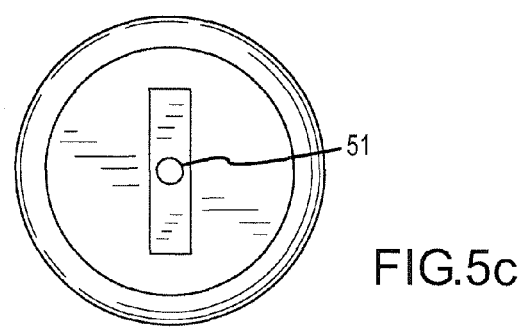

As noted above and with continued reference to FIGS. 3c, 3d and 4a-4d, the tubular member 12 may include first, second and third diameters D1, D2, D3. Utilizing such increasing diameters within the tubular member 12 may assist in increasing the expected useful lifetime of the disposable 10. In this regard, the first resilient member 15 may comprise a diameter that is at least as large as the first diameter D1. In one embodiment, the diameter of the first resilient member 15 may also be not greater than a diameter of the second portion 12b of the tubular member 12 (e.g., the second diameter D2). Thus, when the first resilient member 15 is positioned within the second portion 12b of the tubular member 12, as illustrated in FIG. 4a (e.g., when the piston is in a fully retracted position), the first resilient member 15 may be expanded (e.g., decompressed/in a less compressed state) relative to when the first resilient member 15 is positioned in the first portion 12a of the tubular member 12, as illustrated in FIG. 4b. In a particular embodiment, at least a portion of the first resilient member 15 may be free from compressive engagement with the tubular member 12 when the first resilient member 15 is positioned within the second portion 12b of the tubular member 12. Thus, when the first resilient member 15 is located within the second portion 12b of the tubular member 12 (e.g., prior to use), it may be only slightly compressed or free from compression. Therefore, the lifespan of the first resilient member 15, and thus the disposable 10, may be increased.

Similarly, the second resilient member 17 may comprise a diameter that is at least as large as the second diameter D2. In one embodiment, the diameter of the second resilient member 17 may be not greater than a diameter of the third portion 12c of the tubular member 12 (e.g., the third diameter D3). Thus, when the second resilient member 17 is positioned within the third portion 12c of the tubular member 12, as illustrated in FIG. 4a, the second resilient member 17 may be expanded (e.g., decompressed/in a less compressed state) relative to when the second resilient member 17 is positioned in the second portion 12b of the tubular member 12, as illustrated in FIG. 4b. In a particular embodiment, at least a portion of the second resilient member 17 may be free from compressive engagement with the tubular member 12 when the second resilient member 17 is positioned within the third portion 12c of the tubular member 12. Thus, when the second resilient member 17 is located within the third portion 12c of the tubular member 12 (e.g., prior to use), it may be only slightly compressed or free from compression. Therefore, the lifespan of the 17, and thus the disposable 10, may be increased.

Figure 18:
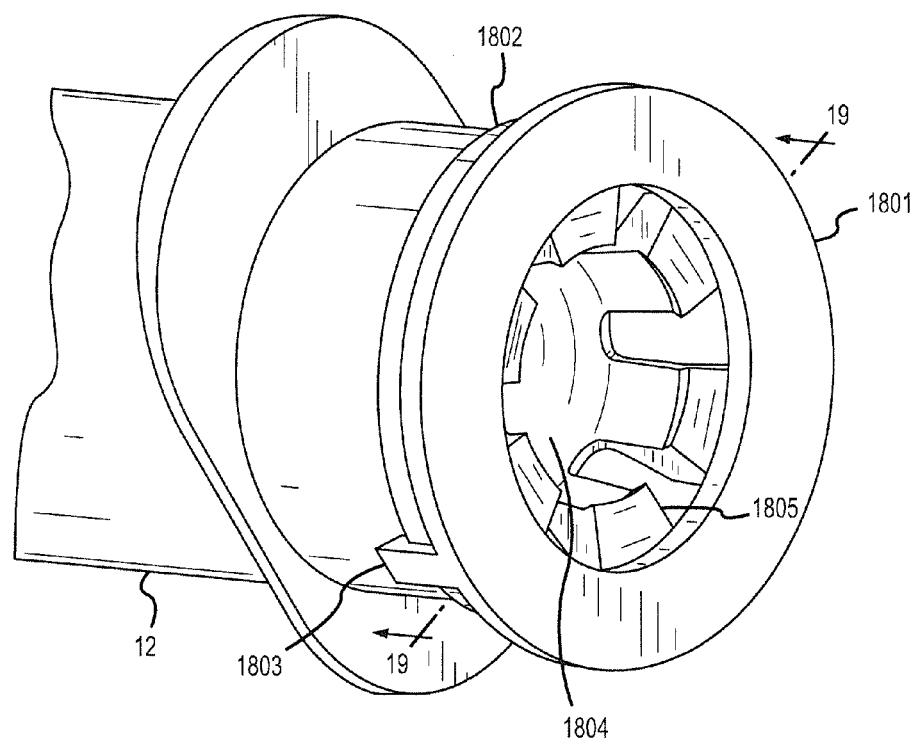
FIG. 18 is a perspective view of a distal end of one embodiment of a connection member within a tubular member and a snap ring.

Turning to FIG. 18, a snap ring 1801 may be placed over the end of the tubular member 12. The snap ring 1801 may prevent the piston 14 (not shown in FIG. 18) and seal member 1804 assembly from exiting the tubular member 12. The snap ring 1801 may have one or more snaps 1803 that engage a feature, such as a rib 1802 on the tubular member 12. The one or more snaps 1803 may be operable to provide for a relatively low insertion force to place the snap ring 1801 onto the tubular member 12 and provide for a relatively high removal force to remove the snap ring 1801 from the tubular member 12. The inner diameter of the snap ring 1801 may be less than the maximum outer diameter of the seal member 1804, thereby preventing the seal member 1804 from exiting the tubular member 12. Accordingly, the snap ring 1801 may provide the benefit of preventing the piston 14 and the seal member 1804 from inadvertently exiting the tubular member 12 during, for example, shipping and handling of the disposable 10.

Figure 3A:
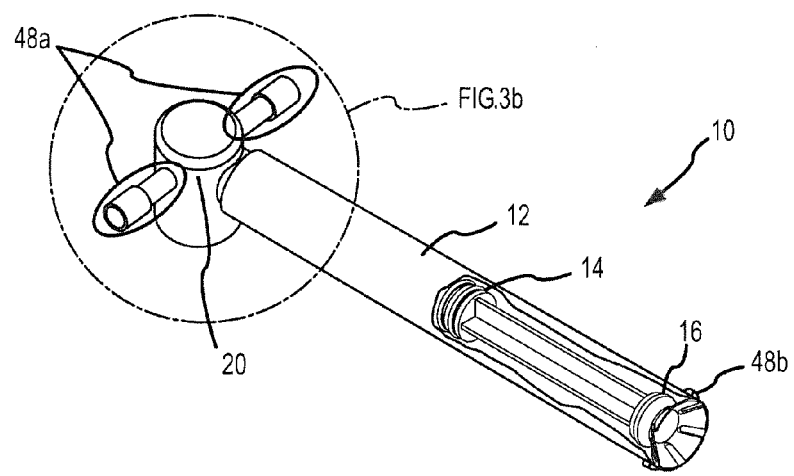
FIG. 3a is a perspective view of one embodiment of a disposable of FIGS. 1-2.

The tubular member 12 may include any number of diameters and such diameters may correspond to any shape. For example, the tubular member 12 may comprise a cylinder having a single diameter. The tubular member 12 may comprise two or more adjacent cylinders having differing diameters. The tubular member 12 may comprise a cylinder and an ellipsoid and/or other structures, each having different or similar diameters. Moreover, the tubular member 12 may be a unitary structure or may be formed from two or more structures, such as two cylinders having differing diameters, which are fused together. Also, the diameters may decrease in size from the distal end to the proximal end of the tubular member 12, as illustrated in FIG. 3a, or the diameters may increase in size from the distal end to the proximal end of the tubular member 12, or varying diameters may be used, wherein the diameters may increase, then decrease, then increase, as appropriate, and vice-versa. Correspondingly, disposables of differing size may be utilized with the filling system 1, depending on application. For example, a disposable 10 having a tubular member 12 with a relatively large diameter may be used in high volume, low pressure filling applications. A disposable 10 having a tubular member 12 with a relatively small diameter may be utilized in low volume, high pressure filling applications.

Additionally, the first resilient member 15 may comprise a shape corresponding to the shape of the second portion 12b, wherein at least a portion of the first resilient member is expanded relative to when that portion of the first resilient member 15 is positioned in the first portion 12a of the tubular member 12. For example, the second portion 12b may comprise a cylinder shape and the first resilient member may comprise an ellipsoidal shape, wherein portions of the first resilient member are free from compressive engagement with the second portion 12b, and other portions of the first resilient member are compressively engaged with such second portion 12b. The second resilient member 17, third portion 12c and second portion 12b may also be similarly arranged.

Figure 17:
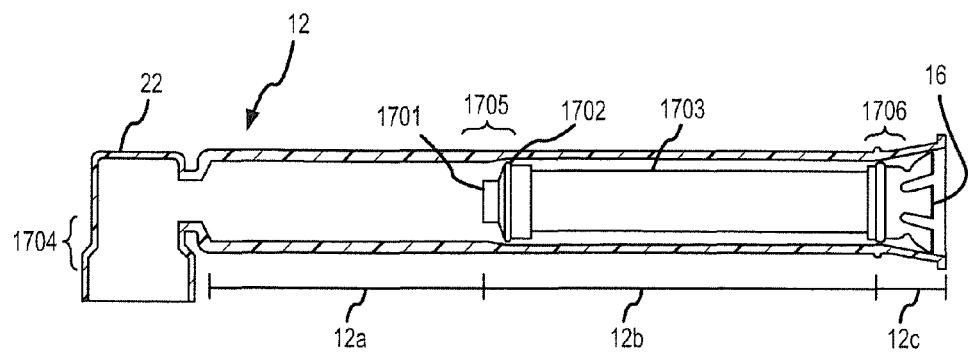
FIG. 17 is a side view of one embodiment of a disposable illustrating an overmolded piston with a single seal positioned in a fully retracted position.

Another embodiment of the disposable 10 is illustrated in FIG. 17. As illustrated in FIG. 17, a piston 1701 may include a single seal portion 1702. The piston 1701 and the single seal portion 1702 may be a single unitary part comprised of a single type of material. The material may, for example, be a thermoplastic material (e.g., polyurethane). The piston 1701, including the single seal portion 1702, may be manufactured by overmolding onto the rod 1703. For example, the rod 1703 may be placed in a mold for the piston and located within the cavity of the mold and polyurethane may then be flowed into the cavity to form the piston 1701, including the single seal portion 1702, directly onto the rod 1703. The piston 1701, including the single seal portion 1702, may preferably have a durometer hardness of below 90 A. More preferably, the durometer hardness may be about 70 A.

The single seal portion 1702 may experience compression when the piston 1701 is located within the first portion 12a of the tubular member 12. During dispensing, a positive pressure may be created within the portion of the tubular member 12 that contains liquid being dispensed relative to the portion of the tubular member 12 that does not contain liquid. During liquid drawing, a negative pressure may be created within the portion of the tubular member 12 that contains liquid being drawn relative to the portion of the tubular member 12 that does not contain liquid. Preferably, the amount of interference between the single seal portion 1702 and the tubular member 12 is operable to prevent leakage between the portion of the tubular member 12 that contains liquid and the portion of the tubular member 12 that does not contain liquid when the pressure differential between the two portions (i.e., opposite sides of the single seal portion 1702) is between 0 and 45 psi. More preferably, the amount of interference is operable to prevent leakage when the pressure differential is between 0 and 60 psi.

The ability of the single sealing portion 1702 to prevent the aforementioned leakage when a pressure differential is present can be increased or decreased from the aforementioned values. Generally, as the ability of the system to seal against pressure differentials is increased, the frictional forces between the single sealing portion 1702 and the tubular member 12 will also increase and as the ability of the system to seal against pressure differentials is decreased, the frictional forces between the single sealing portion 1702 and the tubular member 12 will also decrease. A preferred range of interference between the diameter of the single seal portion 1702, constructed of polyurethane with a durometer hardness of about 70 A, and the first portion 12a of the tubular member 12 is between 0.012 inches and 0.024 inches.

A lubricant may be applied to the disposable 10. The lubricant may reduce frictional forces between the valve stem 24 and the valve housing 22. In this regard, the lubricant may initially be applied annularly around an inside diameter in the area 1704 of the transition between the first housing diameter and the second housing diameter of the valve housing 22. The lubricant may reduce frictional forces between a piston (e.g., the piston 14 and resilient member 15 of FIGS. 2, 3b, and 3d, and the piston 1701 and single seal portion 1702 of FIG. 17) and the tubular member 12. Accordingly, the lubricant may initially be applied annularly around an inside diameter in the area 1705 of the transition between the first portion 12a and the second portion 12b of the tubular member 12. The lubricant may reduce frictional forces between the second resilient member 17 and the tubular member 12. In this regard, the lubricant may initially be applied annularly around an inside diameter in the area 1706 of the transition between the second portion 12b and the third portion 12c of the tubular member 12. Although the placement of the lubricant is described with respect to FIG. 17, the lubricant may similarly be applied to other embodiments described herein (e.g., the embodiments of FIGS. 4a-4d). The lubricant may also serve to increase the working life of the various components it contacts.

It may be desirable to distribute the lubricant throughout its operational range during the initial assembly process of the disposable 10. Accordingly, the lubricant may initially be placed in an annular ring around the inside diameter in the aforementioned areas 1704, 1705, and 1706. The lubricant may be pneumatically applied. The piston 1701, interconnected to the rod 1703 and seal member 16, may then be inserted into the tubular member 12. The snap ring 1801, previously described, may then be attached to the tubular member 12. The piston 1701 may then be moved through substantially its entire operational range (e.g., between the fully retracted position and the fully advanced position) one or more times to distribute the lubricant. In a similar fashion, the valve stem 24 may be fully inserted into the valve housing 22 and removed from the fully inserted position one or more times to distribute lubricant within the valve housing 22. The disposable 10 may then be tested as described hereinbelow. After testing, the piston 1701 may be moved to the fully retracted position and remain in such a position, including during periods of storage and shipping, until the disposable 10 is utilized by an end user. Similarly, the valve stem 24 may be moved into the area of the second housing diameter of the valve housing 22 and remain in such a position, including during periods of storage and shipping, until the disposable 10 is utilized by an end user.

The lubricant is preferably a non-self-leveling lubricant. In a preferred embodiment, the lubricant may have a viscosity of at least 12,500 centistokes (cS). The lubricant may be a silicone grease, such as for example, Nu-Sil MED-9031 silicone grease, which has a viscosity of about one million cS, marketed by Nu-Sil Silicone Technology, California, U.S.A.

As noted above and with reference to FIGS. 3a and 3b, the disposable 10 may also include a valve 20. The valve 20 may include the valve housing 22 interconnected to the tubular member 12 (e.g., at a proximal end of the tubular member 12) and a valve stem 24 disposed within the valve housing 22. The valve 20 may further include a plurality of ports, such as a first valve port 26 and a second valve port 27. The first valve port 26 may be fluidly interconnected to the tubular member 12 when the valve 20 is in a first valve position and the second valve port 27 may be fluidly interconnected to the tubular member 12 when the valve 20 is in a second valve position. The first valve port 26 may be fluidly interconnected to the first fluid line 80, which may be fluidly interconnected to the medical liquid source(s) 60. The second valve port 27 may be fluidly interconnected to the second fluid line 82, which may be fluidly interconnected to the receptacle(s) 62. Thus, when the valve 20 is positioned and maintained in the first valve position fluids from the medical liquid source(s) 60 may be drawn into the tubular member 12 via the first valve port 26 and first fluid line 80, and when the valve 20 is positioned and maintained in the second valve position, fluids in the tubular member 12 may be dispensed to the receptacle(s) 62 via the second valve port 27 and the second fluid line 82. As the first and second ports 26, 27 are fluidly interconnected to the tubular member 12, they share a common port (e.g., a port located at the proximal end of the tubular member 12), and thus medical liquids may flow in and out of a common port of the tubular member 12.

One embodiment of a valve stem 24 is now described in reference to FIGS. 3b and 5a-5c. The valve stem 24 may include at least a first opening 23 and the first opening 23 may be adapted to receive a first projection 35 of the valve drive member 34. In one embodiment, the valve stem 24 includes at least first and second channels 28, 29, the channels 28, 29 being fluidly isolated from one another when the valve stem 24 is disposed within the valve housing 22. In a particular embodiment, the first and second channels 28, 29 may be disposed in an offset manner about a perimeter of the valve stem 24. In a related embodiment, the first and second channel 28, 29 may comprise separate, arcuate paths. In a further embodiment, the valve stem perimeter may be defined in part by the first and second channels 28, 29.

When the valve stem 24 is disposed within the valve housing 22, the first channel 28 may be fluidly interconnectable to the first port 26 and the second channel 29 may be fluidly interconnectable to the second port 27. More particularly, the first channel 28, the first valve port 26 and the tubular member 12 may only be fluidly interconnected when the valve 20 is in the first valve position. The second channel 29, the second valve port 27 and the tubular member 12 may only be fluidly interconnected when the valve 20 is in the second valve position. Thus, in this embodiment, there is no cross communication between the first and second channels 28, 29 as the tubular member 12 only communicates with a single channel for any given valve position. Restricting cross communication between the channels may restrict contamination of the medical liquid source(s) 60 and/or the receptacle(s) 62 and may restrict unimpeded flow of medical fluids through the system 1.

The valve stem 24 may also include a stop portion 25. When the valve 20 is in a third valve position (e.g., a neutral position), the stop portion 25 may restrict fluid communication between the first valve port 26 and the tubular member 12. Further, when the valve 20 is in the third valve position, the stop portion 25 may restrict fluid communication between the second valve port 27 and the tubular member 12. Thus, in the third valve position, fluids are restricted from flowing into and out of the tubular member 12. As may be appreciated, this third valve position and corresponding stop portion 25 may be useful in a variety of circumstances, such as to prevent contamination of the tubular member 12 during shipping of the disposable 10.

The valve stem 24 may also be shipped in a less compressed state. Referring now to FIG. 3a, the valve housing 22 may include a first housing portion having a first housing diameter H1 and a second housing portion having a second housing diameter H2, the first housing diameter H1 being larger than the second housing diameter H2. The valve stem 24 may be positioned and shipped within the first housing portion. Upon interconnection of the disposable 10 with the mount 40, the valve stem 24 may be positioned within the second housing portion (e.g., via the valve drive member 34). Thus, the valve stem 24 may be shipped in a less compressed state to facilitate increasing the useful lifetime of the disposable 10. To avoid trapping gas within the valve housing 22, between the valve stem 24 and the valve housing 22 as the valve stem 24 is moved from the first housing portion to the second housing portion, the valve stem may have a vent hole 51 between a top surface 53 and a bottom surface 55 of the valve stem 24. As with the tubular member 12, the valve housing 22 may be of any shape, have any number of diameters, which may increase, decreases or both, throughout the valve housing 22, and may be a unitary structure or may be comprised of two or more components. Relatedly, and as noted, the valve housing 22 may be integral with the tubular member 12 or may be a separate component adapted for engagement with the tubular member 12. As noted, the optional manifold 64 may be utilized in conjunction with the valve 20 to distribute fluids in the filling system 1. Thus, the optional manifold 64 may also be integral with the valve 20 and/or tubular member 12, or may be a separate component.

The first and second fluid lines 80, 82 may be interconnected immediately prior to use, such as at the administration facility (e.g., a hospital) or may be interconnected during manufacture of the disposable 10. In this regard, the disposable 10 may be shipped with the first and second fluid lines 80, 82 interconnected to the disposable 10. The first and/or second fluid lines 80, 82 may be shipped with a connector (e.g., a luer or spike connector), which may be sealed in a sterile sheath or with a cap. The first and/or second fluid lines 80, 82 may be shipped with other devices such as, for example, one or more Y connectors, fluid bags, valves, additional tubing and nozzles. Furthermore, the disposable 10 may include the piston 14 oriented in a shipping position (e.g., the above-described fully retracted position), and the valve 20 oriented in a shipping position (e.g., the above-described third valve position) and/or with the valve 20 positioned in the first portion of the valve housing 22. Also, the disposable 10 may be packaged in a sterile condition. For example, the disposable 10, and any interconnected components, may be assembled, packaged in a heat-sealed enclosure, and sterilized via exposure to gamma radiation at an assembly location. The disposable 10 may be transferred to another location, remote from the assembly location, where it may be removed from the enclosure and utilized.

Figure 6:
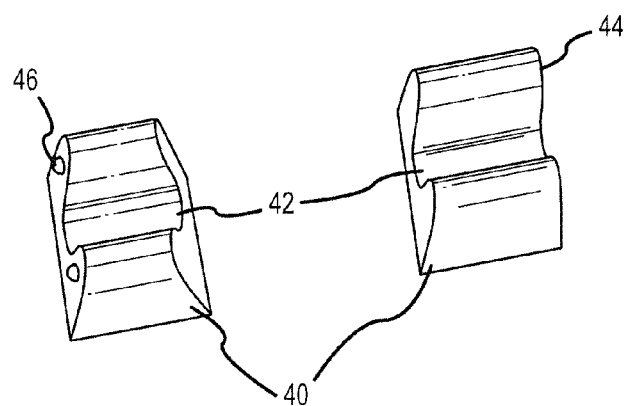
FIG. 6 is a perspective view of one embodiment of a mount of FIGS. 1-2.

Referring now to FIG. 6, a mount 40 may be provided with the drive system 30. The mount 40 may include an engagement surface 44 and a bearing portion 46. The mount 40 may also include a cradle portion 42 adapted to receive a portion of the tubular member 12. The disposable 10 may include a first flange for engaging the bearing portion 46 and a second flange for engaging the engagement surface 44.

Figure 3B:
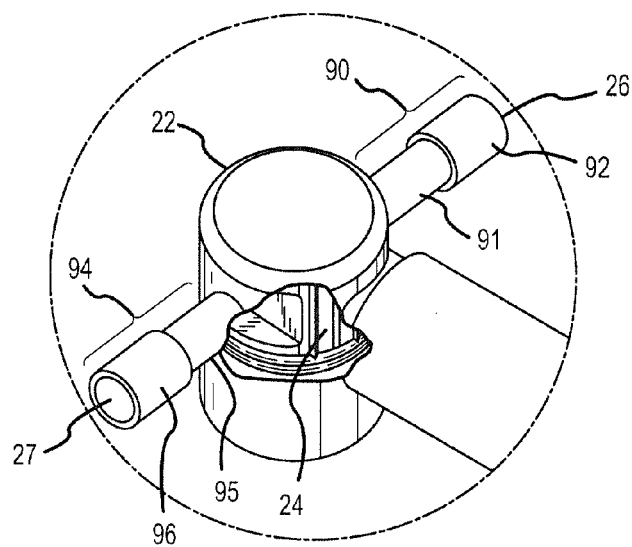
FIG. 3b is a perspective view of a portion of the disposable of FIG. 3a with a portion cut away to show internal features.
Figure 3C:
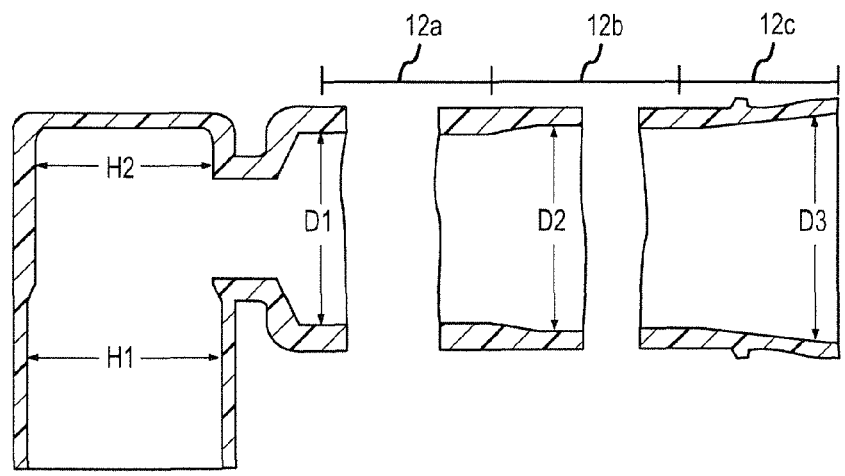
Figure 3D:
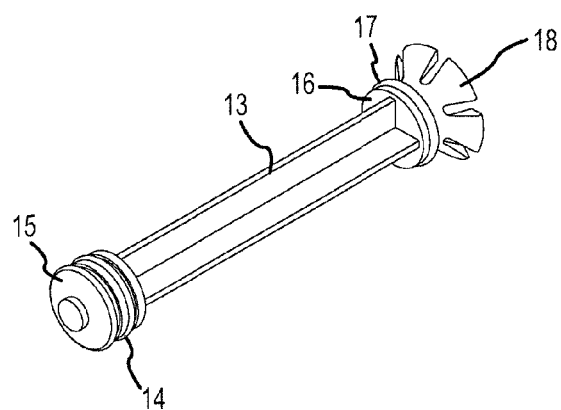
FIG. 3d is a side view of the piston of FIG. 3a interconnected to a seal member.

More particularly and with reference to FIGS. 3a and 3b, a first flange 48a of the disposable 10 may include first and second stems 90, 94 fixedly interconnected to the valve housing 22. The first stem 90 may include a first portion 91 interconnected to the valve housing 22 and a second portion 92 interconnected to the first portion 91 and the first valve port 26. A passageway may be disposed within the first and second portions 91, 92 to facilitate fluid interconnection of the first valve port 26 to the valve stem 24.

The second stem 94 may include first and second portions 95, 96. The first portion 95 may be interconnected to the valve housing 22 and the second portion 96 may be interconnected to the first portion 95 and the second valve port 27. A passageway may be disposed within the first and second portions 95, 96 to facilitate fluid interconnection of the second valve port 27 to the valve stem 24.

The first portions 91, 95 may be adapted for selective and restrictive engagement with the mount 40. In this regard and with reference to FIGS. 3b and 6, the first portions 91, 95 may be adapted to restrictively engage the bearing surface 46 of the mount 40 (e.g., the proximal portion of the bearing surface 46). Thus, the proximal portion of the mount 40 may be adapted to selectively and restrictively engage the disposable 10 to restrict movement of the disposable 10 in at least a first direction (e.g., a relative up and down direction). The cradle 42 of the mount 40 may be further adapted to receive at least a portion of the tubular member 12 to restrict movement of the disposable 10 in a second direction (e.g., a relative side-to-side direction). Additionally, the second portions 92, 96 may be larger than the first portions 91, 95 so as to facilitate interconnection of the first and second valve ports 26, 27 with the first and second fluid lines 80, 82, respectively.

As noted above, the disposable 10 may include a second flange portion that may engage the mount 40. More particularly and with reference to FIGS. 7a-7b and 8, the mount 40 may include an engagement portion 44 for engaging the second flange 48b of the disposable 10, the second flange 48b being fixedly interconnected to the tubular member 12 and located distal to the first flange 48a. In this regard, the engagement surface 44 may be located near a distal end of the mount 40 and include a non-planar (e.g., a concave) surface adapted for interfacing with the second flange portion 48b. The second flange portion 48b may include a corresponding non-planar portion (e.g., a similar concave portion) adapted for engagement with the non-planar portion of the engagement surface 44.

Moreover, the mount 40 may include a proximal face and a distal face spaced a first distance from each another. The first and second flanges 48a, 48b may be spaced a second distance from each other, such that, upon interconnection with the bearing portion 46 and engagement portion 44, the first flange 48a abuts the proximal side of the proximal face and the second flange 48b abuts the distal side of the distal face, thereby restricting movement of the disposable in a third direction (e.g., a relative front-to-back direction). Therefore, upon interconnection to the mount 40, the tubular member 12 of the disposable 10 may be restricted from movement in three dimensions.

Figure 7A:
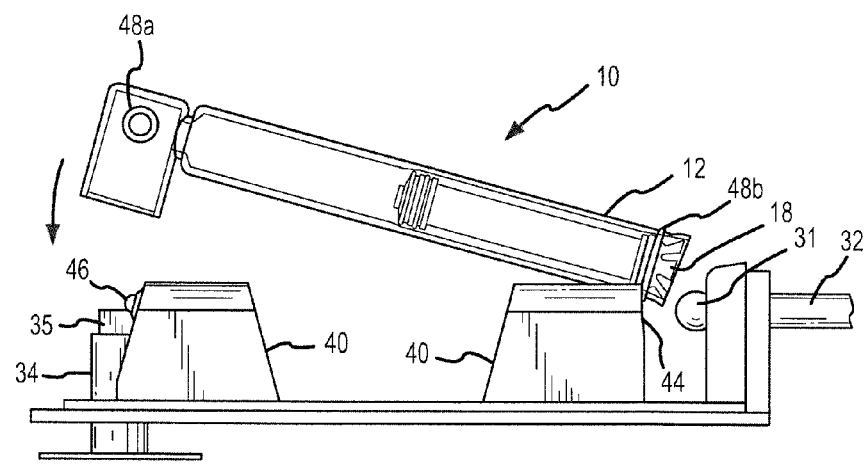
FIG. 7a is a side view of one embodiment of a step utilized to interconnect the disposable of FIG. 3a to the mount of FIG. 6.
Figure 7B:
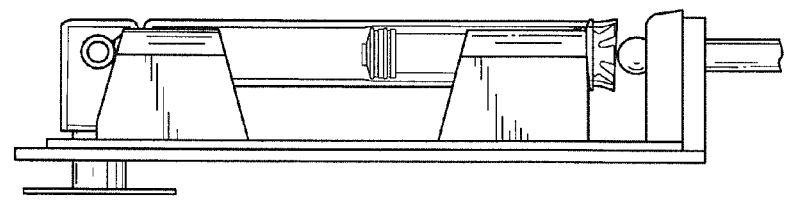
FIG. 7b is a side view of one embodiment of the disposable of FIG. 3a interconnected to a mount of FIG. 6.

With reference now to FIGS. 7a-7b, to interconnect the disposable 10 to the mount 40, the tubular member 12 may be aligned with the cradle 42 (not shown), the second flange portion 48b may be aligned with the engagement portion 44, and the proximal end of the disposable 10 may be at a higher relative position than the distal end of the disposable 10. The second flange portion 48b may then be interconnected to the engagement portion 44 of the mount 40 to interconnect the distal end of the disposable 10 to the mount 40. The proximal end of the disposable 10 may then be lowered (e.g., pushed down) so as to engage the first flange portion 48a with the bearing surface 46. Upon application of sufficient downward force, the first flange portion 48a may slide down and past the bearing surface 46 and the tubular member 12 may contact the cradle 42 (not shown), thereby restrictively engaging the disposable 10. As may be appreciated, the disposable 10 may be disengaged from the mount 40 by application of sufficient upward force to slide the first flange 48a past the bearing surface 46. Thus, the flanges 48a and 48b, tubular member 12, cradle 42, engagement surface 44 and/or bearing surface 46 may enable the selective engagement and disengagement of the disposable 10 with the mount 40 (e.g., via snap and lock action), therefore facilitating placement and removal of the disposable 10 with and from the drive system 30. Of note, during engagement of the proximal end of the disposable 10 with the mount 40, the first opening of the valve stem 24 may engage the first projection 35 of the valve drive member 34.

Other methods of restrictively interconnecting the disposable 10 to the mount 40 may also be utilized. For example, a lock, clamp, strap or other mechanical means may be utilized to restrictively interconnect the disposable 10 to the mount 40. Also, electromagnetic means may be utilized to interconnect the disposable 10 to the mount 40, such as with the use of one or more magnets on the exterior of a portion of the disposable 10 and the mount 40.

Referring back to FIGS. 1-2, upon interconnection of the disposable 10 to the mount 40, the piston drive member 32 may interconnect with the piston 14. As noted above, the first and second connection members 18, 31 may be utilized to facilitate the interconnection of the piston drive member 32 and the piston 14. More particularly, when the first and second connection members 18, 31 are collocated within the tubular member 12 (e.g., in or between the home retracted position and the fully advanced position, described below), the piston 14 and piston drive member 32 may be restrainably interconnected to facilitate co-movement of the piston 14 with the piston drive member 32. When the first and second connection members 18, 31 are not collocated within the tubular member 12 (e.g., in a shipping or fully retracted position, described below), the first connection member 18 may disengage the second connection member 31. Thus, the first and second connection members 18, 31 may interconnect the piston 14 with the piston drive member 32 to facilitate co-movement when the piston 14 is positioned within proximal portions of the tubular member 12, and the first and second connection members 18, 31 may disconnect when the piston 14 is positioned in distal portions of the tubular member 12. Thus, the first and second connection members 18, 31 may facilitate selective interconnection of the piston 14 and the piston drive member 32 and co-movement thereof.

To achieve interconnection between the first and second connection members 18, 31, the piston drive member 32 may be advanced to push the first and second connection members 18, 31 into the tubular member 12 so that they are collocated within the tubular member 12. To disconnect the first and second connection members 18, 31, the piston drive member 32 may be retracted to withdraw at least a portion of the first and second connection members 18, 31 from the tubular member 12 so they are not collocated within the tubular member 12.

Figure 8:
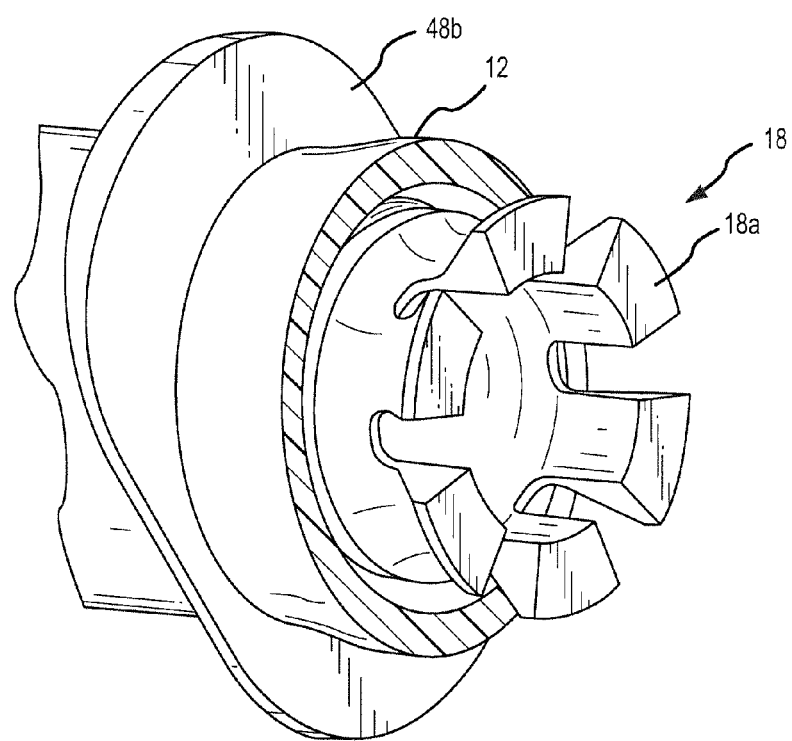
FIG. 8 is a perspective view of one embodiment of a connection member of the disposable of FIG. 3a with a portion of the distal end of the tubular member cut away.

In a particular embodiment and with reference to FIGS. 7a-7b and FIG. 8, the first connection member 18 may include a complimentary female member and the second connection member 31 may include a complimentary male member, the male member being insertable into and restrainably engaged by the female member when the connection members 18, 31 are collocated within the tubular member 12. In this regard, the female member may comprise a plurality of fingers 18a ("fingers") separated at their distal ends and the male member may comprise a coincidentally-shaped/sized bulbous end portion. The fingers 18a of the female portion may be adapted to at least partially receive, in an opening defined between the fingers 18a, the bulbous end portion of the male member and the fingers 18a may be collapsible/articulatable/pivotable to envelope and thereby restrainably engage (e.g., grip) the bulbous end portion when the connection members 18, 31 are located in a first position (e.g., a first portion of the tubular member 12). The fingers 18a of the female portion may also be sufficiently resilient to release the bulbous end portion when the connection members 18, 31 are located in a second position (e.g., outside of the tubular member 12 or in another portion of the tubular member 12).

In a particular embodiment, when the fingers 18a and bulbous end portion are not collocated within the tubular member 12 (e.g., in a fully retracted position), the fingers 18a may be in a relaxed position such that the fingers 18a do not restrainably engage the bulbous end portion. Conversely, when the fingers 18a and the bulbous end portion are collocated within the tubular member 12, the fingers 18a may be in a compressed position, where at least a distal portion of the fingers 18a restrainably engage the bulbous end portion of the male member. As may be appreciated, the first connection member 18 may alternatively comprise the male member and the second connection member 31 may comprise the female member.

The piston drive member 32 may be any member adapted to advance and retract the piston 14. For example, the piston drive member 32 may comprise a rod, as illustrated in FIG. 2. Alternatively, the piston drive member may comprise a lead screw of one of the motor(s) 36. The motor(s) 36 may also be one or more of a rotational motor (e.g., a brushless DC motor) or a non-rotational motor (e.g., a linear motor).

Figure 19:
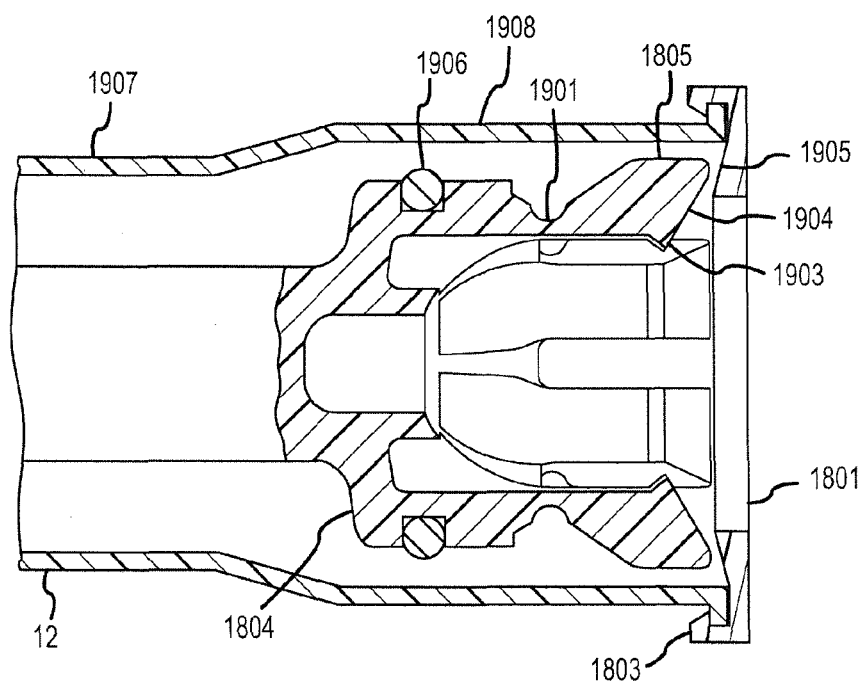
FIG. 19 is a partial cross sectional side view of the embodiment of FIG. 18.

In a particular embodiment and with reference to FIGS. 18 and 19, the seal member 1804 may comprise a plurality of fingers 1805 for interconnection with a bulbous end portion of a male member (not shown in FIGS. 18 and 19) similar to those discussed above with reference to the FIG. 8. However, in the embodiment illustrated in FIGS. 18 and 19, the plurality of fingers 1805 further comprise inward protrusions 1903 and angled end portions 1904. The inward protrusions 1903 may be operable to increase the grip strength (relative to an embodiment not including the plurality of inward protrusions 1903) of the plurality of fingers 1805 on the bulbous end portion when the plurality of fingers 1805 and the bulbous end portion are co-located in the first portion 1907 of the tubular member 12. The increase in grip strength may be due to a greater percentage of the surface of the bulbous end portion being surrounded by the plurality of fingers 1805, thus requiring a greater deformation of components for the bulbous end portion to become disengaged from the plurality of fingers 1805 while the bulbous end portion and the plurality of fingers 1805 are co-located in the first portion 1907 of the tubular member 12.

To disengage the bulbous end portion from the plurality of fingers 1805, the bulbous end portion may be retracted away from the tubular member 12. During this retraction, the plurality of fingers 1805 may be moved into the second portion 1908 of the tubular member 12 wherein the plurality of fingers 1805 may be in a relaxed position as illustrated in FIG. 19. As the bulbous end member is drawn out of tubular member 12, the plurality of fingers 1805 may come in contact with the snap ring 1801. As the bulbous end portion is continued to be withdrawn from the tubular member 12, the bulbous end portion may impart a force on the interior side of the plurality of inward protrusions 1903 that may act to outwardly spread the plurality of fingers 1805, thus releasing the bulbous end portion from the grip of the plurality of fingers 1805. To further assist the process of spreading of the plurality of fingers 1805 to release the bulbous end portion, the plurality of fingers 1805 may comprise angled end portions 1904 and the snap ring 1801 may comprise a complimentary angled portion 1905. Accordingly, when the angled end portions 1904 meet the angled portion 1905 of the snap ring 1801, the angle of the angled end portions 1904 and of the angled portion 1905 along with the force imparted on the plurality of fingers 1805 by the bulbous end portion as it is pulled out of the tubular member 12 may further tend to spread the plurality of fingers 1805. In this regard the angled end portions 1904 and the angled portion 1905 of the snap ring 1801 serve to reduce the force required to remove the bulbous end portion from the grip of the plurality of fingers 1805.

To engage the bulbous end portion with the seal member 1804, the bulbous end portion may be advanced into the tubular member 12. During this movement, the seal member may be moved toward the second portion 1907 of the tubular member 12 as the bulbous end portion interacts with the inward protrusions 1903 of the plurality of fingers 1805. Once an o-ring 1906 comes in contact with the first portion 1907 of the tubular member 12, a significant resistive force to the inward movement of the bulbous end portion may be present. At this point, as the bulbous end portion is further advanced, the bulbous end portion may cause the plurality of fingers 1805 to spread open so that the bulbous end portion can then move past the inward protrusions 1903 and fully engage with the seal member 1804. This sequence may be achieved by configuring the seal member 1804 so that the resistive force to movement of the seal member 1804 when the o-ring 1906 of the seal member 1804 is located within the first portion 1907 of the tubular member 12 is greater than the resistance of the plurality of fingers 1805 to being spread open by the bulbous end portion interacting with the inward protrusions 1903. This configuration may be achieved by selecting a proper thickness of the seal member 1804 at a plurality of hinge points 1901 of the plurality of fingers 1805.

As noted above and with reference to FIG. 2, the drive system 30 may be provided with a reference member and a sensor for sensing at least one degree of relative movement of the piston drive member 32, the sensor being operable to provide an output signal for use in determining a relative degree of retraction or advancement of the piston drive member 32. The reference member and/or sensor may facilitate draw of and dispensing of selected amounts of fluids by sensing a plurality of degrees of relative movement and providing corresponding output signals, relating to each of the detected degrees of relative movement, to the controller 50. In the illustrated embodiment, the reference member and sensor are cooperatively combined and illustrated as position sensor 38, which is now used to describe various positional and rate of operation aspects of the filling system 1.

As noted, the controller 50 may periodically receive signals from the position sensor 38 at predetermined intervals so that the controller 50 may determine a relative degree of movement of the piston 14 For example, the controller may receive signals from the position sensor 38 corresponding with one or more of a fully retracted, a fully advanced, a home retracted position and a home advanced position. As used herein, a "fully advanced position" is a position where the piston 14 is fully advanced within and relative to the tubular member 12. A "fully retracted position" is a position where the piston 14 is retracted relative to the fully advanced position and the piston drive member 32 is disconnectable from the piston 14. A "home advanced position" is a position utilized to indicate an advanced position of the piston 14 that may be utilized during filling operations, which may be different than the fully advanced position. In one embodiment, the home advanced position is located near the proximal end of the tubular member, distal of the fully advanced position. A "home retracted position" is a position utilized to indicate an available retracted position of the piston 14 that may be utilized during filling operations, which may be different than the fully retracted position. In one embodiment, the home retracted position is located near the distal end of the tubular member, proximal of the fully retracted position.

Utility may be realized in using home positions that are different than the fully retracted and advanced positions. For example, utilizing a home advanced position that is distal of a fully advanced position during filling operations may restrict the proximal end of the piston 14 from physically contacting the proximal end of the tubular member 12, thereby restricting wear of the piston 14 and thus the disposable 10. Also, utilizing a home retracted position that is proximal of a fully retracted position may further prevent wear of the disposable 10 by limiting the number of times the piston 14 and piston drive member 32 are selectively interconnected and disconnected.

Figure 9:
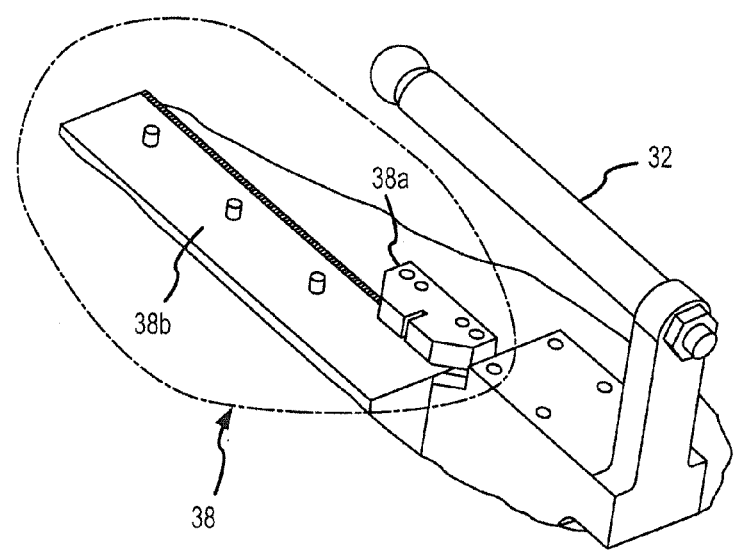
FIG. 9 is a perspective view of one embodiment of a position sensor of FIGS. 1-2.

One embodiment of a position sensor 38 is now described in reference to FIG. 9, the position sensor includes a reader portion 38a and a reference portion 38b. The reader portion 38a may be interconnected to piston drive member 32 for directly corresponding co-movement therewith. The reference portion 38b may be interconnected to a base portion of the drive system 30 that is stationary during use of the filling system 1. The reader portion 38a may be a linear optical encoder adapted to project light from one side of the encoder to another side. The reference portion 38b may include a plurality of demarcations of a predetermined size disposed thereon at a predetermined spacing. The reference portion 38b may further include a transparent strip and/or slit disposed between each of the demarcations. Thus, the transport strips and/or slits also are of a predetermined size and spacing. The reader portion 38a may be mounted relative to the reference portion 38b so that as the reader portion 38a moves relative to the reference portion 38b, light from the light projection side of the reader portion 38a will be alternatively absorbed and passed through the demarcations and transparent strips/slits, respectively. The other side of the reader portion 38a will thus receive a light signal for each of the transparent strips/slits the reader portions moves past. Thus, the reader portion 38a may be able to communicate output signals to the controller 50, which can be processed to determine a number of demarcations/transparent strips or slits passed to determine a degree of relative movement between the reader portion 38a and the stationary reference portion 38b and thus a degree of relative movement of the piston drive member 32. In turn and as may be appreciated, in conjunction one or more of the home advanced, home retracted, fully advanced, and/or fully retraction position, the system may be able to determine a relative position of the reader portion 38a, and therefore the relative position of the interconnected piston drive member 32. As may be appreciated, the demarcations and/or transparent strips and/or slits may comprise a relatively small width (e.g., 30 micrometers and may be spaced a relatively small distance apart (e.g., every 10 micrometers) to facilitate providing accurate position coordinates to the controller 50. Thus, the position sensor 38 may facilitate calculation of and dispensing of accurate amounts (e.g., volumes) of medical liquids via the controller 50. As may be appreciated, the reference portion 38b and reader portion 38a may be switched, wherein the reference portion 38a is mounted to a stationary base of the drive system 30 and the reader portion is interconnected to the piston drive member 32.

Figure 21:
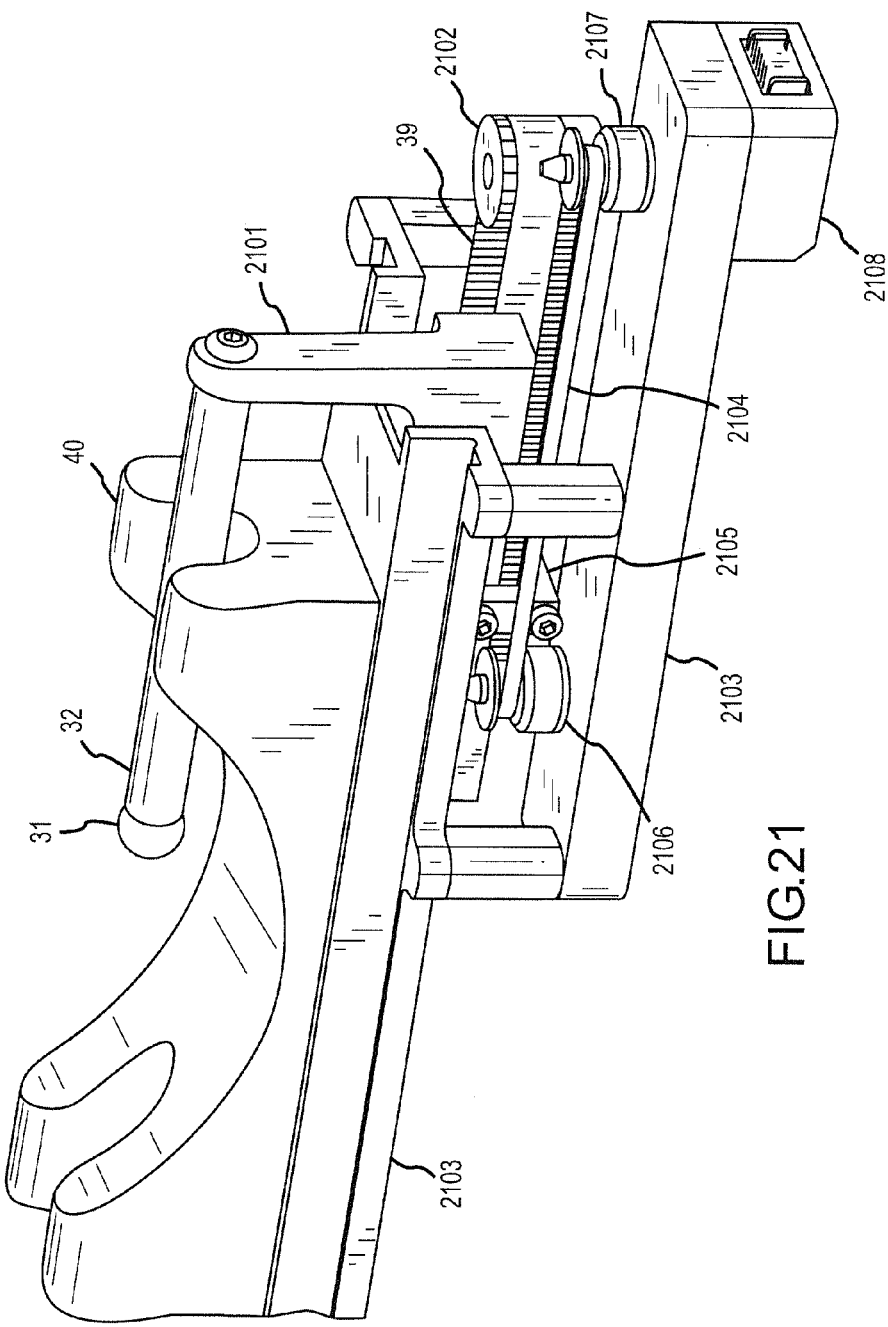
FIG. 21 is a partial perspective view of one embodiment of an automated drive system.

One embodiment of a position sensor is now described in reference to FIG. 21. The position sensor of FIG. 21 is a rotary encoder 2108. Generally, the rotary encoder 2108 may include a rotatable disk within the rotary encoder 2108 interconnected to a rotating member such as a first sensor belt hub 2107. The rotatable disk may comprise a series of slots of a predetermined size disposed at a predetermined spacing. The rotary encoder 2108 may also include a light source and a light sensor positioned on opposite sides of the rotatable disk. As the rotatable disk rotates and the slots move between the light source and the light sensor, the light sensor is alternately able to detect light from the light source and blocked from detecting light from the light source. The light sensor may in turn provide an output related to the detection of light by the light sensor, for example to the controller 50, that may be indicative of the rate at which the disk is rotating and the amount of rotation of the disk. This information can be used, for example by the controller 50, to determine the rotational rate and position of the rotating member such as the first sensor belt hub 2107 to which the rotary encoder 2108 is interconnected. Other types of rotary encoders known to those skilled in the art may also be employed to sense the rotation of the sensor belt hub 2107.

The first sensor belt hub 2107 may be interconnected to a second sensor belt hub 2106 via a sensor belt 2104. The sensor belt 2104 and the first and second sensor belt hubs 2107, 2106 may comprise features, such as protrusions on the sensor belt 2104 and corresponding recessed areas in the first and second sensor belt hubs 2107, 2106, to prevent slippage between the sensor belt 2104 and the first and second sensor belt hubs 2107, 2106. Moreover, the sensor belt 2104 may be interconnected to the piston drive member 32. This interconnection may be through a piston drive member carriage 2101 and a sensor belt clamp 2105. The sensor belt clamp 2105 may be fixedly clamped onto the sensor belt 2104 so that movement of the sensor belt clamp 2105 results in movement of the sensor belt 2104 and corresponding movement of the rotatable disk of the rotary encoder 2108. The sensor belt clamp 2105 may be rigidly attached to the piston drive member carriage 2101. Thusly, movement of the piston drive member 32 may result in a proportional output from rotary encoder 2108.

The piston drive member carriage 2101 may also be fixedly interconnected to the belt 39 that, as previously described, may be interconnected to the motor 36a (as illustrated in FIG. 2). The mount 40 may be fixedly interconnected to a stationary base 2103 that may also serve as a mount for various other components (e.g., the first and second sensor belt hubs 2107, 2106, the rotary encoder 2108, and a drive belt hub 2102). The piston drive member carriage 2101 may be interconnected to the stationary base 2103 in a manner, such as a linear slide, that only permits motion of the piston drive member carriage 2101 along a single axis relative to the stationary base 2103 corresponding to the longitudinal axis of the piston drive member 32. In an alternate embodiment, the piston drive member carriage 2101 may remain stationary and the mount 40 may be reciprocated to achieve the relative motion between the mount 40 and the piston drive member 32.

As illustrated in FIG. 21, the sensor belt 2104 is separate from the belt 39 that is used to move the piston drive member carriage 2101 relative to the stationary base 2103. Alternatively, the rotary encoder 2108 may be directly interconnected to, for example, the drive belt hub 2102. However, interconnecting the rotary encoder 2108 to the sensor belt 2104 instead of to the belt 39 used to drive the piston drive member carriage 2101 may result in greater accuracy in the determination of the position of the piston drive member carriage 2101 since the sensor belt 2104 is isolated from deformations and vibrations that may affect the belt 39 due to the operation of the motor 36a to which it is interconnected.

The rotary encoder 2108 may not be capable of determining the position of the piston drive member 32 under certain situations. For example, upon system start up the position of the piston drive member 32 may be unknown by the controller 50. Under such circumstances, the controller 50 may direct the motor 36a to drive the piston drive member 32 until a position of the piston drive member 32 can be established. The position may be established through the use of additional sensors (not shown). For example, additional sensors may be located to provide a signal to the controller 50 when the piston drive member 32 is located at a predetermined location, such as when the piston drive member 32 is in a fully advanced or fully retracted position. Such end-of-travel sensors may serve to verify or establish the position of the piston drive member 32. After the position of the piston drive member 32 is established, the exact position of the piston drive member 32 may then be tracked by monitoring the output of the rotary encoder 2108. Another method of establishing the position of the piston drive member 32 may be to drive the piston drive member 32 to hard stops located at either end of the range of travel of the piston drive member 32 and then using the output of the rotary encoder 2108 from that point on to keep track of the position of the piston drive member 32.

As noted above and with reference back to FIGS. 1-2, the controller 50 may be interconnected to the motor(s) 36, position sensor 38 or rotary encoder 2108, and/or the user interface 70 to facilitate operation of the filling system 1. In one approach, the controller 50 may be interconnected to the position sensor 38 or rotary encoder 2108 to facilitate control of the position of the piston 14 and thus provide for the dispensing of accurate volumes of medical liquids. More particularly, the controller 50 may use the output signals provided by the position sensor 38 or rotary encoder 2108 in relation to a known diameter of the tubular member 12 to determine an amount of liquid drawn into and dispensed from the tubular member 12.

The controller 50 may be utilized to move the piston 14 to any one of the above described fully advanced, fully retracted, home advanced, or home retracted positions or any positions therebetween (e.g., in conjunction with the position sensor 38 or rotary encoder 2108) to achieve filling of a desired fill volume. For example, the distance between the home advanced position and the home retracted position may correspond to a full filling operations stroke, which may correspond to a maximum volume of fluid that may be dispense during normal filling operations. Also, the fully advanced position may be utilized during priming operations, discussed below, or when switching between differing medical liquids so as to remove a volume of fluid (e.g., air or other gases in relation to priming operations; residual medical liquid when switching between medical liquids) in the portion of the tubular member located between the fully advanced position and the home advanced position (the "void volume").

In this regard, and with reference back to FIGS. 4a-4d, the piston 14 may include a nipple 19 and the tubular member 12 may include a corresponding nozzle portion 11. During various filling operations, the piston 14 may be positioned in or between a home advanced position (FIG. 4c) and a home retracted position (FIG. 4b). Thus, a fluid may remain in the void volume of the tubular member 12 during filling operations. To remove most or all of the fluid in this void volume, the nipple 19 may be advanced and positioned within the nozzle portion 11 (e.g., into the fully advanced position as illustrated FIG. 4d). For example, the nipple 19 may be advanced into and positioned within the nozzle portion 11 during priming operations to assist in removing gases located within the tubular member 12. Also, the nipple 19 may be advanced into and positioned within the nozzle portion 11 when switching between medical liquids so as to facilitate removal of residual medical liquid. In one embodiment, the nipple 19 and nozzle portion 11 comprise corresponding conformal shapes and lengths to facilitate removal of fluids from the void volume.

As noted above, the controller 50 may be operable to move the piston 14 to any position between the fully advanced and fully retracted positions (e.g., in conjunction with the position sensor 38 or rotary encoder 2108). In one embodiment, the controller 50 may be operable to move the piston 14 between a home advanced position and another position to facilitate various operations of the filling system 1, the another position being located distal of the home advanced position and proximal of the home retracted position. That is, the controller 50 may be operable to move the piston 14 less than a full filling operations stroke to facilitate relatively rapid draw and dispensing of fluids. For example, the controller 50 may be operable to move the piston 14 repeatedly between the home advanced position and the another position to facilitate removal of bubbles within the tubular member 12, to facilitate intake and dispensing of a relatively small volume of medical fluid (e.g., useful during dispensing of expensive medical liquids), or to ensure adequate flushing of the above-described void volume.

As noted above, the controller 50 may be interconnected to the motor(s) 36 to control the motor(s) 36. More particularly, the controller 50 may be interconnected to a first motor 36a (e.g., a brushless DC motor) to control one or more operation parameters of the first motor 36a. For example, as the torque of operation of the first motor 36a may correspond to the force of the piston drive member 32, the controller 50 may thus be operable to control the relative force of advancement and retraction of the piston 14 (e.g., via piston drive member 32). The controller may also control the direction of operation of the motor(s) 36 (e.g., clockwise or counterclockwise) to control the direction of operation of the piston 14 (e.g., advancing or retracting) and/or the position of the valve drive member 34.

Figure 10:
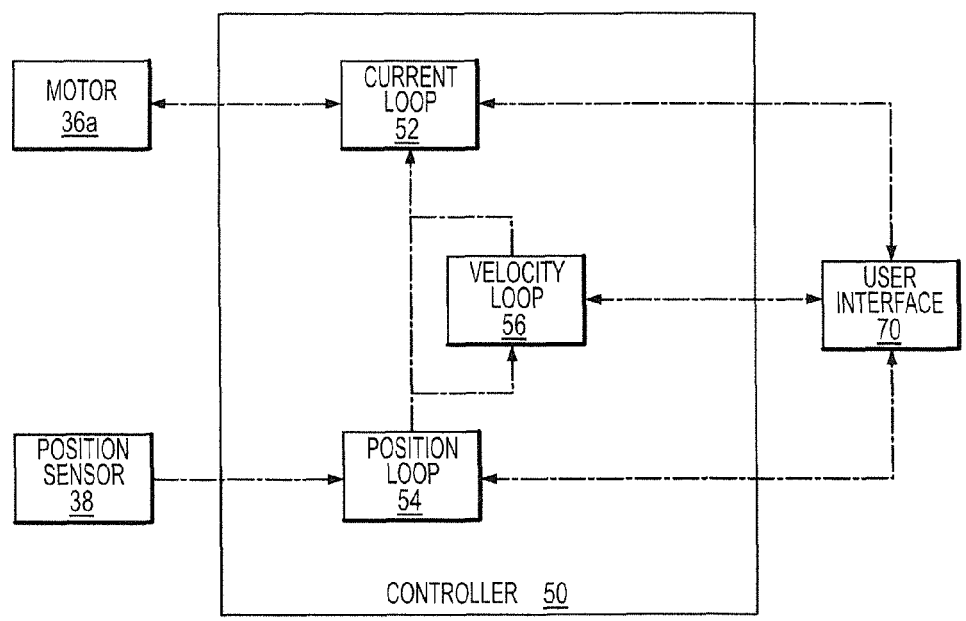
FIG. 10 is a schematic view of one embodiment of a controller of FIGS. 1-2.

In one embodiment and with reference to FIG. 10, the controller 50 may include a current loop 52, a position loop 54 and a velocity loop 56. The current loop 52 may be interconnected to the first motor 36a, the user interface 70, the position loop 54 and the velocity loop 56. The position loop 54 may be further interconnected to the position sensor 38 or rotary encoder 2108, the velocity loop 56 and the user interface 70. The velocity loop may also be interconnected to the user interface 70.

The position loop 54 may be operable to receive output signals from the position sensor 38 or rotary encoder 2108 to facilitate determination of at least one degree of relative movement of the piston drive member 32, as discussed above. The position loop 54 may be interconnected to the user interface 70 to receive parameters associated with positions of the piston drive member (e.g., unit volume parameters, source volume parameters, and other fill-related values, discussed below). The position loop 54 may also be interconnected to the user interface 70 to communicate values associated with position (e.g., a current location of the piston drive member 32). The position loop 54 may be interconnected to the first motor 36a (e.g., via the current loop 52) to control the positioning of the piston drive member 32 and correspondingly the piston 14.

The current loop 52 may be operable to control the amount and polarity of current supplied to the first motor 36a to control one or more motor operations (e.g., rate of operation, direction of operation). The current loop 52 may be interconnected to the user interface 70 to receive parameters associated with operation of the first drive motor (e.g., pressure parameters, fluid direction parameters, and other fill-related values, discussed below). The current loop 52 may also be interconnected to the user interface 70 to communicate values associated with motor and/or piston operation (e.g., an operation rate, an operation direction, etc.).

The current loop 52 may be operable to control the first motor 36a to thus control the force of advancement and/or retraction of the piston 14. In this regard, the current loop 52 may receive parameters via the user interface 70 and operate the first motor 36a in relation thereto to achieve a desired pressure range within the tubular member 12. More particularly, during retraction of the piston 14 a negative pressure differential between the tubular member 12 and medical liquid source(s) 60 is created to flow fluids from the medical liquid source(s) 60 into the tubular member 12. If this pressure differential is too high, the medical liquids flowing from the medical liquid source(s) 60 may evaporate, thereby producing undesired gases within the filling system 1. Thus, during retraction of the piston 14, it is desirable to maintain a predetermined retraction pressure range within the tubular member 12. In one arrangement, the predetermined retraction pressure may be less than 0 psig but not less than −12 (negative twelve) psig. In another arrangement, the predetermined retraction pressure may be less than 0 psig but not less than −8 (negative eight) psig.

Moreover, during advancement of the piston 14, a positive pressure is created within the various fluid-containing components (e.g., the tubular member 12, valve 20, second fluid line 82 and associated interconnections). These components may have maximum pressure thresholds. Thus, during advancement of the piston 14 it is also desirable to maintain a predetermined advancement pressure range within the tubular member 12. Preferably, the predetermined advancement pressure may be more than 0 psig but not greater than 45 psig. More preferably, the predetermined advancement pressure may be more than 0 psig but not greater than 60 psig. Furthermore, it may be desirable to operate the piston 14 at or near threshold velocities in relation to the pressure thresholds so as to rapidly draw and dispense medical liquids. Thus, it is desirable to quickly ramp the piston 14 velocity to achieve the desired pressure ranges within the tubular member 12 to achieve a desired draw and dispensing rate without exceeding such threshold pressures.

The amount of pressure created in the tubular member 12 during advancement and retraction of the piston 14 may be a function of a variety of variables, including the viscosity of the fluid being drawn or dispensed, the torque and/or velocity of advancement of the piston 14 and the cross-sectional area of the internal surfaces of the tubular member 12. As may be appreciated, the types of medical liquids that may be employed in the filling system may be numerous. Correspondingly, the viscosity of fluids utilized within the filling system may range greatly. Thus, using viscosity in the calculation of the pressure within the filling system 1 may require compiling a database of known medical liquids and their corresponding viscosities, as well as requiring an input as to the type of medical liquid being employed. Hence, it may not be desirable to utilize viscosity in the determination of pressure.

One approach to achieving a desired pressure within the filling system 1 without utilizing viscosity information is to utilize the known cross-sectional internal area of the tubular member 12 in relation to a known force being supplied to the piston 14. There are multiple methods of determining force being supplied to the piston. For example, a fixed force transducer may be utilized (e.g., with the piston drive member 32 and/or piston 14), and in conjunction with the controller 50 and first motor 36a, the piston 14 may thus be moved at a desired force. In another embodiment, a known force being supplied by the first motor 36a to the piston drive member 32 may be utilized. More particularly, a motor adapted to determine its operating force (e.g., a known torque value) may be utilized as the first motor 36a, wherein the controller 50 may be utilized in a closed-loop fashion with the first motor 36a, to operate the first motor 36a within a predetermined force range to correspondingly operate the piston 14 within a predetermined pressure range.

For example, the first motor 36a may include a moveable output member (e.g., an armature) interconnectable to the piston drive member 32, a magnetic field member (e.g., a stator) for inducing movement of the moveable output motor, and a sensor (e.g., an optical, electrical and/or magnetic sensor) for sensing a position of the moveable output member in relation to the magnetic field member and for providing an output signal to a controller 50 in corresponding relation thereto. The output signal may be indicative of, for example, one or more of a force, velocity and/or position of the moveable output member in relation to the magnetic field member. The controller 50 may be operable to compare the output signal to a predetermined operating parameter (e.g., a fill-related parameter, discussed below) and to provide an appropriate control signal to the magnetic field member in relation thereto to operate the first motor 36a within a predetermined operating range (e.g., an operating range corresponding with a force of advancement or a force of retraction of the piston). In one embodiment, the control signal corresponds to an amount of current being supplied to the magnetic field member.

Thus, the tubular member 12, piston 14, first motor 36a, and controller 50 may be utilized to operate the filling system 1 at a desirable advancement and/or retraction pressure. More particularly, the current loop 52 of the controller 50 may be utilized in conjunction with the first motor 36a to achieve a predetermined motor force range during advancement and/or retraction of the piston 14 to correspondingly move the piston 14 within a desirable force range and thus create a pressure within a predetermined range within the tubular member 12. For example, upon initiating filling and/or priming operations, the current loop 52 may communicate supply a predetermined amount of current the first motor 36a, whereupon the first motor 36a may operated achieve a desired torque range (e.g., in accordance with a preprogrammed/predetermined ramp profile). This torque range may correspond to a desired force range and thus a desired pressure within the tubular member 12 during advancement and retraction of the piston 14. As discussed in further detail below, pressure parameter(s) may be utilized by the controller 50 (e.g., in relation to the predetermined ramp profile) to further control the pressure within of tubular member 12. Thus, the piston 14 may be operated within a range of forces to achieve a desired pressure within the tubular member 12. Moreover, the filling system 1 may be operable to automatically control the retraction and advancement of the piston drive member 32 to achieve first and second fluid flow rate ranges, respectively, (e.g., draw rates corresponding with the aforementioned predetermined retraction pressure ranges, and dispensing rates corresponding with the aforementioned predetermined advancement pressure ranges).

In another approach, the known cross-sectional internal area of the tubular member 12, a velocity of the piston 14 and the fluid being dispensed may be utilized to determine pressure. In this regard, the tubular member 12, piston 14, first motor 36a, position sensor 38 or rotary encoder 2108, and controller 50 may be utilized to move the piston 14 at a desirable advancement or retraction velocity and the user interface may be adapted for input of a fluid-type parameter, discussed below, relating to the fluid being utilized within the tubular member. More particularly, the position sensor 38 or rotary encoder 2108 may provide output signals relating to the degrees of relative movement to the position loop 54, which may be communicated to the velocity loop 56. The velocity loop 56 may correlate these degrees of relative movement readings over time (e.g., every 50 μsec) to determine a rate value (e.g., the relative velocity) indicative of a rate of relative movement of the piston drive member 32 and/or of the piston 14 in relation to a desired rate value (e.g., a desired velocity). The fluid-type parameter (e.g., one or more of a viscosity, density or other parameter) may also be communicated to the controller 50 (e.g., to the velocity and/or current loop) to facilitate calculation of the mass of the fluid being utilized to further facilitate calculation of force. The controller 50 may thus determine and control the first motor 36a to operate the piston 14 at a desired velocity in relation to the fluid-type parameter.

One of the calculated motor force and the piston velocity may be used by the controller 50 as a primary pressure control parameter to control the pressure within the tubular member 12. In one embodiment, the other of the calculated motor force and piston velocity may be used as a secondary pressure control parameter to assist in controlling the pressure within the tubular member 12. More particularly, a primary pressure control parameter may be utilized to achieve a desired pressure, where the first motor 36a may be operated in relation to this primary pressure control parameter to achieve a desired pressure. A secondary pressure control parameter may be utilized as a boundary to the primary pressure control parameter (e.g., a ceiling) to ensure the pressure within the tubular member 12 stays within a predetermined range.

For example, the calculated motor force may be the primary pressure control parameter used by the controller 50, where the controller 50 and first motor 36a operate in a closed-loop fashion, as described above, to achieve a predetermined pressure range within the tubular member 12. The calculated piston velocity may be the secondary pressure control parameter, where the controller compares the measured piston velocity to a predetermined piston velocity parameter, such that if the controller 50 determines that the calculated piston velocity exceeds the predetermined piston velocity parameter, the controller 50 automatically decreases the force being supplied by the first motor 36a (e.g., via maintaining or decreasing the amount of current being supplied to the first motor 36a) to correspondingly decrease the velocity of the piston 14 in relation to the secondary pressure control parameter. In one embodiment, the controller 50 may automatically terminate filling operations if the measured piston velocity exceeds a predetermined piston velocity parameter, and may provide an indication to a user, via the user interface, that the piston velocity parameter was exceeded, as described in further detail below. Thus, the controller may use the output signals of the position sensor 38 or rotary encoder 2108 to cross-check the first motor 36a output to ensure the filling system 1 is operating within a predetermined pressure range.

Other methods may also be utilized to determine the pressure within the filling system. For example, a pressure transducer may be utilized within the disposable (e.g., within the tubular member 12 and/or valve 20) and interconnected to the controller 50 to determine the operating pressure. A pressure transducer may also be utilized in conjunction with the controller 50 to determine pressures subsequent to draw and dispensing of fluids so as to facilitate determining an appropriate delay, if any, between draw and dispensing operations. Such a delay may facilitate fluid pressure equalization between fluid draw and dispensing operations, which may further facilitate the dispensation of accurate and repeatable volumes of medical liquids. As may be appreciated, such delay and corresponding pressure equalization may enable any produced bubbles to settle, and may restrict cavitation of the medical liquid. This delay may be hard coded into the controller 50 and/or may be a parameter of the time delay parameters, discussed below. A pressure transducer may also be utilized within the valve 20 to facilitate drawback operations. As discussed in further detail below, in drawback operations, a drawback parameter (e.g., a fixed volume parameter or pressure reading from the noted pressure transducer) may be utilized by the controller 50 to restrict drips between dispensing operations, wherein the controller 50 retracts the piston a predetermined amount to draw a fixed volume of medical liquid back into the filling system 1.

In another embodiment, the first motor 36a may be utilized to determine a relative position and/or velocity of piston 14. As noted above, brushless DC motors and the like may be operable to determine an operating force (e.g., a torque). As the calculation of the operating force of the first motor 36a may comprise the use of position and velocity readings of the first motor 36a, such position and velocity readings may output as signals to the controller 50 to facilitate determination of relative position and velocity of the interconnected piston 14. Such readings (e.g., force, position, speed, torque, etc.) may also be communicated from the controller 50 to the user interface 70 for display thereof. Also, the use of such readings may obviate the need for the position sensor 38.

The velocity loop 56 may be operable to receive output signals from the position sensor 38 or rotary encoder 2108 to facilitate determination of at rate of relative movement of the piston drive member 32, as discussed above. The velocity loop 56 may be interconnected to the user interface 70 to receive parameters associated with a rate of operation of the piston drive member (e.g., pressure parameters and other fill-related values, discussed below). The velocity loop 56 may also be interconnected to the user interface 70 to communicate values associated with velocity (e.g., a rate of operation of the piston 14 and/or piston drive member 32). The velocity loop 56 may be interconnected to the first motor 36a (e.g., via the current loop 52) to control the rate of operation of the piston drive member 32 and correspondingly the piston 14 (e.g., as a secondary pressure control parameter, discussed above).

As noted above and with reference back to FIGS. 1-2, the filling system 1 may include a user interface 70. The user interface 70 may include a graphical user interface adapted to accept various fill-related values, inputs and/or parameters ("fill-related parameter(s)") in relation to the operation of the filling system 1. For example, the user interface 70 may comprise a touch-screen monitor interconnected to operating system software (e.g., WINDOWS, Microsoft Corp., Redmond, Wash., United States of America) utilized by the controller 50. As may be appreciated, parameters received via the user interface 70 may be thus communicated to the controller 50 for processing thereby to facilitate operation of the filling system 1.

Figure 11A:
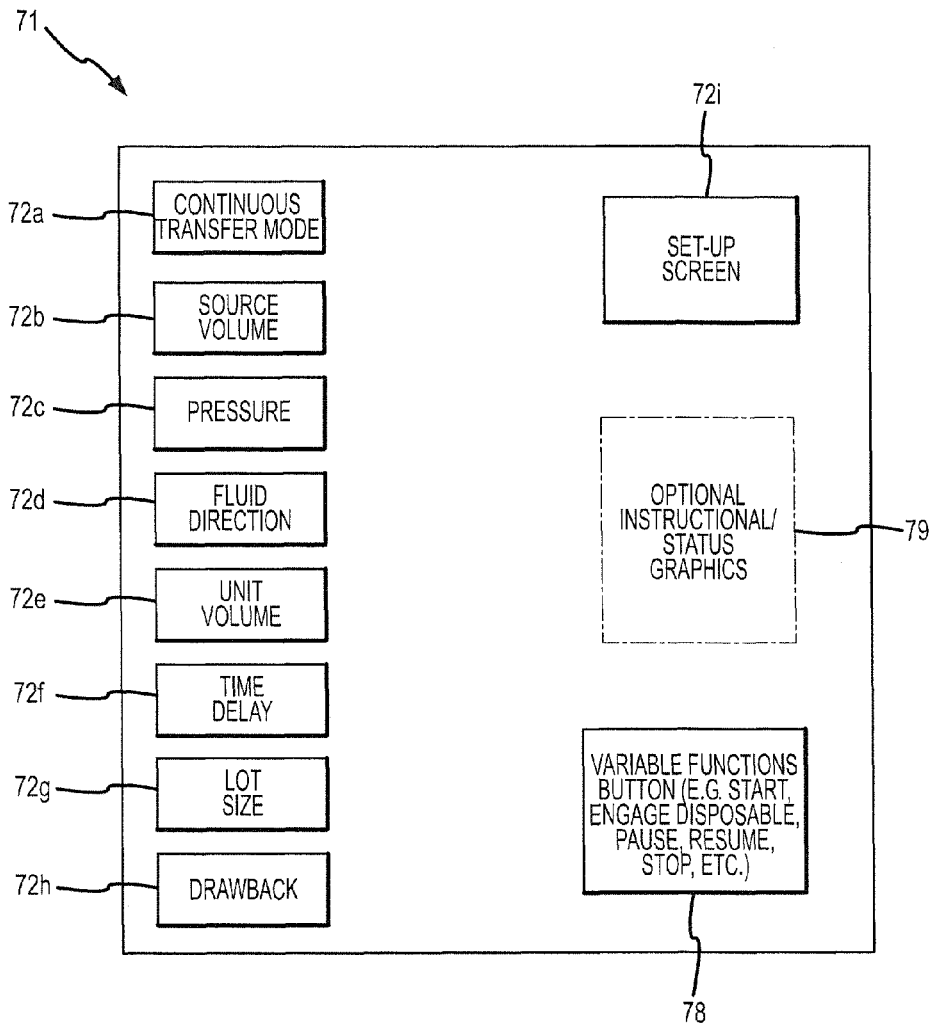
FIG. 11a is a schematic view of one embodiment of a first screen of a user interface of FIGS. 1-2.
Figure 11B:
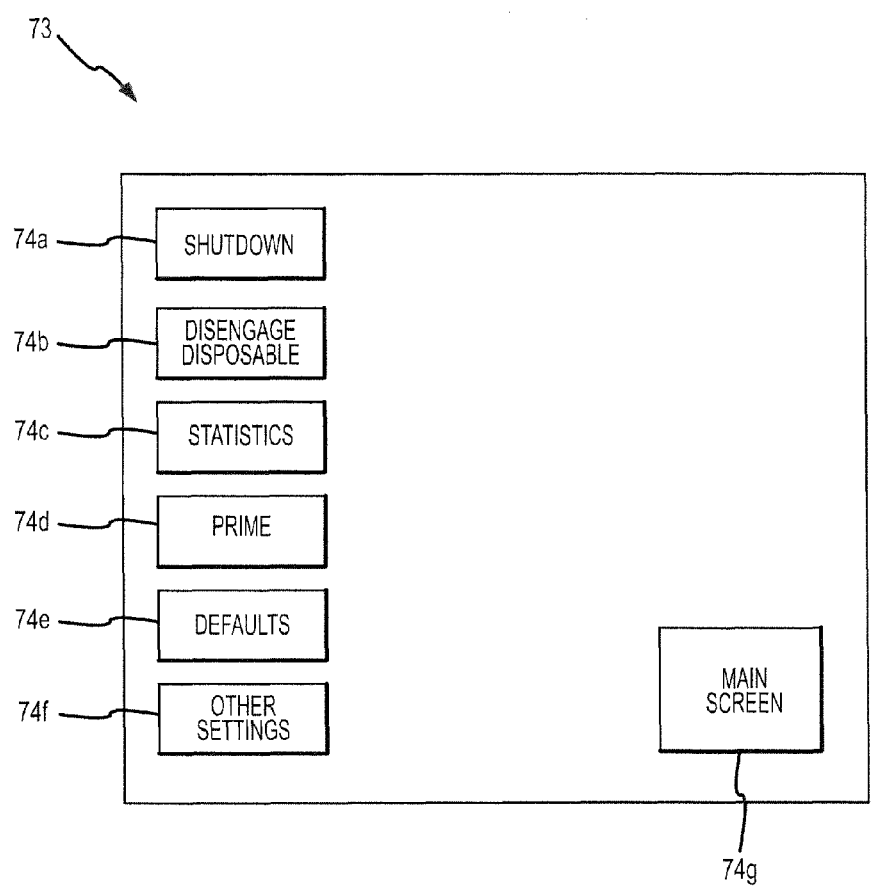
FIG. 11b is a schematic view of one embodiment of a second screen of a user interface of FIGS. 1-2.

One embodiment of a user interface 70 employable with the filling system 1 is now described with reference to FIGS. 11a-11b. The user interface 70 may include a main screen 71 comprising a plurality of command buttons 72a-72h, a set-up button 72i, which may call a set-up screen 73, and a variable functions button 78, which may be operable to initiate various operations of the filling system 1 via the controller 50.

Each of the command buttons 72a-72h may be associated with one or more fill-related parameter(s) and may be communicated to the controller 50 to facilitate operation and control of the filling system 1. For example and as discussed in further detail below, a first command button 72a may be associated with one or more continuous transfer mode parameters ("continuous transfer mode parameter(s)"), a second command button 72b may be associated with one or more source volume parameters ("source volume parameter(s)"), a third command button 72c may be associated with one or more pressure parameter(s) ("pressure parameter(s)"), a fourth command button 72d may be associated with one or more fluid direction parameters ("fluid direction parameter(s)"), a fifth command button 72e may be associated with one or more unit volume parameters ("unit volume parameter(s)"), a sixth command button 72f may be associated with one or more time delay or time interval parameters ("time delay parameter(s)"), a seventh command button 72g may be associated with one or more lot size parameters ("lot size parameter(s)"), and an eighth command button 72h may be associated with one or more drawback parameters ("drawback parameter(s)"). Lot size parameters may also be referred to as "batch quantity parameters." Such parameters may be communicated to the controller 50, which may utilize such communicated parameters to facilitate operation of the filling system 1. Other command buttons (not shown in FIG. 11a) may include fill related parameters such as a command button that may be associated with one or more speed parameters ("speed parameter(s)").

For example, the continuous transfer mode parameter(s) may be associated with a continuous or non-continuous operation mode of the filling system 1. In one embodiment, the continuous transfer mode parameter(s) may be activated (e.g., toggled on) where the controller 50 controls the filling system 1 to repeatedly complete draw and dispensing of medical liquid. This mode is useful, for example, when fluid lines a first fluid line is interconnected to a first port of the medical liquid source(s) 60 and a first port of the valve 20, and a second fluid line is interconnected to a second port of the medical liquid source(s) 60 and a second port of the valve 20, wherein medical liquid may be drawn from the medical liquid source(s) 60 into the disposable 10 via the first fluid line and first ports, and the same medical liquid may be dispensed from the disposable 10 to the same medical liquid source(s) 60 via the second fluid line and second ports so that the filling system 1 can repeatedly draw a medical liquid from and dispense that same medical liquid back to the medical liquid source(s) 60 to ensure that such medical liquid is sufficiently mixed. In a particular embodiment of this continuous transfer mode, the piston 14 is repeatedly retracted from and advanced to the home advanced and home retracted positions, respectively, so as to draw and dispense a relatively large volume of medical fluid. Additionally, one or more of the other fill-related parameter(s) may be disabled (e.g., the source volume parameter(s), the unit volume parameter(s), the time interval parameter(s), the lot size parameter(s) and/or the drawback parameter(s)) when the continuous transfer mode parameter(s) are activated since those other parameters may not be required to operate the filling system 1 when the continuous transfer mode parameter(s) are activated.

When the continuous transfer mode parameter(s) are non-active (e.g., toggled off), the controller 50 may operate the filling system 1 in a non-continuous manner. For example, first and second fluid lines 80, 82 may be interconnected to the disposable 10, medical liquid source(s) 60 and receptacle(s) 62, as described above in relation to FIGS. 1-2, wherein the controller 50 may control the filling system 1 to fill receptacle(s) 62 with medical liquid from the medical liquid source(s) 60 until a desired amount of receptacle(s) 62 have been filled (e.g., determined using lot size parameter(s)). The controller 50 may also control the filling system 1 to fill receptacle(s) 62 until the medical source(s) 60 have been substantially depleted of a predetermined volume of liquid (e.g., determined using source volume parameter(s)), and/or the controller 50 may control the filling system 1 to fill an individual one of the receptacle(s) 62 until another input is received.

In one embodiment, the controller 50 may be operable to conduct filling operations without receiving an input relating to the continuous transfer mode parameter(s). In this regard, a default non-continuous transfer mode (e.g., the continuous transfer parameter(s) are non-active) may be used.

The source volume parameter(s) may be associated with the volume of medical liquid in the medical liquid source(s) 60 and may be communicated to the controller 50 to facilitate operation of the filling system 1 (e.g., determining an amount of receptacles that can be filled before the medical liquid source(s) 60 are substantially depleted of medical liquid). In one embodiment, the controller 50 may be operable to conduct filling operations without receiving an input relating to the source volume parameter(s). For example, the controller 50 may operate the filling system 1 in the above-described continuous transfer mode, the controller 50 may operate the filling system 1 to fill receptacle(s) 62 until a desired amount of receptacle(s) 62 have been filled (e.g., determined using lot size parameter(s)), the controller 50 may operate the filling system 1 to fill an individual one of the receptacle(s) 62 until another input is received, or default source volume parameter(s) may be used.

The pressure parameter(s) may correspond to one or more desired operation pressures. As discussed above, the controller 50 and disposable 10 may be designed to ensure that the piston 14 achieves a predetermined force or velocity to achieve a desired pressure. The pressure parameter(s) (e.g., one or more velocity and/or force parameters) may be associated with a particular velocity or force of operation of the piston 14 and thus a particular pressure. In this regard, the user interface 70 may communicate the pressure parameter(s) to the controller 50, which may utilize such pressure parameter(s) (e.g., via the above-described current or velocity loop 52, 56) to control a pressure of the filling system 1.

In a particular embodiment, the pressure parameter(s) may include both velocity and force parameters, which may be communicated to and utilized by the controller 50 to control the pressure. For example, the pressure parameter(s) may include one or more of a maximum or minimum advancement velocity parameter, a maximum or minimum advancement force parameter, a maximum or minimum retraction velocity parameter and/or a maximum or minimum retraction force parameter, which the controller 50 may use to maintain a pressure within such thresholds. Thus, the user interface 70 may be operable to accept specific piston velocity and force operation parameter(s), which may be used by the controller to control a pressure of the filling system 1. In one embodiment, the controller 50 may be operable to conduct filling operations without receiving an input relating to the pressure parameter(s). In this regard, default maximum and/or minimum velocity and/or force values may be utilized.

The speed parameter(s) may correspond to one or more desired piston operation speeds. The speed parameter(s) may be closely related to the pressure parameter(s) in that the speed of the piston 14 may be related to the pressure. As discussed above, the controller 50 and disposable 10 may be designed to ensure that the piston 14 achieves a predetermined speed. The speed parameter(s) may be associated with a particular velocity of operation of the piston 14 and thus a particular pressure. In this regard, the user interface 70 may communicate the speed parameter(s) to the controller 50, which may utilize such speed parameter(s) to control a pressure of the filling system 1.

The fluid direction parameter(s) may be associated with a first fluid direction and a second fluid direction. As described in further detail below, the filling system 1 may be operable to dispense medical liquids from the medical liquid source(s) 60 to the receptacle(s) 62 and vice versa. The first fluid direction may be associated with transferring medical liquids from the medical liquid source(s) 60 to the receptacle(s) 62. The second fluid direction may be associated with transferring medical liquids from the receptacle(s) 62 to the medical liquid source(s) 60. As may be appreciated, the first fluid direction may be useful when a large amount of fluid in a single container (e.g., the medical liquid in the medical liquid source(s) 60) is desired to be dispensed to a plurality of other containers (e.g., the receptacle(s) 62), such as in the production of liquid medication of a desired volume and concentration. The second direction may be useful when a small amount of fluid contained in a plurality of containers (e.g., the receptacle(s) 62) is desired to be collected into a single container (e.g., the medical liquid source(s) 60), such as when a liquid medication contained in a plurality of ampoules is desired to be collected in a single reservoir. In one embodiment, the controller 50 may be operable to conduct filling operations without receiving an input relating to the fluid direction parameter(s). In this regard, the above-described first fluid direction may be used as a default.

The unit volume parameter(s) may be associated with the volume of liquid to be provided to each of the receptacle(s) 62, which may be communicated to the controller 50 to facilitate operation of the filling system 1 (e.g., calculating the amount the piston drive member 32 should be advanced to fill one or more of the receptacle(s) 62). Thus, the controller may be operable to dispense a predetermined volume of medical liquid from the tubular member 12 to the receptacle(s) 62. In one embodiment, the controller 50 may be operable to conduct filling operations without receiving an input corresponding to the unit volume parameter(s). In this regard, the controller 50 may operate the filling system 1 in the above-described continuous transfer mode or default unit volume parameter(s) may be used.

The time delay parameter(s) may be associated with a delay time between dispensing medical liquids into the receptacle(s) 62. For example, a time delay of 2 seconds may be utilized between dispensing operations to provide sufficient time for the receptacle(s) 62 to be moved into an appropriate position. In one embodiment, the controller 50 may be operable to conduct filling operations without receiving an input relating to the time delay parameter(s). In this regard, the controller 50 may operate the filling system 1 in the above-described continuous transfer mode or default time delay parameter(s) may be used.

The lot size parameter(s) may be associated with the number of receptacle(s) 62 to be filled, which may be communicated to the controller 50 to facilitate operation of the filling system 1 (e.g., calculating whether sufficient medical liquid is in the medical liquid source(s) 60 and/or tubular member 12 to fill one or more of the remaining receptacle(s) 62; calculating the remaining number of receptacle(s) 62 to be filled before termination filling operations). In one embodiment, the controller 50 may be operable to conduct filling operations without receiving an input relating to the lot size parameter(s). In this regard, the controller 50 may operate the filling system 1 in the above-described continuous transfer mode, the controller 50 may operate the filling system 1 to fill an individual one of the receptacle(s) 62 until another input is received, the controller 50 may operate the filling system 1 to fill receptacle(s) 62 until the liquid medical source(s) 60 have been substantially depleted of a predetermined volume of liquid (e.g., determined using source volume parameter(s)) or default lot size parameter(s) may be used.

The drawback parameter(s) may be associated with retraction of the piston 14 after a dispensing operation has been completed. In one embodiment, the drawback parameter(s) may be activated (e.g., turned on) where the piston 14 will retract in relation to another parameter (e.g., a drawback volume or pressure parameter) at the end of a dispensing operation. Retracting the piston 14 after a dispensing operation may be useful to facilitate the dispensing of a desired amount of medical liquid and restrict contamination of incoming receptacle(s) 62. For example and as discussed below, the second fluid line 82 may be interconnected to a second dispensing apparatus (e.g., a needle). Upon completing a dispensing operation, medical liquid may be suspended outside this second dispensing apparatus (e.g., in droplet form). In some instances, it may be desirable to draw this suspended medical liquid back into the second dispensing apparatus. Thus, the drawback parameter(s) may be utilized by the controller 50 to retract the piston 14 a predetermined amount (e.g., equivalent to a specific volume), or in relation to pressure readings from a pressure transducer, after a dispensing operation has been completed to facilitate draw of the suspended liquid back into the filling system 1. In this regard, the position sensor 38 or rotary encoder 2108 may be utilized, as described above, to facilitate retraction of the piston 14 to the desired position. Since the suspended liquid may be drawn back into the filling system 1, there is reduced risk of contamination of incoming receptacle(s) 62. In one embodiment, the drawback parameter(s) may be deactivated, where the piston 14 will not slightly retract after a dispensing operation. Other parameters may also be utilized. For example, one or more fluid-type parameter(s) ("fluid-type parameter(s)") may be utilized to facilitate input of various fluid parameters (e.g., medical liquid physical properties, such as density, viscosity, vapor pressure, etc.) and/or environmental conditions (e.g., temperature, atmospheric pressure, elevation, etc.) In one approach, the fluid-type parameter(s) may be the name(s) of medical liquid(s) being utilized, and the controller 50 may comprise a database relating various physical properties of the medical liquid to the medical liquid(s) names. In one embodiment, the fluid-type parameter(s) may be utilized in conjunction with other parameters to facilitate operating of the filling system. For example, the fluid-type parameter(s) may be utilized with the pressure parameter(s) to facilitate operation of the piston 14 within a predetermined force and/or velocity range to restrict undesired outcomes (e.g., foaming, bubbles, cavitation, etc.). In a particular embodiment, upon input of the fluid-type parameter(s), the controller 50 may automatically select suitable pressure parameter(s) and/or drawback parameter(s), may prompt a user with recommended suitable pressure parameter(s) and/or drawback parameter(s), or may request input relating to suitable pressure parameter(s) and/or drawback parameter(s).

One or more size-related values may also be utilized. By way of primary example, one or more disposable size parameter(s) ("disposable size parameter(s)") may be used and may correspond with one or more sizes associated with the disposable (e.g., one or more diameters of the tubular member 12; the length of the tubular member 12). In a particular embodiment, the disposable size parameter(s) may be utilized to facilitate the determination of one or more suitable pressure parameter(s) or drawback parameter(s). For example, a disposable from a plurality of different size disposables may be selected and corresponding disposable size parameter(s) may be input via the user interface, whereupon the controller may automatically select suitable pressure parameter(s) and/or drawback parameter(s), prompt a user with recommended suitable pressure parameter(s) and/or drawback parameter(s), or may request input relating to suitable pressure parameter(s) and/or drawback parameter(s).

By way of secondary example, one or more fluid line parameter(s) ("fluid line parameter(s)") may be utilized and may correspond to an inner diameter of one or more interconnected fluid lines and the fluid line parameter(s) may be utilized to facilitate the determination of one or more suitable pressure parameter(s) or drawback parameter(s). For example, a tubing line may be selected from a plurality of tubing lines, and corresponding fluid line parameter(s) may be input via the user interface, whereupon the controller may automatically select suitable pressure parameter(s) and/or drawback parameter(s), may prompt a user with recommended suitable pressure parameter(s) and/or drawback parameter(s), or may request input relating to suitable pressure parameter(s) and/or drawback parameter(s).

By way of tertiary example, one or more receptacle type parameter(s) may also be utilized, wherein parameter(s) relating to the type of receptacle may be input. In one embodiment, the receptacle type parameter(s) may correspond to one or more of a vial, ampoule, or syringe of a specific size. For example, the receptacle type parameter(s) may correspond to a specific syringe size. In a particular embodiment, the receptacle size parameter(s) may be utilized to facilitate the determination of one or more suitable pressure parameter(s) or drawback parameter(s). For example, upon input of the receptacle type parameter(s), the controller 50 may automatically select suitable pressure parameter(s) and/or drawback parameter(s), may prompt a user with recommended suitable pressure parameter(s) and/or drawback parameter(s), or may request input relating to suitable pressure parameter(s) and/or drawback parameter(s).

In another embodiment, a sensor may be employed to facilitate the determination of any of the above size-related parameter(s). For example, a sensor operable to determine a size of an interconnected disposable and/or fluid line may be employed by the drive system 30 (e.g., in the mount 40). The sensor may be further operable to provide output signals to the controller 50 corresponding with such determined disposable size and/or fluid line size. The controller 50 may then automatically select suitable pressure parameter(s) and/or drawback parameter(s), may prompt a user with recommended suitable pressure parameter(s) and/or drawback parameter(s), or may request input relating to suitable pressure parameter(s) and/or drawback parameter(s) based upon such sensed size-related parameter(s).

As may be appreciated, many of the above parameters may be utilized alone or in conjunction with one or more other parameters. Moreover, in addition to the examples provided above, the controller 50 may automatically select one or more suitable fill-related parameter(s) based on the input of one more other fill-related parameter(s), may prompt a user with recommended fill-related parameter(s) based on the input of one more other fill-related parameter(s), and/or may request input relating to suitable fill-related parameter(s) based on the input of one more other fill-related parameter(s).

As noted above, the user interface may include a set-up screen 73, which may be called from the main screen by set-up button 72i. One embodiment of a set-up screen 73 is illustrated in FIG. 11b. The set-up screen 74 may include set-up buttons 74a-74f, which may be associated with particular set-up functions of the filling system 1. For example, the set-up screen may include a first set-up button 74a corresponding with one or more shutdown parameter(s), which may shutdown the user interface 70 and/or other various components of the filling system 1. A second set-up button 74b may correspond to one or more disengagement parameters ("disengagement parameter(s)"), which may be communicated to the controller 50 to facilitate disengagement of the disposable from the drive system 30. In a particular embodiment, when the disengagement parameter(s) are activated, the controller 50 may fully retract the piston drive member 32 and/or may rotate the valve drive member 34 to the above-described third position (e.g., a neutral position) to facilitate removal of the disposal 10 from the drive system 30.

In one embodiment, upon activation of disengagement parameter(s), the valve 20 may be positioned to the third valve position prior to full retraction of the piston 14. As noted above, the third valve position may restrict fluid communication between the valve ports 26, 27 and the tubular member 12 thereby sealing a proximal end of the tubular member. The seal member 16 seals a distal end of the tubular member 12, and thus the tubular member 12 may be substantially hermetically sealed when the valve 20 is in this third valve position. Thus, as the piston 14 is retracted, a negative pressure will be created within the tubular member 12, and upon disengagement of the piston drive member 32 from the piston 14, the piston 14 may, due to such negative pressure, be advanced within the tubular member 12. This advanced position may be different than a shipping position, which may thus indicate to a user that the disposable 10 has been previously used, thereby restricting inadvertent subsequent use of the previously utilized disposable 10. Correspondingly and as noted above, the valve stem 24 may be shipped in a first position within the valve housing 22 (e.g., within the first portion of the valve housing 22 corresponding with diameter H1) and utilized in a second position within the valve housing (e.g., within the second portion of the valve housing 22 corresponding with diameter H2). The above described negative pressure differential may also maintain the valve stem 24 in the second position, which may also indicate to a user that the disposable has been utilized. Additionally, the diameter of the valve housing 22 may be such that the valve stem 24 is restricted from moving back to the first position after use, thereby indicating to a user that the disposable has been utilized without using a negative pressure.

A third set-up button 74c may correspond with one or more statistics parameter(s), which may call a statistics display screen.

A fourth set-up button 74d may correspond to one or more prime parameters ("prime parameter(s)"). As discussed in further detail below, priming operations are utilized to fill the various components of the filling system 1 with liquid prior to the filling of the receptacle(s) 62. In this regard, the prime parameter(s) may be communicated to the controller 50 to initiate automatic or semi-automatic priming operations (e.g., priming the filling system 1 with a predetermined amount of medical fluid).

A fifth set-up button 74e may correspond to one or more default parameters ("default parameter(s)"). The default parameter(s) may include default, minimum and/or maximum values associated with any of the above-described fill-related parameters, such as one or more of the continuous transfer mode parameter(s), the source volume parameter(s), the pressure parameter(s), the unit volume parameter(s), the time delay parameter(s), the lot size parameter(s) and the drawback parameter(s), to name a few.

A sixth set-up button 74f may correspond to one or more other settings parameters ("settings parameter(s))", such as an amount of liquid to be utilized in relation the prime parameter(s), and/or a pressure to be achieved or a volume of liquid to be drawn in relation to the drawback parameter(s).

As also noted above and referring back to FIG. 11a, the main screen 71 may include a variable functions button 78, which may be utilized to initiate various operations of the filling system 1 via the controller 50. For example, the various functions button 78 may correspond to one of a start, pause, resume, stop or engage disposable command. The start command may signal the controller 50 to start filling operations in accordance with the various fill-related parameter(s), discussed above, until another input is received. The pause command may signal the controller 50 to pause operation of the filling system 1. The resume command may signal the controller 50 to resume operation of the filling system 1 (e.g., after a pause command was received). The stop command may signal the controller to stop filling operations 1 (e.g., in relation to an active continuous transfer mode). As may be appreciated, the stop command may completely stop and reset the filling system 1 so that other fill-related parameter(s) may be input and/or new filling operations may being, whereas a pause command pauses the filling sequence and fillings operations parameters may not be changed. The engage disposable command may command the controller to move the piston drive member 32 to engage the disposable 14 (e.g., move from a fully retracted position to a home retracted position).

A label may utilized to label the variable functions button 78 to indicate a currently available command (e.g., a label of "Start" corresponding to a start command), and/or the label may indicate a necessary operation that must occur for the filling system 1 to be operable (e.g., a text label of "Load Disposable" to indicate that a disposable 10 must be interconnected to the filling system 1 to enable filling operations). The variable functions button may also be disabled according to the status of the filling system 1 (e.g., when a disposable is not interconnected to the filling system 1). The label may include any characters and/or graphics necessary to convey the desired message.

As noted above, a label may be utilized in conjunction with the variable functions button to illustrate various instructions, an action to be taken, the status of the filling system 1, etc. To further facilitate indicating such instructions and/or an action to be taken and/or the status of the filling system 1, an optional graphics portion 79 may be included on the main screen 71. The graphics portion 79 may be utilized to illustrate such instructions, actions to be taken or status of the filling system 1. For example, the animated graphics portion 79 may illustrate graphics and/or text corresponding to the interconnection of the disposable 10 to the filling system 1 (e.g., graphics illustrating how to interconnect the disposable 10 to the mount 40 and/or that a disposable 10 needs to be interconnected to the filling system 1 to enable filling operations). The graphics portion 79 may illustrate a piston 14/piston drive member 32 engagement status (e.g., whether the piston 14 and piston drive member 32 are engaged and/or how to engage the piston and the piston drive member), a system prime status (e.g., whether the system is primed and/or how to prime the system), a direction of operation (e.g., advancement of the piston 14, retraction of the piston 14), a relative position of the piston 14 and/or piston drive member 32 (e.g., the static and/or dynamic position of the piston 14), the volume of medical liquid contained in the disposable 10 (e.g., the volume of medical liquid contained in the tubular member, static or dynamic), a velocity and/or torque status (e.g., the current advancement and/or retraction velocity and/or torque of the piston 14, static or dynamic), a pressure status (e.g., the current pressure within the tubular member 12 during advancement and/or retraction of the piston), an estimated amount of liquid contained in the medical liquid source(s) 60 and/or an amount of receptacle(s) 62 that can be filled prior to an estimated depletion of the medical liquid in the medical liquid source(s) 60, and/or a remaining number of receptacle(s) 62 to be filled. Other instructions and/or status information may also be illustrated by the graphics portion 79. For example, a recommended disposable size 10 and/or tubing size may be illustrated based upon the fluid-type parameter(s). Thus, the user interface 70 may be operable to indicate a instructions, to indicate an action to be taken to enable operation of the filling system 1 and/or to indicate a current status of the filling system 1, and therefore the user interface 70 may be interconnected to the controller 50 and operable to display various parameters, instructions and/or statistics.

Figure 12A:
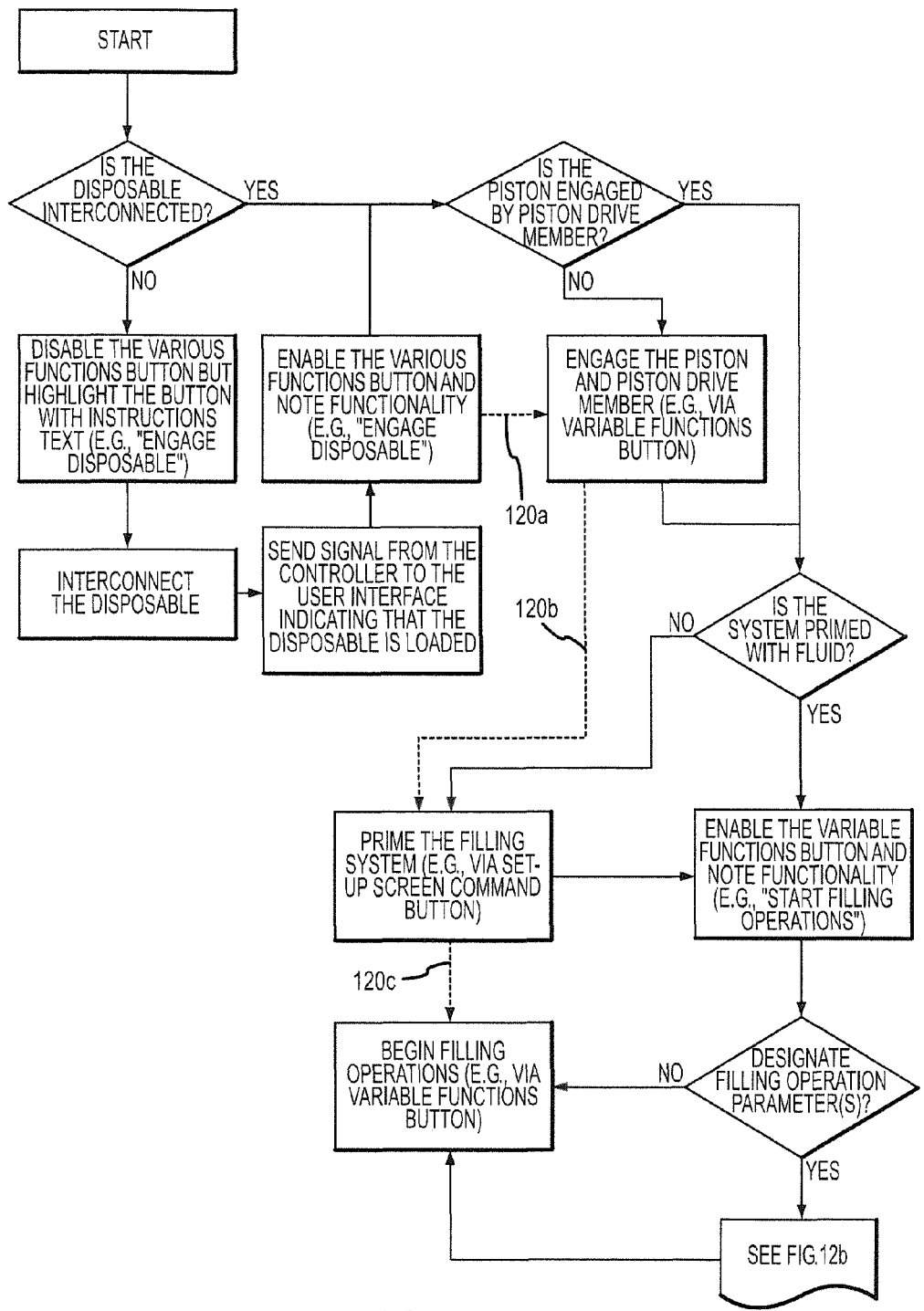
FIG. 12a is a flow chart illustrating one embodiment of a logic system employable with the controller and the user interface of FIGS. 1-2.
Figure 12B:
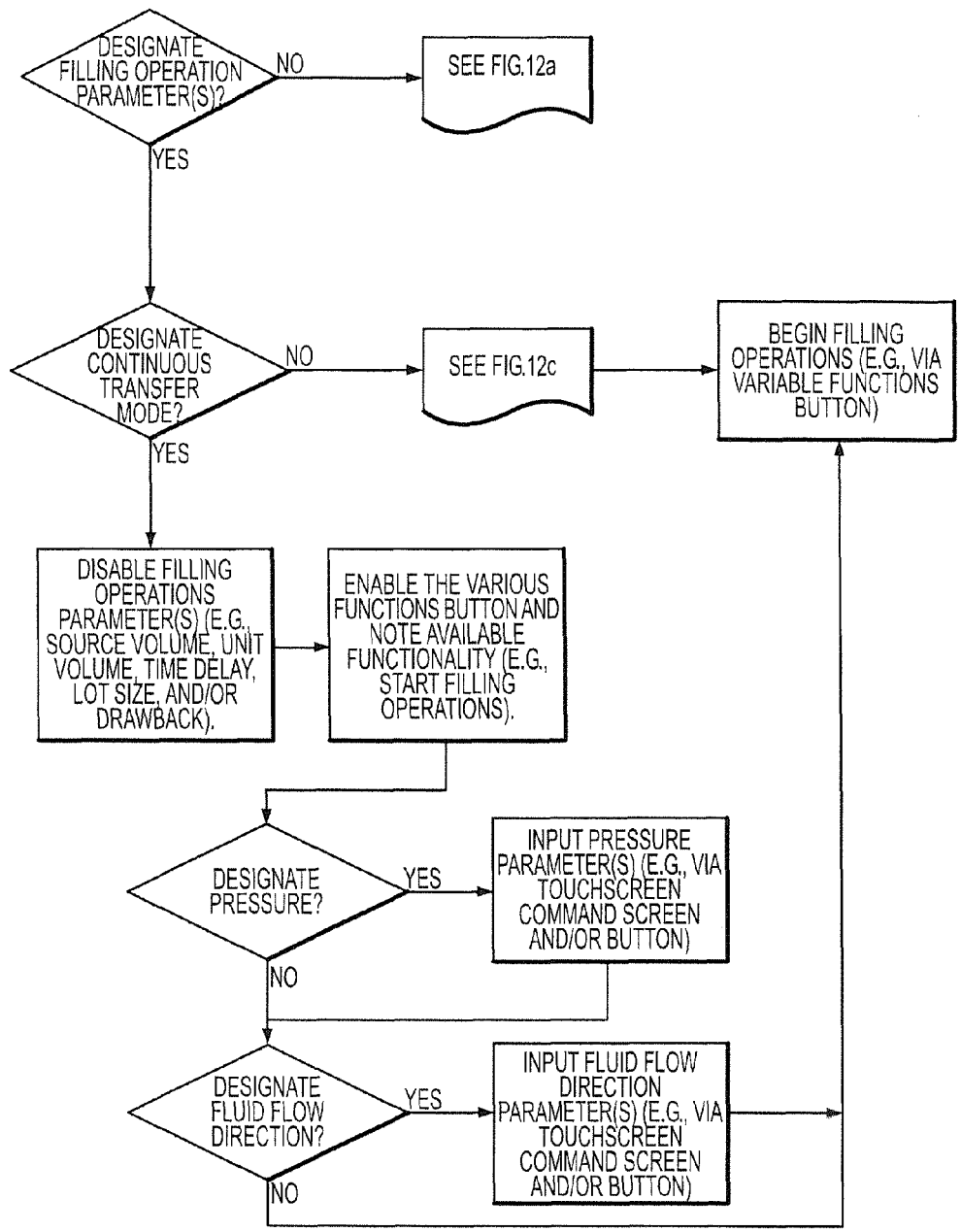
Figure 12C:
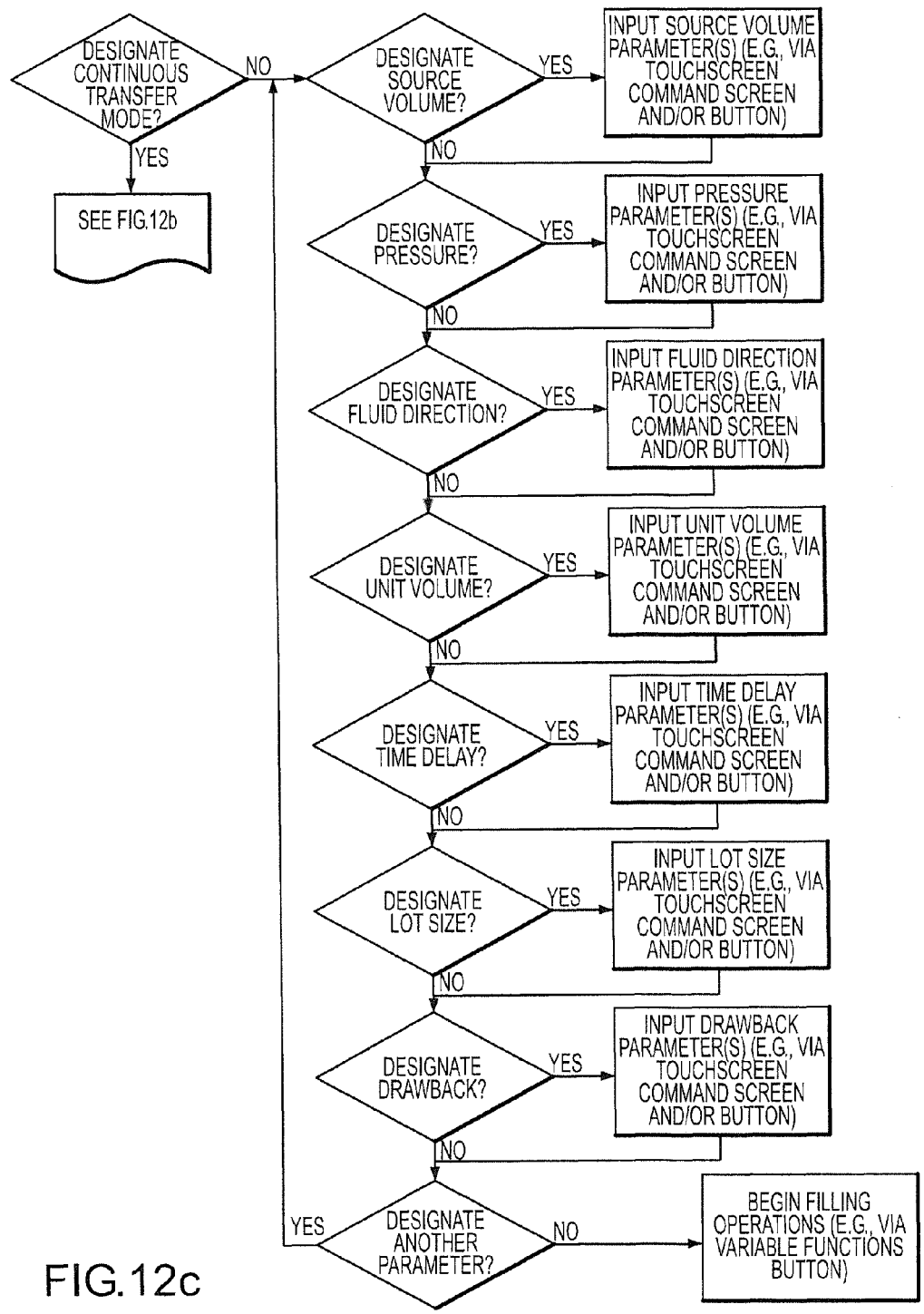

One embodiment of a logic system employable with the user interface 70 and controller 50 is now described in relation to FIGS. 12a-12c. Referring now to FIG. 12a, the logic system begins with determining whether the disposable 10 is interconnected to the mount 40. For example, the controller 50 may be interconnected to one or more switches on the mount 40 (e.g., one or more mechanical, optical and/or electrical switches) and when the disposable 10 is interconnected to the mount 40, the switches may be switched (e.g., via physical engagement with the disposable 10), whereupon the switches send one or more signals to the controller 50 indicating that the disposable 10 is interconnected to the mount 40.

If the disposable is not interconnected to the mount 40, the controller 50 may disable one or more operations of the filling system 1 and/or disable one or more buttons of the user interface 70 (e.g., the various functions button 78 of the main screen 71). Subsequent to determining that a disposable 10 is not interconnected to the mount 40, the controller 50 may further display an instruction on the main screen 71 indicating a necessary action to be taken for the filling system 1 to become operative. In one embodiment, the variable functions button 78 may be disabled and may include a label, such as "Load Disposable", to indicate that the disposable 10 should be interconnected to the mount 40. The above-described graphics portion 79 may also be utilized to indicate that the disposable 10 should be interconnected to the mount 40. After the disposable 10 is interconnected to the mount 40, a signal from the one or more switches on the mount 40 may be sent to the controller 50.

Upon establishing a physical interconnection between the disposable and the mount 40, the controller 50 may determine whether the piston 14 is engaged by the piston drive member 32. In this regard, the controller 50 may receive signals from the position sensor 38 or rotary encoder 2108 so that the controller 50 may determine the relative position of the piston drive member 32 in relation to the piston 14, as described above.

If the piston 14 is not engaged by the piston drive member 32, the controller 50 may display an instruction indicating a necessary action to be taken for the filling system 1 to become operable (e.g., via the variable functions button 78/graphics portion 79). In one embodiment, the variable functions button 78 may be enabled and may include a label, such as "Engage Disposable", to indicate that the variable functions button 78 should be utilized (e.g., pushed) so that the controller 50 may advance the piston drive member 32 to engage it with the piston 14 of the disposable 10. In one embodiment, the piston drive member 32 and piston 14 are advanced to a home advanced position upon activation of the variable functions button 7

The controller 50 may be aware that the piston 14 is not engaged by the piston drive member 32 without communicating with the position sensor 38 or rotary encoder 2108 (e.g., subsequent to the disposable being interconnected to the mount 40). In one embodiment, the controller 50 may automatically advance the piston drive member 32 to engage the piston 14 subsequent to the disposable 10 being interconnected to the mount 40, as illustrated via dashed line 120a. For example, the controller 50 may advance the piston drive member 32 and piston 14 to a home advanced position a predetermined time after receipt of the signals from the one or more switches indicating that the disposable 10 is interconnected to the mount 40.

After the piston 14 is interconnected with the piston drive member 32, the controller 50 may determine whether to prime the filling system 1 with fluid. In one embodiment, the controller 50 may await an input in relation to the above-described prime parameter(s) via the user interface 70 prior to priming the filling system 1. For example, after the disposable is interconnected to the mount 40, a user may activate the set-up screen button 72i (FIG. 11a), which calls the set-up screen 73 (FIG. 11b). A user may then activate the prime button 74d, which may activate one or more prime parameter(s), which may be provided to the controller 50. Upon receipt of the prime parameter(s), the controller 50 may prime the filling system 1, as described in further detail below.

In another embodiment, the controller 50 may be aware that the filling system 1 is not primed without receiving additional input. For example, the controller 50 may be aware that the disposable 10 was recently interconnected to the mount 40 and/or aware that the piston drive member 32 has not yet been advanced and/or retracted in relation to a predetermined disposable 10, and thus the controller 50 may determine that the filling system 1 is not primed. In turn, the controller 50 may prompt a user to input prime parameter(s) via the user interface 70 so that the controller 50 may determine whether it is necessary to prime the filling system 1. In another approach, the controller 50 may automatically prime the filling system 1 after determining that the filling system 1 is not primed (e.g., a predetermined amount of time after the interconnecting of the piston 14 and the piston drive member 32), as illustrated via dashed line 120b.

After the filling system 1 is primed, the filling system 1 may be utilized to for filling operations. In this regard, the controller 50 may display an instruction via the user interface 70 indicating that the filling system is operable to begin filling operations (e.g., via the variable functions button 78/graphics portion 79). In one embodiment, the variable functions button 78 may be enabled and may include a label, such as "Start", indicating that the variable functions button 78 may be utilized to signal the controller 50 to begin filling operations. In this regard, default parameter(s), discussed above, may be utilized by the controller 50 to conduct filling operations. In one embodiment, the controller 50 may begin filling operations without receiving an input from a user, as illustrated via dashed line 120c.

Prior to initiating filling operations, one or more fill-related parameter(s) may be provided to the controller 50. Referring now to FIG. 12b and as noted above, the user interface 70 may be operable to accept one or more fill-related parameter(s). For example, the user interface 70 may include continuous transfer mode parameter(s), discussed above. If the continuous transfer mode parameter(s) are activated (e.g., turned "on"), the controller 50 may disable one or more other fill-related parameter(s) (e.g., via graying out one or more corresponding button(s) on the user interface 70). For example, the controller 50 may disable one or more of the above-described source volume parameter(s), unit volume parameter(s), time delay parameter(s), lot size parameter(s), and drawback parameter(s) as such parameter(s) may not be necessary to operate the filling system 1 in the continuous transfer mode. The controller 50 may further enable one or more other fill-related parameter(s). For example, the controller 50 may enable one or more of the pressure parameter(s) and the fluid direction parameter(s) as such parameters may be useful in the continuous transfer mode. As may be appreciated, the filling system 1 may be operable in the continuous transfer mode without input from the above-mentioned other parameter(s) (e.g., via the default operating parameter(s)). After any input relating to the above-referenced other parameter(s), filling operations may be initiated (e.g., via the variable functions button 78).

When the continuous transfer mode parameter(s) is not activated/not designated, the controller 50 may enable the selection of a variety of other fill-related parameter(s). For example and with reference to FIG. 12c, the controller 50 may enable the selection of/designation of one or more of the above-described source volume parameter(s), pressure parameter(s), fluid direction parameter(s), unit volume parameter(s), time delay parameter(s), lot size parameter(s), and drawback mode parameter(s), to name a few. As may be appreciated, the filling system 1 may be operable to conduct filling operations without receiving an input related to any of the above-mentioned fill-related parameter(s). After input of any of the noted fill-related parameter(s), filling operations may be initiated (e.g., via the variable functions button 78).

Referring now back to FIGS. 1-2, one mode of operation of the automated medical liquid filling system 1 is described. First, preliminarily set-up procedures are completed, such as establishing interconnections between the disposable 10 and mount 40, between the disposable 10 and the medical liquid source(s) 60 (e.g., via the first fluid line 80), and between the second fluid line 82 and the disposable 10. In this regard, either of the first and second fluid lines 80, 82 may be fixedly interconnected to the disposable 10 prior to set-up (e.g., shipped interconnected to the disposable 10). Further, either of the first and second fluid lines 80, 82 may include connectors 81, 83 for interconnecting with the medical liquid source(s) 60 and receptacle(s) 62, respectively. For example, either of the connectors 81, 83 may be a spike connector or a complementary luer connector. Interconnection of spike connectors and luer connectors to various apparatus are described in U.S. Pat. No. 6,953,450, the contents of which are incorporated herein by reference in their entirety. Additionally, the valve 20 may be in the third position (e.g., a neutral position) upon interconnecting of the disposable 10 to the mount 40. As may be appreciated, when the valve 20 is in this third position, fluids from the first and second valve ports 26, 27 are restricted from entering the disposable 10.

Figure 13A:
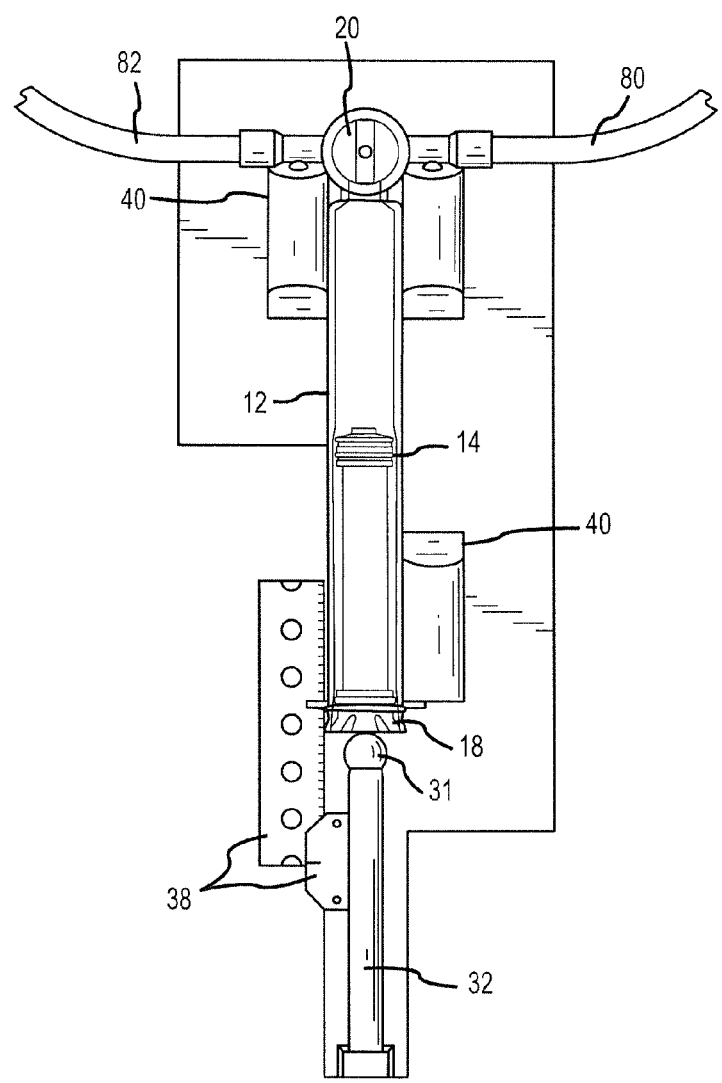
FIG. 13a is a top view of one embodiment of the disposable of FIG. 3a mounted to the drive system illustrating the valve in a shipping position and the piston in a fully retracted position.
Figure 13B:
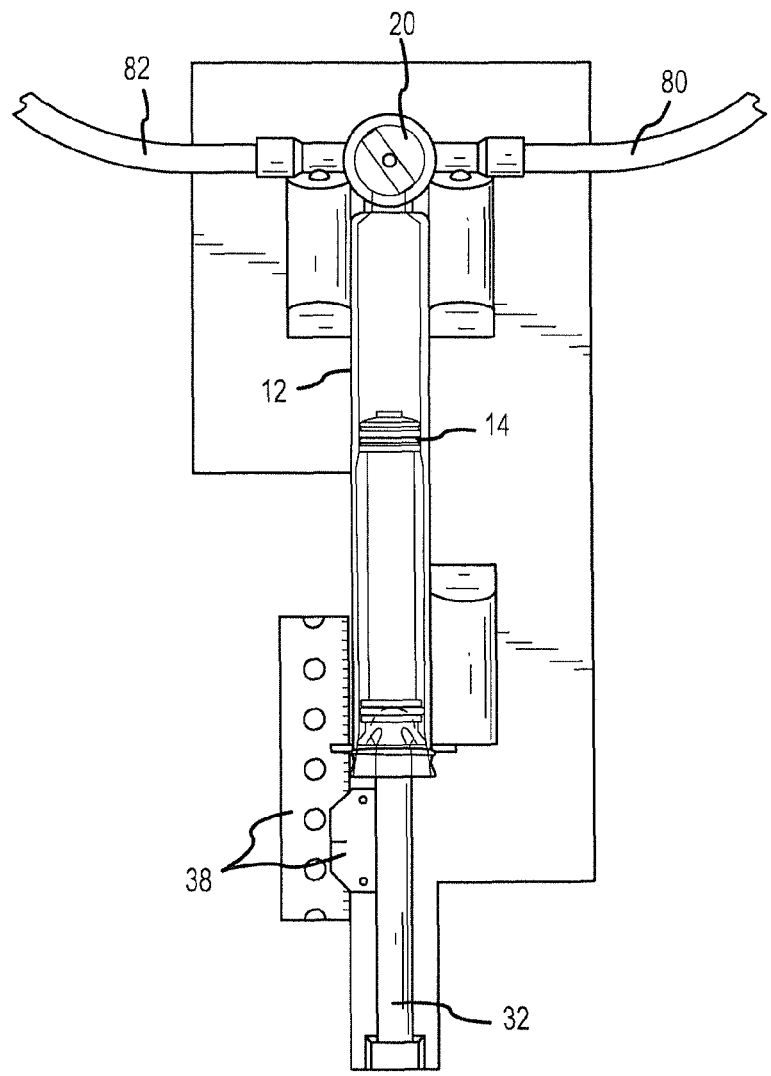
FIG. 13b is a top view of one embodiment of the disposable of FIG. 3a mounted to the drive system illustrating the valve in a second position and the piston in a home retracted position.

Next, the filling system 1 is primed with medical liquid from the medical liquid source(s) 60. More particularly and with reference to FIGS. 1-2 and 13a-13b, priming operations may be initiated using the user interface 70 (e.g., via the above-described prime parameter(s)) where the controller 50 may automatically or semi-automatically control the priming of the filling system 1. In one embodiment, the controller 50 may control the valve 20 to rotate it from the above-described third position, as illustrated in FIG. 13a, to the above-described second position as illustrated in FIG. 13b, to fluidly interconnect the second fluid line 82 to the tubular member 12 (e.g., via the second valve port 27). Thus, fluids located within the tubular member 12 (e.g., air and/or sterile gases used during shipment) may be removable from the tubular member 12 through the second fluid line 82 via advancement of the piston 14.

Concomitantly, the controller 50 may control the piston drive member 32 to engage it with the piston 14 of the disposable 10 as illustrated in FIG. 13b. More particularly, the piston drive member 32 may be advanced to interconnect with the piston 14 of the disposable 10 (e.g., via first connection member 18 and second connection member 31) to facilitate advancement and retraction of the piston 14.

Figure 13C:
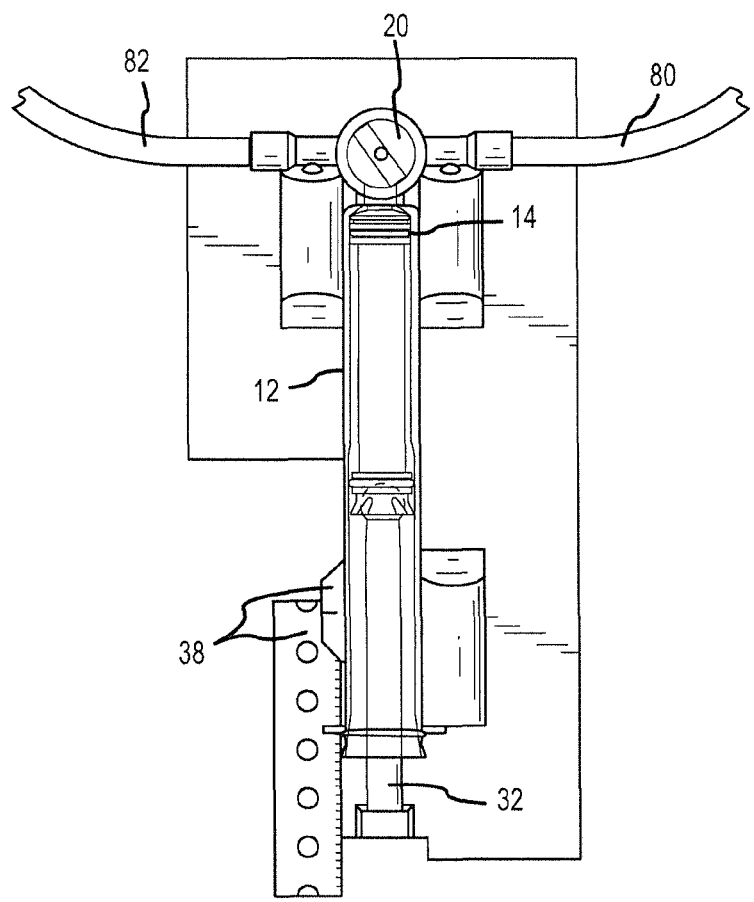
FIG. 13c is a top view of one embodiment of the disposable of FIG. 3a mounted to the drive system illustrating the valve in a second position and the piston in a fully advanced position.
Figure 13D:
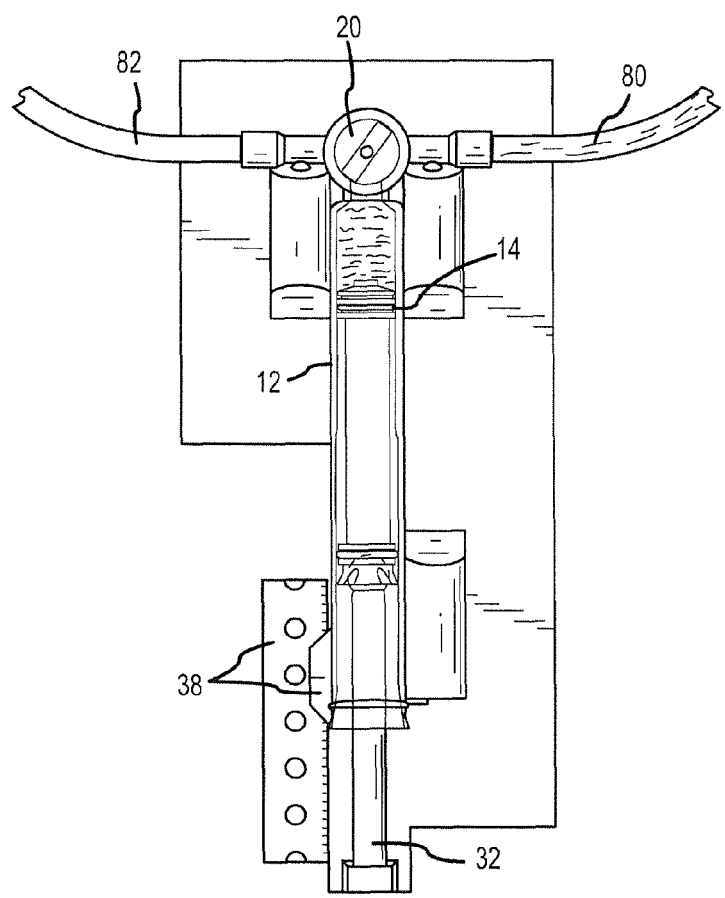
FIG. 13d is a top view of one embodiment of the disposable of FIG. 3a mounted to the drive system illustrating the valve in a first position and the piston disposed within a first portion of the tubular member.

Upon advancement of the piston 14 to the fully advanced position, as illustrated in FIG. 13c and which dispenses the above noted shipping fluids out of the disposable 10 via the second fluid line 82, the controller 50 may control the valve 20 to position it in the above-described first valve position to fluidly interconnect the tubular member 12 and medical liquid source(s) 60 (e.g., via the first fluid line 80 and first valve port 26). The controller 50 may then control the piston drive member 32 to retract the piston 14 to draw medical fluids from the medical liquid source(s) 60 into the first fluid line 80 and tubular member 12, as illustrated in FIGS. 13d-13e.

Figure 13E:
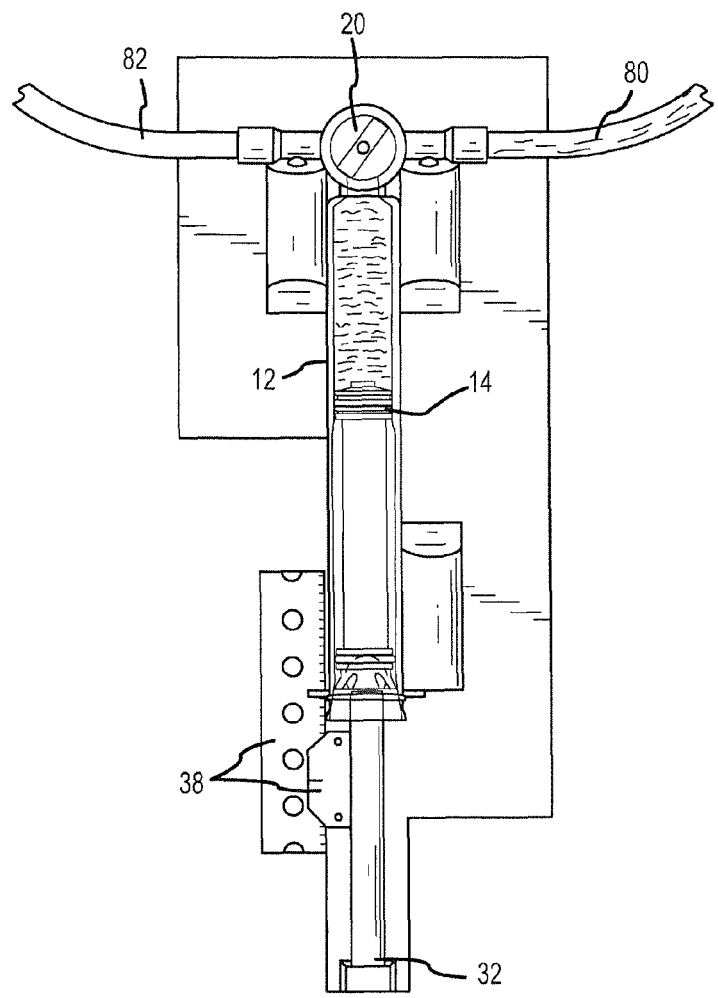
FIG. 13e is a top view of one embodiment of the disposable of FIG. 3a mounted to the drive system illustrating the valve in the first position and the piston in a home retracted position.
Figure 13F:
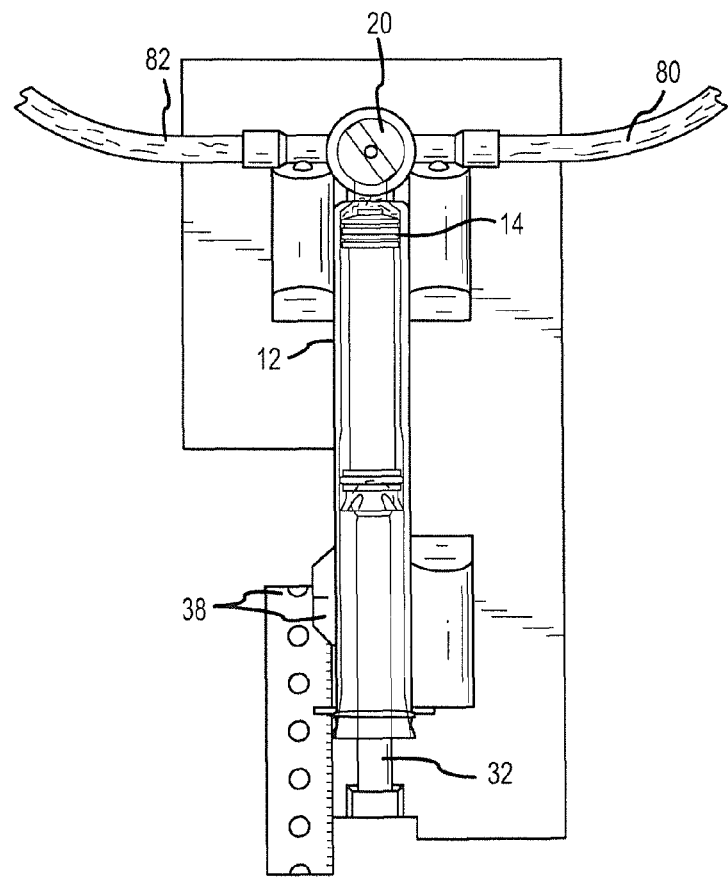
FIG. 13f is a top view of one embodiment of the disposable of FIG. 3a mounted to the drive system illustrating the valve in the second position and the piston in a home advanced position.

After a desired amount of medical liquids has been drawn into the tubular member 12, one embodiment of which is illustrated in FIG. 13e, which illustrates the piston 14 retracted to the home retracted position to fill the tubular member 12 with a relatively large amount of fluid, the controller 50 may control the valve 20 to position it in the second valve position, as illustrated in FIG. 13f, to fluidly interconnect the tubular member 12 to the second fluid line 82 (e.g., via second valve port 27). The controller 50 may then control the piston drive member 32 to advance the piston 14 to dispense medical liquids contained in a tubular member 12 through the second fluid line 82. The above processes may be repeated as necessary until the tubular member 12, first fluid line 80 and second fluid line 82 are "primed" (e.g., substantially full of medical liquid). Thus, the filling system 1 may be operated a plurality of times (e.g., the piston drive member 32 may be advanced and retracted relative to the tubular member 12 a plurality of times) while maintaining the interconnections between the disposable 10 and the drive system 30, while maintaining the interconnections between the medical liquid source(s) 60 and the disposable 10 and while maintaining the seal of the tubular member via the seal member 16.

Although the priming operation discussed above and in FIG. 13e describe the piston 14 retracted to the home retracted position to fill the tubular member 12, shorter piston strokes may be utilized during the priming operation. Shorter piston strokes, as opposed to moving the piston 14 to the home retracted position, during priming may result in less medical liquid being used during the priming operation. For example, if full strokes (e.g., between the home retracted and home advanced positions) are used during the priming operation, it is possible that the medical liquid may begin to enter the tubular member 12 while the piston 14 is relatively close to the valve 20. If the piston 14 is continued to be drawn back in such a situation, the entire volume of medical liquid that is drawn into the tubular member 12 may be unusable since it is mixed with the gas that was within the tubular member 12 prior to the entry of the medical liquid into the tubular member 12. In contrast, if relatively short strokes (e.g., between the home advanced position and a second position between the home advanced position and the home retracted position) are used during the priming operation, when the medical liquid first enters the tubular member 12, the additional amount of liquid drawn into the tubular member 12 will be less than the amount drawn if the piston 14 were to be drawn all the way to the home retracted position. Similarly, the use of piston strokes shorter than the entire distance between the home advanced position and the home retracted position may be beneficial when flushing the automatic fluid filling system 1, for example, when changing the medical liquid source(s) 60.

After the priming, the second fluid line 82 may be fluidly interconnectable to the receptacle(s) 62. More particularly, the second fluid line 82 may be interconnected to a second dispensing apparatus designed for the dispensing of medical liquids to the receptacle(s) 62. For example, the second fluid line 82 may be interconnected to one or more of a nozzle, needle, luer connector or other apparatus adapted to dispense medical liquid into a receptacle.

In one embodiment, the second dispensing apparatus may comprise a stand and corresponding luer connector adapted to receive and interconnect with the receptacle(s) 62, and such receptacle(s) 62 may comprise syringes. In this regard, the luer connector (e.g., a RAPID-FILL connector, available from Baxa Corporation, Englewood, Colo., U.S.A.) may be restrictedly interconnected to the stand (e.g., a Syringe Filling Fixture, available from Baxa Corporation, Englewood, Colo., U.S.A.) with the second fluid line 82 being fluidly interconnected to a first end of the luer connector. A syringe may be fluidly interconnected with a second end of the luer connector, whereupon the filling operations may be undertaken, as described below, to dispense a predetermined amount of a medical liquid into the syringe. The syringe may then be fluidly disconnected from the luer connector and a subsequent syringe may be interconnected to the filling system 1 via the luer connector. Filling operations may be repeated as desired until a desired/predetermined amount of syringes are filled.

After the second fluid line 82 is interconnected to the receptacle(s) 62 and any necessary fill-related parameter(s) have been input (e.g., via the main screen 71 of the user interface 70), the medical filling system 1 may be utilized to conduct filling operations.

Referring again to FIGS. 1-2, the automated medical liquid filling system 1 may include self-diagnostic and self-calibration capabilities. These capabilities may include diagnostic and calibration routines that may be run at various times including prior to or in conjunction with priming operations. The self-diagnostic and calibration capabilities may also include the ability to monitor the performance of the automated medical liquid filling system 1 during any or all operations to determine if the performance of the automated medical liquid filling system 1 is outside of acceptable parameters. The self-diagnostic and calibration capabilities may also include the ability to monitor the performance of the automated medical liquid filling system 1 to detect trends that may indicate future component or system functionality degradation.

An embodiment of the self-diagnostic and calibration capabilities of the automated medical liquid filling system 1 that may be performed prior to any filling operations will now be described. After interconnection of the disposable 10 with the mount 40, the piston drive member 32, and the valve drive member 34, the valve drive member 34 may be positioned to fluidly interconnect the tubular member 12 with either the first valve port 26 or the second valve port 27. The piston 14 may then be fully advanced (such as illustrated in a FIG. 4d) within the tubular member 12. The valve stem 24 may then be placed into the third valve position (e.g., the neutral position). The piston 14 may then be drawn away from the fully advanced position to a first reference point between the fully advanced position and the home retracted position. If the piston 14 and valve 20 are functioning properly, a reference vacuum may be created when the piston 14 is at the first reference point. The next step may be to draw back the piston 14 to a second reference point between the first reference point and the home retracted position. The automated liquid filling system 1 may measure a parameter (e.g., average current supplied to the motor 36a) related to the movement of the piston 14 between the first reference point and the second reference point. This measurement may be used to calibrate the automated liquid filling system 1 for the particular atmospheric pressure of the environment in which the automated liquid filling system 1 is operating. Since the level of vacuum being produced within the tubular member 12 is known and the force used to move the piston 14 from the first reference point to the second reference point is known, the atmospheric pressure exerted on the system can be determined. Another method of calibration may include using the motor 36a to impart a constant retracting force on the piston 14 for a predetermined amount of time and measuring the amount of displacement of the piston 14 during that predetermined amount of time. The amount of displacement may then be correlated to the atmospheric pressure surrounding the automated liquid filling system 1.

The automated liquid filling system 1 may also be operable to determine the frictional forces associated with moving the piston 14 within the first portion 12a of the tubular member 12. This may be accomplished by fluidly interconnecting the tubular member 12 to either the first valve port 26 or the second valve port 27 and having the valve port to which the tubular member is fluidly interconnected open to the local atmosphere. The drive system 30 may then move the piston 14 within the first portion 12a of the tubular member 12 and measure the current required by the motor 36a to move the piston 14 over a given distance. This current measurement can be correlated to the frictional force associated with movement of the piston within the first portion 12a of the tubular member 12.

Therefore, as described, the automated liquid filling system 1 may be calibrated in relation to local atmospheric pressure and the frictional forces related to the movement of the piston 14. If during the calibration procedure a measured parameter (e.g., average current supplied to the motor 36a) falls outside of acceptable values, an alarm may sound or an alert may be displayed to inform a user of the unacceptable results. For example, if the average current supplied to the motor 36a while moving from the first reference point to the second reference point falls below a predetermined value, it may be inferred that either the valve stem 24, the piston 14, or a combination thereof are not sealing properly. An alert may then be displayed for the user to replace the disposable 10. Similarly, if the average current supplied is above a predetermined value, it may be inferred that frictional forces are higher than acceptable and the user may be alerted to replace the disposable 10. In another example, if the average current supply to the motor 36a while moving the piston 14 during the frictional force calibration falls below a predetermined value, it may be inferred that the piston resilient member the 15 is not adequately engaged with the wall of the tubular member 12 and therefore the user may be alerted to replace the disposable 10.

The frictional and atmospheric conditions determined in the above described calibration steps may be used to partly determine operational parameters of the automatic liquid filling system 1. For example, it may be desired to maximize the speed of the piston 14 while drawing medical liquid from the medical liquid source(s) 60. However, it may also be desirable to avoid foaming, bubbles or cavitation within the tubular member 12 that may be caused by the relatively low pressure within the tubular member 12 while the piston 14 is being drawn back. Since cavitation is partially determined by pressure and the medical liquid source(s) 60 may be under local atmospheric pressure, the point at which a particular medical liquid may cavitate may be related to the local atmospheric pressure. Since the above-described procedure may determine local atmospheric pressure, the automatic liquid filling system 1 may be operable to determine a maximum piston velocity that can be attained without significant cavitation within the medical liquid.

The automatic liquid filling system 1 may also possess other diagnostic capabilities. The automatic liquid filling system 1 may be operable to detect leaks within the disposable 10 and attached tubing. For example, prior to fluidly interconnecting the first fluid line 80 with a medical liquid source(s) 60 and prior to fluidly interconnecting the second fluid line 82 with a medical liquid receptacle(s) 62, the first and second fluid lines 80, 82 may be capped or sealed. The valve stem 24 may be positioned to fluidly interconnect to the tubular member 12 with the first fluid line 80. The piston 14 may then be moved within the tubular member 12 and the current required by the motor 36a to move the piston 14 they be measured. Since the first fluid line 80 is sealed, there should be a resistance to movement of the piston 14 due to a vacuum (if the piston 14 is drawn back) or a pressure build up (if the piston 14 is moved forward) that should be reflected in the amount of current required by the motor 36a. This procedure may be repeated with the valve stem 24 positioned to fluidly interconnect the tubular member 12 with the second fluid line 82. This procedure may be repeated with the valve stem 24 positioned in the neutral position. Any detected errors and when those errors were detected may be used to determine possible locations of system leaks. For example, if an error is detected when the first fluid line 80 is fluidly interconnected to the tubular member 12 but not when the second fluid line 82 is fluidly interconnected to the tubular member 12, it may be inferred that the leak is related to the first fluid line 80. Conversely, if an error is detected when the second fluid line 82 is fluidly interconnected to the tubular member 12 but not on the first fluid line 80 is fluidly interconnected to the tubular member 12, it may be inferred that the leak is related to the second fluid line 82. If an error occurs under all situations, it may be inferred that the error is related to the tubular member 12 or valve 20. The above procedures may be used to determine likely locations of system leaks. However, other system leaks or error sources may be present. When any error is detected or any reading is outside of a predetermined range, an alarm or alert may be provided to inform a user of a system fault. Furthermore, the system may direct the user to the most likely location of the problem. The alarm or alert may be presented at the automatic liquid filling system 1 and may be in the form of a visual display, an audible signal, or a combination thereof. The alarm or alert may also be presented in any device, such as a PC (including remote PCs), interconnected to the automatic liquid filling system 1.

Additionally, system diagnostics may also be operative during automatic liquid filling system 1 operation. For example, during operation the automatic liquid filling system 1 may monitor the current required by motor 36a to move the piston 14 during various drawing and dispensing operations. If a gradual increase in the current required to draw back the piston 14 is detected, but no change in the current required to move the piston 14 foreword is detected, it may be inferred that a clog may be developing in the first fluid line 80 or in a member, such as the filter 201, interconnected to the first fluid line 80. Once such a situation is detected, an alarm or alert may be generated to inform the user of the potential clog. Similarly, if a gradual increase in the current required to move the piston 14 foreword is detected but no change in the current required to draw back the piston 14 is detected, it may be inferred that a clog may have developed in the second fluid line 82 or in a member interconnected to the second fluid line 82.

A sudden increase in the current required to move the piston 14 within the first portion 12a of the tubular member 12 may indicate a sudden blockage, such as a kink in a fluid line. The probable location of the sudden blockage may be determined in a fashion similar to that described above and an alarm or alert may be issued to inform the user of the situation and of the probable location of the problem.

A gradual decrease in the current required to move the piston 14 within the first portion 12a of the tubular member 12 may indicate a growing leak in the automated liquid filling system 1. A sudden decrease in the current required to move the piston 14 may indicate a fast developing leak or that a component has become disconnected. The probable location of the problem may be determined and communicated to a user in a fashion similar to that described above.

Figure 14:
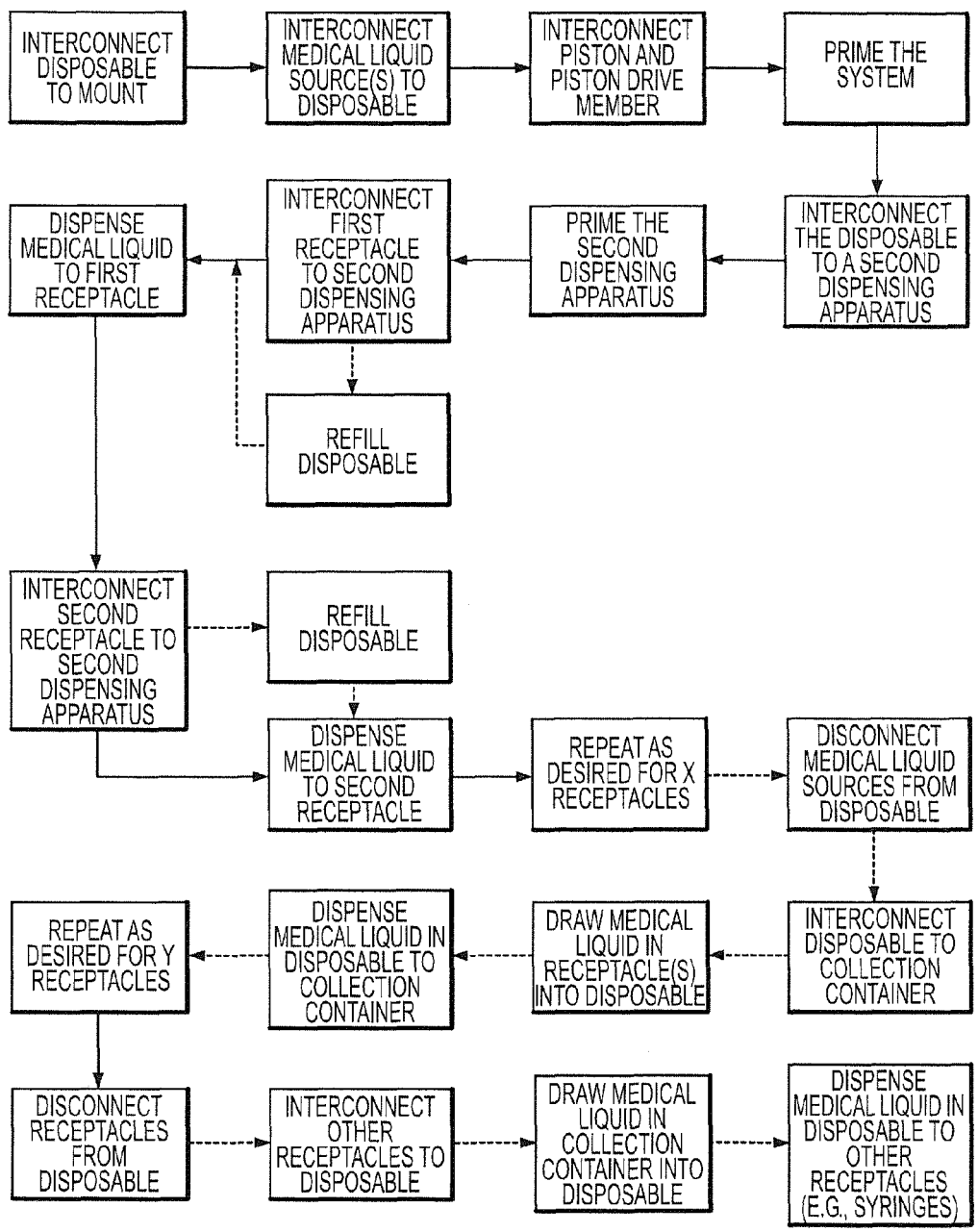
FIG. 14 is a flow chart illustration one mode of operation of a medical liquid filling system of an embodiment of the present invention.

One filling operations method is now described in relation to FIG. 14. After a physical interconnection between the disposable 10 and mount 40 has been established, as described above, the medical liquid source(s) 60 may be interconnected to the disposable 10, as described above (e.g., via the first fluid line 80). The piston 14 may then be interconnected with the piston drive member 32, after which the system may be primed, such as described above. After the system is primed, the disposable 10 may be interconnected to a second dispensing apparatus, as described above (e.g., a needle). After the second dispensing apparatus is interconnected to the disposable 10, it may be primed, such as described above. Next a first receptacle of the receptacle(s) 62 (e.g., a vial containing a dry powder) may be interconnected to the second dispensing apparatus, and thus fluidly interconnectable to the disposable 10, after which the medical liquid (e.g., pharmaceutical quality water) contained in the tubular member 12 may be dispensed to the first receptacle, such as described above (e.g., via rotation of the valve to the second position and advancement of the piston 14). Prior to dispensing medical liquid to the first receptacle, the tubular member 12 may be refilled, such as described above (e.g., via rotation of the valve 20 to the first position and retraction of the piston 14).

After the first receptacle is filled, the piston 14 may be retracted (not illustrated) in accordance with the drawback parameter(s), to draw non-dispensed liquid back into the filling system 1, as described above. Additionally, the piston 14 may be retracted and advanced (e.g., utilizing the piston drive member 32) any number of times (not illustrated) to mix the solution contained in the first receptacle. Subsequently, a second receptacle may be interconnected to the second dispensing apparatus, and thus fluidly interconnectable to the disposable 10, after which a medical liquid may be dispensed to the second receptacle. Prior to dispensing medical liquid to the second receptacle, the tubular member 12 may be refilled, such as described above. These processes may be repeated, as desired, for any number of receptacles to provide receptacles containing a desired volume of a medical liquid.

Other optional filling operations may also be undertaken after a desired number of receptacles have been filled. For example and with further reference to FIG. 14, the filled receptacles may comprise a first medical liquid. After a desired number of receptacles have been filled, the medical liquid source(s) 60 may be disconnected from the disposable (e.g., via disconnection of the first fluid line 80 from the medical liquid source) and the disposable may be interconnected to a collection container (e.g., via the first fluid line 80). Next, the fluid flow direction may be changed, wherein the disposable 10 draws the first medical liquid from the receptacles into the tubular member. This first medical liquid in the tubular member 12 may then be dispensed to the collection container. This process may be repeated for any number of receptacles containing the first medical liquid. Thus, the collection container may be filled with a first medical liquid.

Further optional filling operations may also be undertaken. For example, and with further reference to FIG. 14, after the collection container is filled, receptacles may be disconnected from the disposable (e.g., via disconnection of the second fluid line 82 from a needle) and other receptacles may be interconnected to the disposable 10 (e.g., via the second fluid line 82 and a second dispensing apparatus, such as a stand and corresponding luer connector). The fluid flow direction may again be changed, wherein the first medical liquid contained in the collection container may be drawn into the disposable and subsequently dispensed to these other receptacles (e.g., syringes) to provide a receptacle containing a preselected volume of the first medical liquid.

In one approach, the filling system 1 may be utilized to fill the receptacle(s) 62 with a medical liquid from the medical liquid source(s) 60 to produce a liquid medication of a desired volume in each of the receptacle(s) 62. That is, the filling system 1 may be utilized to produce a desired volume of liquid medication in each of the receptacle(s) 62. To achieve the filling of the receptacle(s) 62, the tubular member 12 may be filled with various volumes of medical liquid. In one approach, the tubular member 12 may be filled with a sufficient volume of medical liquid to fill a plurality of the receptacle(s) 62 without refilling the tubular member 12. For example, the tubular member 12 may be filled with a relatively large quantity of medical liquid via retraction of the piston 14 and piston drive member 32 (e.g., retraction from the home advanced position to the home retracted position). Subsequently, the piston 14 may be advanced to dispense a quantity of medical liquid to a first receptacle (e.g., via advancement from the home retracted position to a first position). After a second receptacle is in position to be filled, the piston 14 may again be advanced to dispense a quantity of medical liquid to this second receptacle (e.g., via advancement from the first position to a second position). As may be appreciated, these processes may be repeated until a desired quantity of receptacle(s) 62 are filled or the tubular member 12 no longer contains sufficient medical liquid to fill the next receptacle with a desired amount of medical liquid. The piston 14 may then be retracted to fill the tubular member 12 with a desired amount of medical liquid. As may be appreciated, the piston 14 may be advanced and retracted any number of times to fill the tubular member 12 until a desired amount of receptacle(s) 62 are filled or until the medical liquid source(s) 60 are depleted of sufficient amount of medical liquid.

In another approach, the tubular member 12 may be filled with a sufficient volume of medical liquid to fill a single receptacle. For example, the tubular member 12 may be filled with a predetermined quantity of medical liquid via retraction of the piston 14 (e.g., retraction from the home advanced position to another position). Subsequently, this predetermined quantity of medical liquid may be dispensed to a receptacle (e.g., via advancement from the another position to the home advanced position). As may be appreciated, this process may be repeated as necessary until a desired amount of receptacle(s) 62 are filled or until the medical liquid source(s) 60 are depleted of sufficient amount of medical liquid.

During filling operations, the controller 50 may be operable to determine whether sufficient volume of medical liquid is contained within the tubular member 12 to fill a next one of the receptacle(s) 62. Partially filling one of the receptacle(s) 62, subsequently refilling the tubular member 12 and then completing filling of the one of the receptacle(s) 62 may lead to an inaccurate volume of medical liquid dispensed. Thus, in one embodiment, when the controller 50 determines that insufficient volume of medical liquid is contained within the tubular member 12, the controller 50 automatically refills the tubular member 12 prior to dispensing a medical liquid to a next one of the receptacle(s) 62.

Any number of medical liquids may be moved to and from any number of medical liquid source(s) 60 and receptacle(s) 62. In this regard, the optional manifold 64 may be utilized to facilitate filling operations. Moreover, the valve 20 may include any number of ports, passageways and/or channels and any number of fluid lines may be interconnected to the valve 20 and/or the optional manifold 64 to facilitate filling operations. Additionally, the first and second fluid lines 80, 82 may be a single line or may comprise a plurality of lines, such as a bifurcated and/or a trifurcated tubing set, which may be interconnected to any number of medical liquid source(s) 60 and/or receptacle(s) 62. Also, the user interface 70 and/or controller 50 may be utilized to initiate, control and/or conduct any one of the above-described filling operations.

Heretofore, the filling system 1 has generally been described in relation to flow of fluids via a first flow path (e.g., from the medical liquid source(s) 60 through the disposable 10 and to the receptacle(s) 62). Additionally, filling operations may be conducted by the filling system 1 to flow medical liquids in another flow path. In one approach, the receptacle(s) 62 may contain a medicine-containing substance (e.g., a dry powder) and the medical liquid source(s) 60 may contain a solvent. After addition of a desired amount of the solvent to the receptacle(s) 62, it may be useful to mix the composition contained within the receptacle(s) 62 to achieve a desired liquid medication. Thus, the piston 14 may be retracted and advanced one or more times to achieve a desired mixing, after which the piston 14 may be advanced to dispense the composition to the receptacle(s) 62.

As noted above, the controller 50 may be operable to automatically or semi-automatically control various operations of the filling system 1. The controller 50 may also be operable to assist in detecting leaks or occlusion within the filling system. As may be appreciated, the back pressure applied to the piston 14 during dispensing operations (e.g., advancement of the piston 14) is generally related to the viscosity of the utilized medical liquid as well as the hydraulic nature of the interconnections. Correspondingly, the draw pressure created during draw operations (e.g., retraction of the piston 14) is also generally related to the viscosity of the utilized medical liquid as well as the hydraulic nature of the interconnections. If the interconnections of the filling system 1 are appropriately connected and no appreciable leaks are present within the system, a particular back pressure/draw pressure will be created. However, if one or more interconnections are not appropriately connected and/or an appreciable leak is present within the filling system 1 a smaller back pressure/larger draw pressure will occur. Correspondingly, if one or more components are occluded, a larger back pressure/smaller draw pressure will occur. As the velocity of the piston 14 is related to this back pressure/draw pressure and because the velocity of the piston 14 may be calculable (e.g., via position sensor 38 or rotary encoder 2108), the controller 50 may be operable to determine whether an appropriate back pressure/draw pressure is occurring, and therefore operable to determine whether a leak or occlusion is present within the filling system 1.

More particularly, the controller 50 may be operable to receive (e.g., via the user interface 70) one or more detection parameters ("detection parameter(s)"), such as parameters associated with one or more of the viscosity of the medical liquid, the diameter(s) of one or more interconnected components (e.g., the first and second fluid lines 80, 82, a second apparatus connected to the second fluid line 82, the medical liquid source(s) 60) and/or a diameter of the tubular member 12. As may be appreciated, such detection parameter(s) may correspond with or be equivalent to one or more fill-related parameters. Utilizing such detection parameter(s) and the pressure parameter(s), described above, the controller 50 may be operable calculate a normal back pressure in relation to dispensing operations and a normal draw pressure in relation to draw operations. The controller 50 may also be operable to calculate a current operating pressure, as described above, and may be operable to compare the calculated normal back pressure/draw pressure to the current operating pressure. If the current operating pressure is not within a desired range of the normal back pressure/draw pressure, as appropriate, the controller 50 may be operable to indicate such status and the controller 50 may take appropriate action. For example, the controller 50 may automatically cease filling and/or priming operations and/or may indicate a leak or occlusion has been detected (e.g., via the user interface 70).

Figure 15:
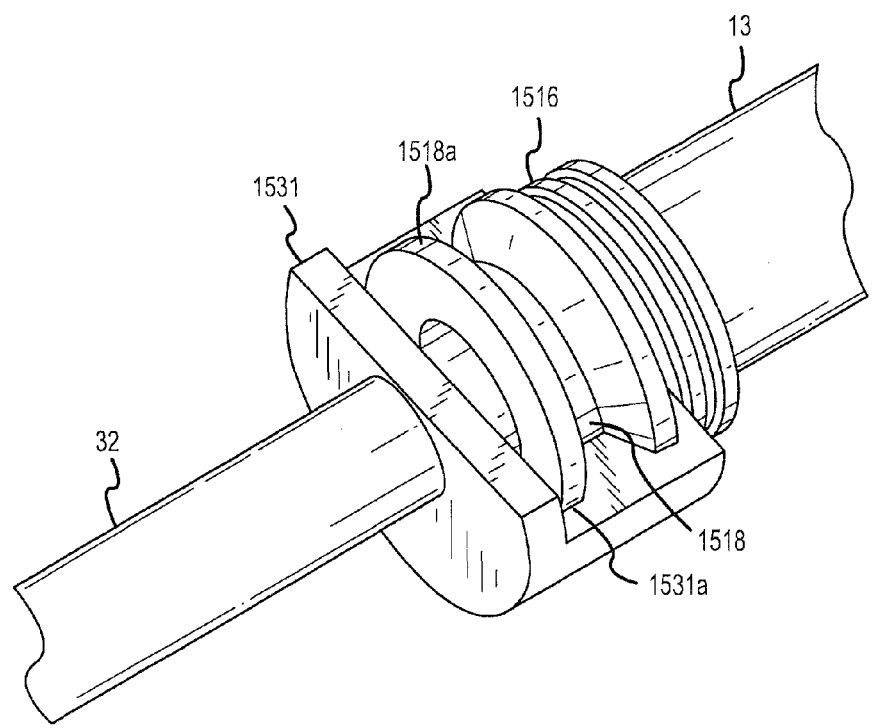
FIG. 15 is a perspective view of one embodiment of a female-male interconnection arrangement.

As noted above, the piston 14 and a piston drive number 32 may be interconnected by first and second connection members 18, 31, respectively. As also noted above, one of the first and second connection members 18, 31 may comprise a complementary female member, and the other of the first and second connection members may comprise a complementary male member. Another embodiment of such a female member/male member interconnection arrangement is provided in FIG. 15. In the illustrated embodiment, the piston drive member 32 is interconnected to a female member 1531, the female member including a plurality of slots 1531a, each of the plurality of slots being adapted to receive a corresponding one of a plurality of disks 1518a of the male member 1518. The male member 1518 may also be interconnected to a seal member 1516 and/or a rod 13, and the rod 13 may interconnect the male member 1518 to the piston 14 (not illustrated). As the disposable 10 is interconnected to the mount 40 (e.g., via push and snap action), the disks 1518a of the male member 1518 may be moved toward and slide into the corresponding slots 1531a of the female member 1531, thereby restrictively interconnecting the piston 14 to the piston drive member 32. To disconnect the connection members 1518, 5131, the disks 1518a may be moved away from the slots 1531a (e.g., via an upward force).

In another embodiment, the female member may comprise a spring portion that acts as a one-way snap to facilitate interconnection between the female and male members. In this regard, the female member may be located within the tubular member 12. As the male member (e.g., a bulbous end portion) is advanced into the female member, the spring portion is compressed allowing the male member to enter and engage the female member. When the male member is advanced a predetermined amount, the spring member may no longer engage the male portion and may spring back to its original position. As the male member is retracted, the spring portion restrictively engages an end of the male portion, thereby restricting removal of the male portion from the female portion and facilitating co-movement of the female and male portions. To disconnect the female and male portion, the female portion may be positioned in another diameter of the tubular member 12 or removed from the tubular diameter, whereupon the female member may expand enabling the male member to be removed from the female member. In another embodiment, the male member may comprise a screw and the female member may comprise corresponding threads.

As may be appreciated, the female and male connection members may comprise a toleration size to facilitate interconnection. These toleration sizes may be known by the controller 50 (e.g., hard coded or via input via the user interface 70) to facilitate the determination of appropriate movement of the piston 14 and/or piston drive member 32. Also, the piston drive member 32 may thus move a small amount prior to physically interconnecting with the piston 14 for co-movement therewith.

Figure 16:
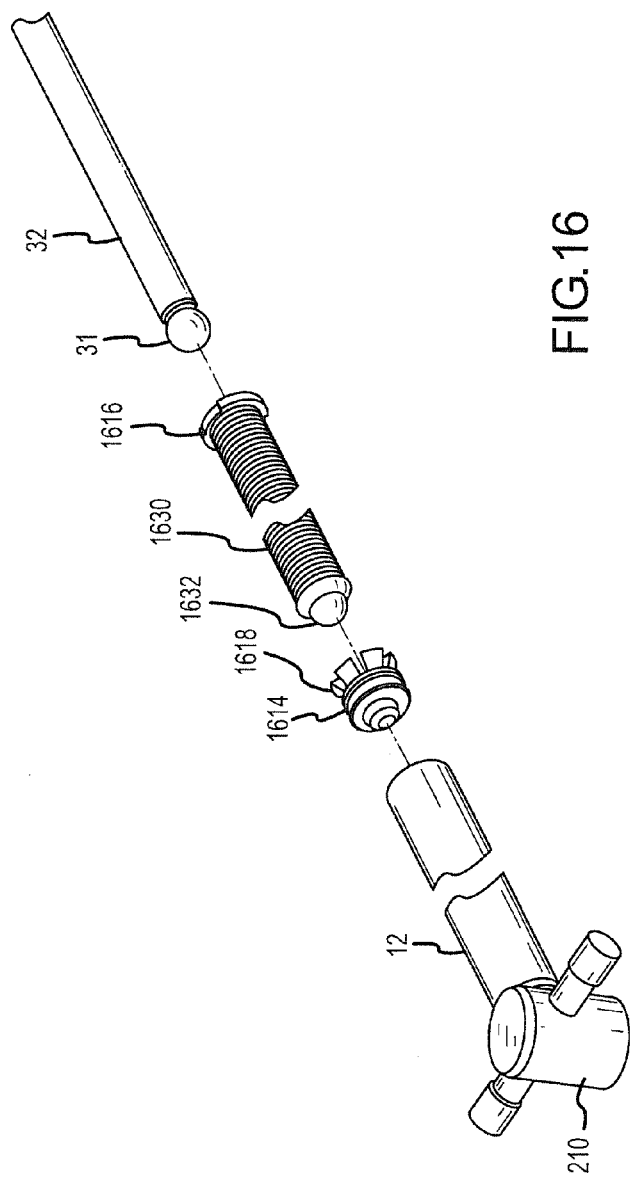
FIG. 16 is a perspective exploded view of one embodiment of a disposable and piston drive member including a bellows arrangement.

As also noted above, it is desirable to restrict the portions of the tubular member 12 that fluidly communicate with the medical liquids from communicating with the outside air and/or other contaminants (e.g., particles). In one embodiment, and as noted above, the piston 14 and seal member 16 may be spaced a fixed distance from one another to restrict such outside materials from fluidly communicating with the portions of the tubular member 12 that fluidly communicate with the medical liquids. In another embodiment and as illustrated in FIG. 16, a bellows 1630 may be used to restrict contamination of the tubular member 12. In this embodiment, the piston 1614 is interconnectable to a bellows 1630 via a first connection member 1618 and a mating bellows connection member 1632. The piston drive member 32 is interconnectable to the piston 1614 via a second connection member 31 and the mating bellows connection member 1632. In this regard, the mating bellows connection member 1632 may be one of a first male or female connection member, the second connection member 1631 may be the same of the male and female connection member, but of a smaller proportionate size, and the first connection member 1618 may be the other of a first male or female connection member. A seal member 1616 may be provided on the distal end of the bellows 1630 for sealing a distal end of the tubular member when such bellows 1630 and piston 14 are disposed within the tubular member 12. In this regard, the seal member 1616 may be a closed-cell foam material adapted to sealably engage inner surfaces of the tubular member 12 to restrict entry of contaminants into the tubular member 12 when such seal member 1616 is disposed within the tubular member 12.

Figure 20:
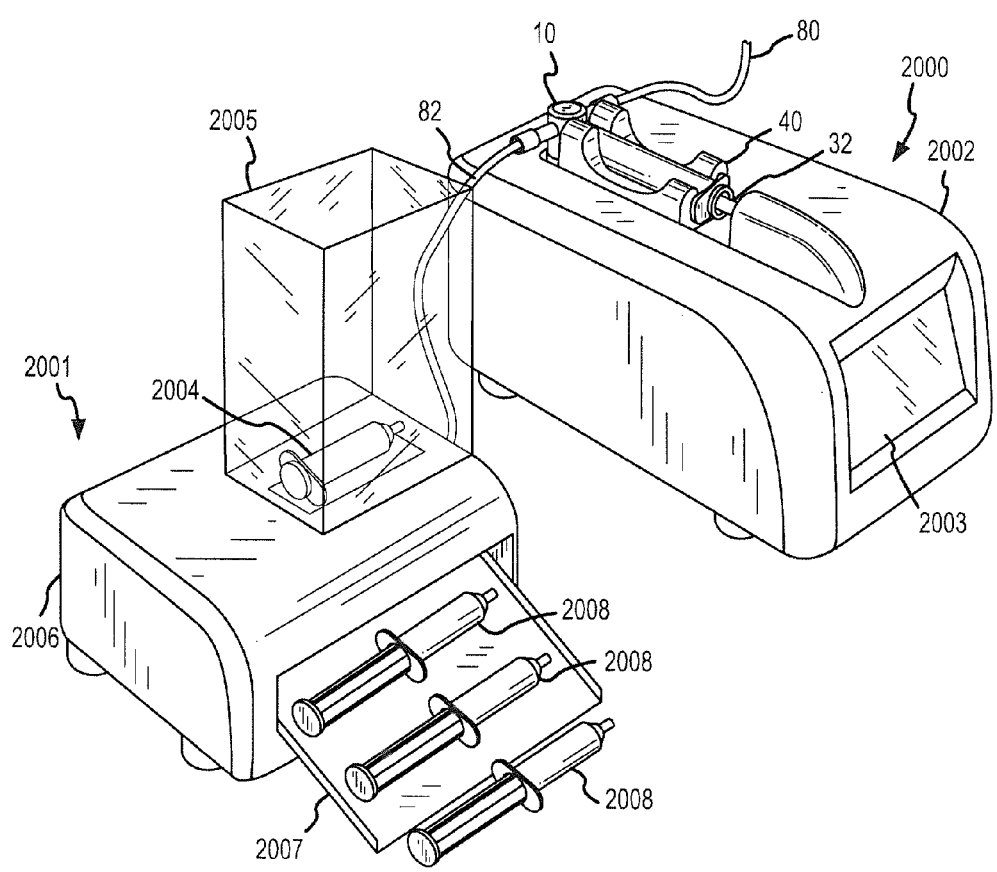
FIG. 20 is a perspective view of one embodiment of an automated liquid filling system and an automated syringe handling system.

FIG. 20 is a perspective view of one embodiment of an automated liquid filling system 2000 interconnected to an automated syringe handling system 2001. The automated liquid filling system 2000 is illustrated with the disposable 10 installed in the mount 40 with the piston drive member 32 engaged with the disposable 10. Other components of the drive system 30 are located within a housing 2002 of the automated liquid filling system 2000. A user interface display 2003 is located in a front portion of the automated liquid filling system 2000. The user interface display 2003 may be a touchscreen interface displaying menus and functioning as previously described with respect to the FIGS. 11a-11b.

The first fluid line 80 may be interconnected to any medical liquid source (not shown in FIG. 20) discussed herein. As illustrated, the second fluid line 82 is interconnected to the disposable 10 and to the automated syringe handling system 2001. The automated syringe handling system 2001 may automatically take syringes, such as syringe 2004, that have been loaded into a hopper 2005, and transfer them into a filling position within a housing 2006. In the filling position within the housing 2006 the automated syringe handling system 2001 may fluidly interconnect a syringe with the second fluid line 82. Once interconnected, the automated liquid filling system 2000 may proceed to pump a medical liquid through the second fluid line 82 and into the syringe within the housing 2006. Once the syringe within the housing 2006 is filled to a predetermined level with the medical liquid, the filled syringe, such as filled syringes 2008, may be transferred to an output tray 2007.

To coordinate the interconnection of the second fluid line 82 to a syringe located in a filling position within the automated syringe handling system 2001 with the pumping action of the automated liquid filling system 2000, the automated liquid filling system 2000 may be in communication with the automated syringe handling system 2001. This communication may be via a wireless link, an Ethernet connection, a Universal Serial Bus (USB) connection, or via any other communication method known to those skilled in the art.

The automated liquid filling system 2000 may also be in communication with other devices (e.g., personal computers (PCs), labeling devices, and one or more manifolds 64). This communication may be through a direct link or through a network connection. The user interface functions previously described in connection with the user interface 70 may also be performed remotely on a PC or other device. The remote device may be located distally from the automated liquid filling system 2000. For example, it is well known that some chemotherapy drugs have a high level of toxicity and unintentional contact should be minimized. Therefore, if the automated liquid filling system 2000 is being used to process such chemotherapy medicine, the remote device, such as a PC, may be located in a different room or on the other side of a barrier from the automated liquid filling system 2000. This would enable a user to adjust parameters and monitor the automated liquid filling system 2000 while minimizing potential contact with the fluids being handled by the automated liquid filling system 2000.

The automated liquid filling system 2000 may also be interconnected with more sophisticated medical container handling systems than that of the automated syringe handling system 2001 illustrated in FIG. 20. For example, the automated liquid filling system 2000 may be interconnected to a syringe handling system capable of handling, fluidly interconnecting, and labeling medical containers (for example the RAPID-FILL ASF produced by Baxa Corporation of Englewood, Colo., U.S.A.). In such interconnected systems, a user may only need to enter information one time (for example at the automated liquid filling system 2000, the syringe handling system, or a PC), and the system may automatically fill and label a plurality of medical containers.

The automated liquid filling system 2000 may also be interconnected to the Internet. Via such an interconnection, the software of the automated liquid filling system 2000 may be remotely upgraded or altered. These upgrades may, for example, improve functionality, improve self-diagnostic capabilities, or improve the user interface.

The automated liquid filling system 2000 may also include the capability to read Radio Frequency Identification (RFID) tags. For example, medical liquid containers interconnected to the first fluid line 80 may contain RFID tags. The automated liquid filling system 2000, may read the RFID tags and verify that the correct medical liquid container is interconnected. Once the medical liquid is identified it through the reading of the RFID tags, the automated liquid filling system 2000 may also be operable to determine or look up characteristics of the medical liquid (e.g., viscosity) and use those characteristics to determine operational parameters or detect mislabeled medical liquid containers (e.g., detect if the viscosity of the liquid is different than expected for the medical liquid indicated by the RFID tag). Furthermore, the automated liquid filling system 2000 may forward the information regarding the medical liquid to other interconnected devices, such as the automated syringe handling system 2001 or an automated labeling device. If an incorrect medical liquid is interconnected to the automated liquid filling system 2000, the system may be operable to read the RFID tags of the incorrect medical liquid and sound an alarm to inform a user of the error. The automated liquid filling system 2000 may also be operable to prevent any operation while an incorrect medical liquid interconnection is detected.

The functionality described in conjunction with the RFID tags may also be achieved with barcoding wherein the automated liquid filling system 2000 may include a barcode reader to read bar codes attached to a medical liquid container(s) to be interconnected to the first fluid line 80. Other systems of medical liquid container verification known to those skilled in the art may also be incorporated into the automated liquid filling system 2000.

As may be appreciated, the use of first, second and other numerical indictors in relation to the above described component, positions and other descriptions provided above is not meant to indicate any particular order of use of the filling system as such use is generally for descriptive purposes and is not intended to limit the scope of the present invention. Moreover, the aspects, approaches and/or embodiments described above are for exemplary purposes only and are not intended to limit the scope of the present invention. Various adaptations, modifications and extensions of the described system/method will be apparent to those skilled in the art and are intended to be within the scope of the invention as defined by the claims that follow.

What is claimed:

1. A disposable for use in a system for automated filling of at least one interconnectable receptacle with a medical liquid, said system including an automated drive system with a valve drive member having one of a complimentary projection and a receiving member, comprising:
   a housing comprising a tubular member and a valve housing;
   a piston slidably disposed in said tubular member for retraction and advancement within at least a first portion of said tubular member;
   a valve disposed within said valve housing and fluidly interconnected to said tubular member proximal to said piston, wherein said valve includes a valve stem slidably disposed within said valve housing and comprising the other of said complimentary projection and receiving member, wherein said other of said complimentary projection and receiving member is selectively connectable to and disconnectable from said one of said complimentary projection and receiving member, and wherein said other of said complimentary projection and receiving member is operable for automated positioning by said one of said complimentary projection and receiving member in at least a first valve position and a second valve position when said other of said complimentary projection and receiving member is connected to said one of said complimentary projection and receiving member; and
   a plurality of ports,
   wherein in said first valve position a first valve port is fluidly interconnected to said tubular member, and
   wherein in said second valve position a second valve port is fluidly interconnected to said tubular member.

2. A disposable as recited in claim 1, further comprising:
   a seal member for sealing a distal end of said first portion of said tubular member wherein said seal member is interconnected to said piston for co-movement therewith and slidable engagement within a second portion of said tubular member, said second portion being located distal to said first portion.

3. A disposable as recited in claim 2, wherein said first and second portions of said tubular member are each cylindrical and have first and second diameters, respectively, and wherein said second diameter is greater than said first diameter.

4. A disposable as recited in claim 2, wherein said seal member is spaced from said piston by a fixed distance that is at least as great as a length of said first portion of said tubular member.

5. A disposable as recited in claim 2, wherein said piston is positionable to at least a first piston position and to a second piston position within said tubular member, wherein said piston comprises:
a piston resilient member, wherein in said first piston position said piston resilient member is positioned within and sealably engages said first portion of said tubular member.

6. A disposable as recited in claim 5, wherein in said first piston position said piston resilient member is compressed to a first degree of compression, wherein in said second piston position said resilient member is compressed to a second degree of compression, wherein said first degree of compression is greater than said second degree of compression.

7. A disposable as recited in claim 2, wherein said piston is positionable to at least a first piston position and to a second piston position within said tubular member, wherein in said first piston position at least a portion of said piston is positioned within said first portion of said tubular member and at least a portion of said seal member is positioned within said second portion of said tubular member.

8. A disposable as recited in claim 2, wherein said piston is positionable to at least a first piston position and to a second piston position within said tubular member, wherein said tubular member further comprises:
a third portion located distal to said second portion, wherein said second and third portions are each cylindrical and have second and third diameters, respectively, and wherein said third diameter is greater than said second diameter.

9. A disposable as recited in claim 8, wherein said seal member comprises:
a seal resilient member, wherein in said first piston position said seal resilient member is compressably positioned within and sealably engages said second portion of said tubular member, wherein in said first piston position said seal resilient member is compressed to a first degree of compression, wherein in said second piston position said resilient member is compressed to a second degree of compression, wherein said first degree of compression is greater than said second degree of compression.

10. A disposable as recited in claim 2, further comprising:
a first connection member interconnected to said seal member.

11. A disposable as recited in claim 10, wherein said first connection member comprises:
a male connection member including a bulbous end portion.

12. A disposable as recited in claim 10, wherein said first connection member comprises:
a female connection member.

13. A disposable as recited in claim 12, wherein said female connection member comprises:
a plurality of fingers.

14. A disposable as recited in claim 13, wherein said plurality of fingers compress when located within said second portion of said tubular member.

15. A disposable as recited in claim 1, wherein said valve stem is rotatably disposed within said valve housing for automated rotative positioning by said one of said complimentary projection and receiving member when said other of said complimentary projection and receiving member is connected to said one of said complimentary projection and receiving member.

16. A disposable as recited in claim 15, said valve stem including:
at least first and second channels, wherein said first channel fluidly connects said first valve port and said tubular member only when said valve is in said first valve position, and wherein said second channel fluidly interconnects said second valve port and said tubular member only when said valve is in a said second valve position.

17. A disposable as recited in claim 16, wherein said valve stem comprises:
a stop portion, wherein in a third valve position said stop portion restricts fluid communication between said first port and said tubular member and between said second valve port and said tubular member.

18. A disposable as recited in claim 16, wherein said first and second channels comprise arcuate paths disposed about a perimeter of said valve stem and wherein said valve stem perimeter is defined in part by said first and second channels.

19. A disposable as recited in claim 1, said disposable further comprising:
a first fluid line interconnected at one end to said first valve port and interconnectable at another end to at least a first medical liquid source; and
a second fluid line interconnected at one end to said second valve port and interconnectable at another end to at least one vessel, wherein said disposable is operative to pump a medical liquid through said first fluid line, said tubular member, and said second fluid line free from occlusion of said first and second fluid lines.

20. A disposable as recited in claim 1, wherein said tubular member is substantially non-deformable.

21. A disposable as recited in claim 1, wherein the piston includes an end nipple and the tubular member includes a corresponding nozzle portion for receiving said end nipple.

22. A disposable as recited in claim 21, wherein the end nipple and the nozzle portion comprise corresponding conformal shapes.

23. A disposable as recited in claim 22, wherein the end nipple and the nozzle portion comprise corresponding lengths.

24. A disposable as recited in claim 21, wherein the piston is positionable to position the end nipple within the nozzle portion.

25. A disposable as recited in claim 1, wherein said other of said complimentary projection and receiving member is operable for rotatable driven positioning.

26. A disposable as recited in claim 1, wherein said one of said complimentary projection and receiving member comprises a male connection, wherein said other of said complimentary projection and receiving member comprises a female connection, and wherein said female member is integrally defined by said valve stem.

* * * * *